(12) United States Patent
Drew et al.

(10) Patent No.: US 12,221,491 B2
(45) Date of Patent: Feb. 11, 2025

(54) PSMD9 INHIBITORS FOR THE TREATMENT OF HEPATIC LIPID DYSREGULATION

(71) Applicants: Baker Heart and Diabetes Institute, Melbourne (AU); The Regents of the University of California, Oakland, CA (US); The University of Sydney, Sydney (AU)

(72) Inventors: Anna Christine Drew, Cheltenham (AU); Brian Gary Drew, Cheltenham (AU); Thomas de Aguiar Vallim, Los Angeles, CA (US); David James, Clontarf (AU)

(73) Assignees: Baker Heart and Diabetes Institute, Melbourne (AU); The Regents of the University of California; The University of Sydney, Sydney (AU)

( * ) Notice: Subject to any disclaimer, the term of this patent is extended or adjusted under 35 U.S.C. 154(b) by 1241 days.

(21) Appl. No.: 15/733,398

(22) PCT Filed: Jan. 21, 2019

(86) PCT No.: PCT/AU2019/050033
§ 371 (c)(1),
(2) Date: Jul. 20, 2020

(87) PCT Pub. No.: WO2019/140488
PCT Pub. Date: Jul. 25, 2019

(65) Prior Publication Data
US 2021/0095048 A1    Apr. 1, 2021

Related U.S. Application Data

(60) Provisional application No. 62/619,480, filed on Jan. 19, 2018.

(51) Int. Cl.
| | | |
|---|---|---|
| *C07K 16/40* | (2006.01) | |
| *A61K 31/7115* | (2006.01) | |
| *A61K 31/712* | (2006.01) | |
| *A61K 31/7125* | (2006.01) | |
| *A61K 31/713* | (2006.01) | |
| *A61K 39/00* | (2006.01) | |
| *A61P 1/16* | (2006.01) | |
| *C12N 15/86* | (2006.01) | |

(52) U.S. Cl.
CPC .......... *C07K 16/40* (2013.01); *A61K 31/7115* (2013.01); *A61K 31/712* (2013.01); *A61K 31/7125* (2013.01); *A61K 31/713* (2013.01); *A61P 1/16* (2018.01); *C12N 15/86* (2013.01); *A61K 2039/505* (2013.01)

(58) Field of Classification Search
CPC ....... C07K 16/40; A61P 1/16; A61K 31/7115; A61K 31/712; A61K 31/7125; A61K 31/713; A61K 2039/505; C12N 15/86
See application file for complete search history.

(56) References Cited

FOREIGN PATENT DOCUMENTS

| WO | 0065052 A1 | 11/2000 |
|---|---|---|
| WO | 2006007375 A2 | 1/2006 |
| WO | 2006007377 A2 | 1/2006 |
| WO | 2011059721 A1 | 5/2011 |

OTHER PUBLICATIONS

Sahu et al, A Novel Role for the Proteasomal chaperone PSMD9 and hnRNPA1 in enhancing IκBα degradation and NF-κB activation—functional relevance of predicted PDZ domain-motif interaction, FEBS Journal, 281, pp. 2688-2709, 2014 (Year: 2014).*
Alshehry Z.H. et al. "An Efficient Single Phase Method for the Extraction of Plasma Lipids" Metabolites 2015, 5, pp. 389-403.
Alshehry Z.H. et al. "Plasma Lipidomic Profiles Improve on Traditional Risk Factors for the Prediction of Cardiovascular Events in Type 2 Diabetes Mellitus" Circulation vol. 134, Issue 21, Nov. 22, 2016, pp. 1637-1650.
Andreux, P.A. et al. "Systems Genetics of Metabolism: The Use of the BXD Murine Reference Panel for Multiscalar Integration of Traits", Cell, Sep. 14, 2012, 150(6), pp. 1287-1299.
Azimifar, S.B. et al. "Cell-Type-Resolved Quantitative Proteomics of Murine Liver", Cell Metabolism 20, pp. 1076-1087, Dec. 2, 2014.
Baumeier, C., et al., "Caloric restriction and intermittent fasting alter hepatic lipid droplet proteome and diacylglycerol species and prevent diabetes in NZO mice", Biochimica et Biophysica Acta., 2015, vol. 1851, No. 5, pp. 566-576.
Bennett, B.J. et al. "A high-resolution association mapping panel for the dissection of complex traits in mice", Genome Research 20, pp. 281-290 (2010).
Chick, J.M. et al. "Defining the consequences of genetic variation on a proteome-wide scale", Nature, Jun. 23, 2016, 534(7608), pp. 500-505.
Churchill, G.A. et al. "The Collaborative Cross, a community resource for the genetic analysis of complex traits", Nature Genetics, pp. 1133-1137, vol. 36, No. 11, Nov. 2004.
Churchill, G.A. et al. "The Diversity Outbred Mouse Population", Mammalian Genome : Official Journal of the International Mammalian Genome Society, Oct. 2012, 23(9-10), pp. 713-718.
Cox, J. and Mann, M. "MaxQuant enables high peptide identification rates, individualized p.p.b.-range mass accuracies and proteome-wide protein quantification" Nature Biotechnology, vol. 26, pp. 1367-1372, published online Nov. 30, 200.

(Continued)

*Primary Examiner* — Mark Halvorson
*Assistant Examiner* — Dennis J Sullivan
(74) *Attorney, Agent, or Firm* — Storella & Witt, LLP

(57) ABSTRACT

The specification relates generally to the post-genomic identification of therapeutic targets and agents. In particular the specification relates to PSMD9 inhibitors and methods for preventing or treating metabolic disorders such as fatty liver disease that are associated with dysregulation of lipid homeostasis.

16 Claims, 21 Drawing Sheets
Specification includes a Sequence Listing.

(56) References Cited

OTHER PUBLICATIONS

Drew, B.G. et al "Estrogen Receptor (ER)-regulated Lipocalin 2 Expression in Adipose Tissue Links Obesity with Breast Cancer Progression" Journal of Biological Chemistry, vol. 290, No. 9, Feb. 27, 2015.
Eng, J.K. et al. "An Approach to Correlate Tandem Mass Spectral Data of Peptides with Amino Acid Sequences in a Protein Database", American Society for Mass Spectrometry, vol. 5, pp. 976-989 (1994).
Garzon, J.I. et al. "A computational interactome and functional annotation for the human proteome", eLife, 2016, 5, e18715.
Ghazalpour, et al. "Hybrid mouse diversity panel: a panel of inbred mouse strains suitable for analysis of complex genetic traits", Mammalian Genome, Oct. 2012, 23(9-10), pp. 680-692.
Harris R. et al. The Lancet Gastroenterology & Hepatology 2, 288-297 (2017).
Hvam, et al. "Fatty Acid-Modified Gapmer Antisense Oligonucleotide and Serum Albumin Constructs for Pharmacokinetic Modulation", Molecular Therapy, vol. 25, No. 7, Jul. 2017.
International Search Report and Written Opinion dated Mar. 26, 2019 for PCT application No. PCT/AU2019/050033.
Jiang, et al. "Prevention of obesity in mice by antisense oligonucleotide inhibitors of stearoyl-CoA desaturase-1", J. Clin. Invest., vol. 115, pp. 1030-1038, 2005. Epub Mar. 10, 2005.
Langfelder P., and, Horvath, S. "WGCNA: an R package for weighted correlation network analysis", BMC Bioinformatics, 2008, 9, 559.
Liu, H., et al., "Ufmylation and FATylation pathways are down regulated in human alcoholic and nonalcoholic steatohepatitis, and mice fed DDC, where Mallory-Denk bodies (MDBs) form", Experimental and Molecular Pathology, 2014, vol. 97, No. 1, pp. 81-88.
Luck, S. et al. "Rhythmic Degradation Explains and Unifies Circadian Transcriptome and Proteome Data", Cell Reports, 9, pp. 741-751, 2014.
Mota, et al. "Molecular Mechanisms of Lipotoxicity and Glucotoxicity in Nonalcoholic Fatty Liver Disease" Metabolism, Aug. 2016, 65(8), pp. 1049-1061.
Musso et al. "Non-alcoholic steatohepatitis: emerging molecular targets and therapeutic strategies", Nature Reviews, Drug Discovery, vol. 15, pp. 249-274, Apr. 2016.
Parks, B.W. et al. "Genetic Architecture of Insulin Resistance in theMouse", Cell Metabolism, 21, pp. 334-346, Feb. 3, 2015.
Parks, B.W. et al. "Genetic Control of Obesity and Gut Microbiota Composition in Response to High-Fat, High-Sucrose Diet in Mice", Cell Metabolism, Jan. 8, 2013, 17(1), pp. 141-152.
Prakash, et al. "Comprehensive Structure-Activity Relationship of Triantennary N-Acetylgalactosamine Conjugated Antisense Oligonucleotides for Targeted Delivery to Hepatocytes", J. Med. Chem., 2016, 59, pp. 2718-2733.
Singh, et al. "The Fatty Acid Synthase Inhibitor Platensimycin Improves Insulin Resistance without Inducing Liver Steatosis in Mice and Monkeys", PloSOne, 0164133, Oct. 3, 2016.
Tacer and Rozman, J. "Nonalcoholic Fatty Liver Disease: Focus on Lipoprotein and Lipid Deregulation", Lipids, vol. 2011, Article ID 783976, 14pages.
Thomas, M.K., et al., "Bridge-1, a novel PDZ-domain coactivator of E2A-mediated regulation of insulin gene transcription", Molecular and Cellular Biology, 1999, vol. 19, No. 12, pp. 8492-8504.
Volinic, J.L., et al., "Overexpression of the coactivator bridge-1 results in insulin deficiency and diabetes", Molecular Endocrinology, 2006, vol. 20, No. 1, pp. 167-182.
Watanabe, T.K. et al. "cDNA Cloning and Characterization of a Human Proteasomal Modulator Subunit, p27 (PSMD9)", Genomics, 50, pp. 241-250, 1998.
Williams, E.G. et al. "Systems proteomics of livermitochondria function", Science, Jun. 10, 2016, vol. 352, Issue 6291.
Wu, Y et al. "Multilayered Genetic and Omics Dissection of Mitochondrial Activity in a Mouse Reference Population", Cell, 2014, Sep. 11, 158(6), pp. 1415-1430.
Yu, Xing Xian et al. "Antisense Oligonucleotide Reduction of DGAT2 Expression Improves Hepatic Steatosis and Hyperlipidemia in Obese Mice" Hepatology, 42, pp. 362-371, 2005.
Extended European Search Report in corresponding European patent application No. EP19741237.2 mailed Sep. 29, 2021, 8 pages.
Gragnoli, Claudia. "Proteasome Modulator 9 SNPs are linked to hypertension in type 2 diabetes families", Cardiovasc Diabetology, Biomed Central, London, GB, 10(1); 77; 2011, XP021109035, 4 pages.
Yu, Rosie Z, et al "Clinical pharmacokinetics of second generation antisense oligonucleotides", Expert Opinion on Drug Metabolism & Toxology, vol. 9(2) 169-182, 2012, XP002144993.

* cited by examiner

B

C

A

A

B

SEQUENCE LISTING

<160> NUMBER OF SEQ ID NOS: 14

<210> SEQ ID NO 1
<211> LENGTH: 2368
<212> TYPE: DNA
<213> ORGANISM: Homo sapiens

<400> SEQUENCE: 1

```
gactgttctc gcgttcgcgg acggctgtgg tgttttggcg catgggcgga gccgtagtta      60
cggtcgactg gggcgtcgtc cctagcccgg gagccgggtc tctggagtcg cggcccgggg     120
ttcacgatgt ccgacgagga agcgaggcag agcggaggct cctcgcaggc cggcgtcgtg     180
actgtcagcg acgtccagga gctgatgcgg cgcaaggagg agatagaagc gcagatcaag     240
gccaactatg acgtgctgga aagccaaaaa ggcattggga tgaacgagcc gctggtggac     300
tgtgagggct acccccggtc agacgtggac ctgtaccaag tccgcaccgc caggcacaac     360
atcatatgcc tgcagaatga tcacaaggca gtgatgaagc aggtggagga ggccctgcac     420
cagctgcacg ctcgcgacaa ggagaagcag gcccgggaca tggctgaggc ccacaaagag     480
gccatgagcc gcaaactggg tcagagtgag agccagggcc ctccacgggc cttcgccaaa     540
gtgaacagca tcagccccgg ctccccagcc agcatcgcgg gtctgcaagt ggatgatgag     600
attgtggagt tcggctctgt gaacacccag aacttccagt cactgcataa cattggcagt     660
gtggtgcagc acagtgaggg gaagcccctg aatgtgacag tgatccgcag ggggggaaaaa    720 caccagctta gacttgttcc aacacgctgg gcaggaaaag gactgctggg ctgcaacatt     780
attcctctgc aaagatgatt gtccctgggg aacagtaaca ggaaagcatc ttcccttgcc     840
ctggacttgg gtctagggat ttccaacttg tcttctctcc ctgaagcata aggatctgga     900
agaggcttgt aacctgaact tctgtgtggt ggcagtactg tggcccacca gtgtaatctc     960
cctggattaa ggcattctta aaaacttagg cttggcctct ttcacaaatt aggccacggc    1020
cctaaatagg aattccctgg attgtgggca agtgggcgga agttattctg gcaggtactg    1080
gtgtgattat tattattatt tttaataaag agttttacag tgctgatatg accctgttgt    1140 cacccccagct gaatttctta tgaccctccc aaaccaaagc tcagatgggg tcagaagagc    1200
ttcatagaaa gttgggcaaa acaggctagc aattgcaaag tcaggctttg accaacatat    1260
ttctttgcac tgaggccttg ctgctgtgga tacggaaatg gttaagtact gtgcttcctc    1320
agcagctggg ctgtcaggcc catagtagct cccttttggag aacagggaaa gcctggaggc    1380
ttcccaggtg gccagcgtg gtgtcctgtc agcttcctct ttaggaaccc accagagggc     1440
agcaagctcc tttcacttcg ctagtaagaa ccctccgtt tttgtgtgtt tttgtttttg     1500
ttttctggag acaaggtctt gctttgtcac ccaggctgga gtgcagtgtc gtgatcaagg    1560
```

```
ttcactgaag ccttgacgct gtgggcactg cctcagccgc ccaagtatct gggaccacag    1620
gcgtgcacca ccatgcatag ctaatttatt ttttgtagag acagggtctc cctgtgttga    1680
ccaggttggt ctcgaactcc tgggctcaag cagtcctcct gccttggcct cctaaagtgc    1740
tgggatcaca ggcgtgagcc actgcgccca gcccactgct agtttgactt tttataattg    1800
aacctcctgg ctatgccctg agatcagcgc tattttgtaa accgctgagg tatggatagg    1860
aacgagtaga tcagacctct tgaaaatgct tattcttcct ccctttatt ttttgtctct     1920 tttaagatgg taaatggtt ctcagggatt cctgccaata ctttgaatta ttttttcctc     1980
tccatggtat cagtgttcat ttccccagtt cttgcacacc gctttctgtt ttggcagttc    2040
tgccaggcaa gccctgtgtt ccttgggact ggttttgctg tggttggata cagataccag    2100
cttgccttga tgggattggt attgctgtgt gcttccagcc acaggttctc acactcaatt    2160
ccaaagcctt cctattgggc gaattccctc aaactctatt tgacctgaca gccatacgta    2220
ttcccctctg gtagccacag acatgctgtg tttaccaatg tttgctgttt aaattgcatg    2280
ttctaattcc acgtattttc cagtctcttt tataaagtct cagactataa taacacagc    2340 ttgcccagtt taaaaaaaaa aaaaaaaa                                       2368

<210> SEQ ID NO 2
<211> LENGTH: 223
<212> TYPE: PRT
<213> ORGANISM: Homo sapiens

<400> SEQUENCE: 2

Met Ser Asp Glu Glu Ala Arg Gln Ser Gly Gly Ser Ser Gln Ala Gly
 1               5                   10                  15

Val Val Thr Val Ser Asp Val Gln Glu Leu Met Arg Arg Lys Glu Glu
             20                  25                  30

Ile Glu Ala Gln Ile Lys Ala Asn Tyr Asp Val Leu Glu Ser Gln Lys
         35                  40                  45

Gly Ile Gly Met Asn Glu Pro Leu Val Asp Cys Glu Gly Tyr Pro Arg
     50                  55                  60

Ser Asp Val Asp Leu Tyr Gln Val Arg Thr Ala Arg His Asn Ile Ile
 65                  70                  75                  80

Cys Leu Gln Asn Asp His Lys Ala Val Met Lys Gln Val Glu Glu Ala
                 85                  90                  95

Leu His Gln Leu His Ala Arg Asp Lys Glu Lys Gln Ala Arg Asp Met
            100                 105                 110

Ala Glu Ala His Lys Glu Ala Met Ser Arg Lys Leu Gly Gln Ser Glu
        115                 120                 125

Ser Gln Gly Pro Pro Arg Ala Phe Ala Lys Val Asn Ser Ile Ser Pro
    130                 135                 140

Gly Ser Pro Ala Ser Ile Ala Gly Leu Gln Val Asp Asp Glu Ile Val
145                 150                 155                 160

Glu Phe Gly Ser Val Asn Thr Gln Asn Phe Gln Ser Leu His Asn Ile
                165                 170                 175

Gly Ser Val Val Gln His Ser Glu Gly Lys Pro Leu Asn Val Thr Val
            180                 185                 190

Ile Arg Arg Gly Glu Lys His Gln Leu Arg Leu Val Pro Thr Arg Trp
        195                 200                 205

Ala Gly Lys Gly Leu Leu Gly Cys Asn Ile Ile Pro Leu Gln Arg
    210                 215                 220
```

<210> SEQ ID NO 3
<211> LENGTH: 2610
<212> TYPE: DNA
<213> ORGANISM: Mus musculus

<400> SEQUENCE: 3

| | | | | | |
|---|---|---|---|---|---|
| atctgtttcc | gtacttgcgc | gttggctgag | ctgttttggc | cccggggagg | acccgtagcc | 60 |
| tcagcctcgg | ctggcgtccg | tagccgggaa | acccagaact | ctagcttgag | gtccgcgatg | 120 |
| tcgggtgaag | acgttccgca | ccgggcagag | tcctccgagg | cccgtgcggc | cgcggtcagc | 180 |
| gacatccagg | atctgatgcg | acgcaaggag | gagatcgagg | cggagatcaa | ggctaattac | 240 |
| gacgtcctga | agagccaaaa | aggaattggc | atgaacgaac | cgctggtgga | ctgtgagggc | 300 |
| tatccccggg | cggatgtgga | cttgtaccag | gtccgaacag | caaggcacaa | catcatctgt | 360 |
| ctccagaatg | atcacaaggc | actgatgaag | caagtggagg | aggccctgca | ccagctgcac | 420 |
| gctcgggaca | agagaagca | ggctcgggac | atggctgaag | cccgagaaga | ggccatgaac | 480 |
| cgcaggctgg | cctccaacag | ccccgtcctg | ccccaggcct | ttgccagagt | gaacagtatc | 540 |
| agccccggtt | ccccagccag | tattgcgggc | ctgcaagtgg | atgacgaaat | tgtggagttc | 600 |
| ggctccgtga | acacccaaaa | cttccagtca | gtgcagaacg | tgggcactgt | ggtgcagcat | 660 |
| agcgagggga | agcccctgaa | tgtgacggtg | atccgcagag | gagagaagca | ccagctcaga | 720 |
| ctgattccaa | cccgctgggc | aggaaaagga | ctgctgggct | gcaacattat | tcctctccag | 780 |
| agatgactgt | ttcctgggat | ctgcctgcag | gaagctgcct | cagctggccc | cgtgcttggg | 840 |
| cctggaggcg | tttcctcgtt | ctctaggctc | ccttaagtgt | aaggatctgg | agaagaatgg | 900 |
| tcgaagcctg | ggcatcgagg | tggaagagac | gctttggctg | cctgatgtaa | tctctctggg | 960 |
| ttgaggcatt | attaaaagtg | tgatttgtgc | ctagctacgt | cttgtgcaaa | ttaggccata | 1020 |
| gcctgtctgg | gaattctcta | gattatgagc | cagtgagtgg | ggatgactct | ggcgagtaat | 1080 |
| gatttgatgt | cattttcctt | ttggagacgg | actcagtgtg | taatcctgac | tatcctggaa | 1140 |
| ttccctgtgt | agaccaggct | ggccttgagc | tgacagagat | ccccctgcct | ctgcctcatt | 1200 |
| agtattggga | tgagaggcat | atactgacat | ggctggctag | actctgagga | atatgtatta | 1260 |
| tacatatata | atttatactt | attttttgaga | atttcgtaca | tgcacatagt | acatttctat | 1320 |
| atttcctgtc | atctcaagtc | cctctcagac | ctcccctcgt | acccacttcc | caggttcttg | 1380 |
| ccctcttttg | ttttttttct | ttttaaataa | ataacctact | aagtgccatt | tgtgctgtca | 1440 |
| gtatattcat | ggtgtgggat | cttccactgg | aggaatgtgg | tcaaccttcc | agagaccaca | 1500 |
| cccctaacct | ccacaggact | tgagtacccc | tacttttttct | tggaagcagg | gtctcatgta | 1560 |
| gcccagtcca | gcctcagatt | tgccttgaag | ctgaagatgt | tctcttctgc | tgtctctccc | 1620 |
| tccaatgtcc | aactgcagta | tcacccaccg | cctaggggtg | ggggcttgct | ggagaccgga | 1680 |
| tctcacaagt | tcagactggc | ctggagctca | gtgtacccgc | actggcctta | cccttgggat | 1740 |
| cttgctgccc | tggtctcctg | gtattatagt | gtatgccacc | aaaccttgtt | acaggttaga | 1800 |
| gaaactgtca | gataaagcca | gtcttgtagc | tgtgtgattg | tgaccactgt | cagtcccacc | 1860 |
| aggatgccct | gtgagctcac | agccaagccc | aggaggagtt | gggaaggaag | tcctgcgaag | 1920 |
| caaacgagtt | cctgggccgc | agtccggttg | attcttgggt | gggaaactga | agcggagc | 1980 |
| tcagactcta | ggcaagtgtc | cctccgtggg | ctgagcagct | ggcagtctct | accctggagc | 2040 |
| agtgctttga | gagcctgatg | catcctctga | ggctgaggct | gtggagtcac | cgtagcccca | 2100 |
| ttaagaaatc | agcaaagacc | aggtgtggtg | gctcaaacgt | tttaatccca | gcactcagga | 2160 |

| | | |
|---|---|---|
| ggcagggca ggcggatttc tgagttaagg ccagcctggt ctacagagtg agctccagga | 2220 |
| cagccaagga aggctacaca gaaaaattct gtctcaaaac aaaatttgca aaggtcacag | 2280 |
| gtcacgaggc cttgcaggtt acccagtatg atattggctt cctcttcagt aacccactgg | 2340 |
| aaaccagcaa gcttccttta cttctacagt aaaagacccc gcagatgggc ctgatttggc | 2400 |
| ttttatagtt gagcctcccc accgggcggt ggtggtgtac acctttaatc ccagcactca | 2460 |
| ggaggcagag agaggcaggc agatctcaga gtttgaggct agcctggtct acagagtgag | 2520 |
| ttccaggaca gccagggcta cacagagaaa acctgtatgg aaaacaaaaa taaaacaaat | 2580 |
| ttaaaaaaca aaaaaaaaaa aaaaaaaaa | 2610 |

<210> SEQ ID NO 4
<211> LENGTH: 222
<212> TYPE: PRT
<213> ORGANISM: Mus musculus

<400> SEQUENCE: 4

Met Ser Gly Glu Asp Val Pro His Arg Ala Glu Ser Ser Glu Ala Arg
1               5                   10                  15

Ala Ala Ala Val Ser Asp Ile Gln Asp Leu Met Arg Arg Lys Glu Glu
            20                  25                  30

Ile Glu Ala Glu Ile Lys Ala Asn Tyr Asp Val Leu Glu Ser Gln Lys
        35                  40                  45

Gly Ile Gly Met Asn Glu Pro Leu Val Asp Cys Glu Gly Tyr Pro Arg
    50                  55                  60

Ala Asp Val Asp Leu Tyr Gln Val Arg Thr Ala Arg His Asn Ile Ile
65                  70                  75                  80

Cys Leu Gln Asn Asp His Lys Ala Leu Met Lys Gln Val Glu Glu Ala
                85                  90                  95

Leu His Gln Leu His Ala Arg Asp Lys Glu Lys Gln Ala Arg Asp Met
            100                 105                 110

Ala Glu Ala Arg Glu Glu Ala Met Asn Arg Arg Leu Ala Ser Asn Ser
        115                 120                 125

Pro Val Leu Pro Gln Ala Phe Ala Arg Val Asn Ser Ile Ser Pro Gly
    130                 135                 140

Ser Pro Ala Ser Ile Ala Gly Leu Gln Val Asp Asp Glu Ile Val Glu
145                 150                 155                 160

Phe Gly Ser Val Asn Thr Gln Asn Phe Gln Ser Val Gln Asn Val Gly
                165                 170                 175

Thr Val Val Gln His Ser Glu Gly Lys Pro Leu Asn Val Thr Val Ile
            180                 185                 190

Arg Arg Gly Glu Lys His Gln Leu Arg Leu Ile Pro Thr Arg Trp Ala
        195                 200                 205

Gly Lys Gly Leu Leu Gly Cys Asn Ile Ile Pro Leu Gln Arg
    210                 215                 220

<210> SEQ ID NO 5
<211> LENGTH: 669
<212> TYPE: DNA
<213> ORGANISM: Mus musculus

<400> SEQUENCE: 5

| | | |
|---|---|---|
| atgtcgggtg aagacgttcc gcaccgggca gagtcctccg aggcccgtgc ggccgcggtc | 60 |
| agcgacatcc aggatctgat gcgacgcaag gaggagatcg aggcggagat caaggctaat | 120 |
| tacgacgtcc tggagagcca aaaaggaatt ggcatgaacg aaccgctggt ggactgtgag | 180 |

```
ggctatcccc gggcggatgt ggacttgtac caggtccgaa cagcaaggca caacatcatc    240
tgtctccaga atgatcacaa ggcactgatg aagcaagtgg aggaggccct gcaccagctg    300
cacgctcggg acaaagagaa gcaggctcgg acatggctg aagcccgaga agaggccatg     360
aaccgcaggc tggcctccaa cagccccgtc ctgccccagg cctttgccag agtgaacagt    420
atcagccccg gttccccagc cagtattgcg ggcctgcaag tggatgacga aattgtggag    480
ttcggctccg tgaacaccca aaacttccag tcagtgcaga acgtgggcac tgtggtgcag    540
catagcgagg ggaagcccct gaatgtgacg gtgatccgca gaggagagaa gcaccagctc    600
agactgattc caacccgctg ggcaggaaaa ggactgctgg gctgcaacat tattcctctc    660
cagagatga                                                           669
```

```
<210> SEQ ID NO 6
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 6
ctctatgggt gccagc                                                    16

<210> SEQ ID NO 7
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 7
ctctatctga gcacac                                                    16

<210> SEQ ID NO 8
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 8
gtatttttag ccagac                                                    16

<210> SEQ ID NO 9
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 9
ggccaatacg ccgtca                                                    16

<210> SEQ ID NO 10
<211> LENGTH: 2610
<212> TYPE: DNA
<213> ORGANISM: Mus musculus

<400> SEQUENCE: 10
atctgtttcc gtacttgcgc gttggctgag ctgttttggc cccggggagg acccgtagcc    60
tcagcctcgg ctggcgtccg tagccgggaa acccagaact ctagcttgag gtccgcgatg    120
```

```
tcgggtgaag acgttccgca ccgggcagag tcctccgagg cccgtgcggc cgcggtcagc    180
gacatccagg atctgatgcg acgcaaggag gagatcgagg cggagatcaa ggctaattac    240
gacgtcctgg agagccaaaa aggaattggc atgaacgaac cgctggtgga ctgtgagggc    300
tatccccggg cggatgtgga cttgtaccag gtccgaacag caaggcacaa catcatctgt    360
ctccagaatg atcacaaggc actgatgaag caagtggagg aggccctgca ccagctgcac    420
gctcgggaca agagaagca ggctcgggac atggctgaag cccgagaaga ggccatgaac    480
cgcaggctgg cctccaacag ccccgtcctg ccccaggcct ttgccagagt gaacagtatc    540
agccccggtt ccccagccag tattgcgggc ctgcaagtgg atgacgaaat tgtggagttc    600
ggctccgtga cacccaaaa cttccagtca gtgcagaacg tgggcactgt ggtgcagcat    660
agcgagggga agccctgaa tgtgacggtg atccgcagag gagagaagca ccagctcaga    720
ctgattccaa cccgctgggc aggaaaagga ctgctgggct gcaacattat tcctctccag    780
agatgactgt ttcctgggat ctgcctgcag gaagctgcct cagctggccc cgtgcttggg    840
cctggaggcg tttcctcgtt tctaggctc ccttaagtgt aaggatctgg agaagaatgg    900
tcgaagcctg gcatcgagg tggaagagac gctttggctg cctgatgtaa tctctctggg    960
ttgaggcatt attaaaagtg tgatttgtgc ctagctacgc cttgtgcaaa ttaggccata   1020
gcctgtctgg gaattctcta gattatgagc cagtgagtgg ggatgactct ggcgagtaat   1080
gatttgatgt cattttcctt ttggagacgg actcagtgtg taatcctgac tatcctggaa   1140
ttccctgtgt agaccaggct ggccttgagc tgacagagat ccccctgcct ctgcctcatt   1200
agtattggga tgagaggcat atactgacat ggctggctag actctgagga atatgtatta   1260
tacatatata attttatactt atttttgaga atttcgtaca tgcacatagt acatttctat   1320
atttcctgtc atctcaagtc cctctcagac ctcccctcgt acccacttcc caggttcttg   1380
ccctcttttg tttttttttct ttttaaataa ataacctact aagtgccatt tgtgctgtca   1440
gtatattcat ggtgtgggat cttccactgg aggaatgtgg tcaaccttcc agagaccaca   1500 cccctaaccct ccacaggact tgagtacccc tactttttct tggaagcagg gtctcatgta   1560
gcccagtcca gcctcagatt tgccttgaag ctgaagatgt tctcttctgc tgtctctccc   1620
tccaatgtcc aactgcagta tcacccaccg cctagggtg ggggcttgct ggagaccgga   1680
tctcacaagt tcagactggc ctggagctca gtgtaccccgc actggcctta cccttgggat   1740
cttgctgccc tggtctcctg gtattatagt gtatgccacc aaaccttgtt acaggttaga   1800
gaaactgtca gataaagcca gtcttgtagc tgtgtgattg tgaccactgt cagtcccacc   1860
aggatgccct gtgagctcac agccaagccc aggaggagtt gggaaggaag tcctgcgaag   1920
caaacgagtt cctgggccgc agtccggttg attcttgggt gggaaactga agccggagc    1980 tcagactcta ggcaagtgtc cctccgtggg ctgagcagct ggcagtctct accctggagc   2040
agtgctttga gagcctgatg catcctctga ggctgaggct gtggagtcac cgtagcccca   2100
ttaagaaatc agcaaagacc aggtgtggtg gctcaaacgt tttaatccca gcactcagga   2160
ggcaggggca ggcggatttc tgagttaagg ccagcctggt ctacagagtg agctccagga   2220
cagccaagga aggctacaca gaaaaattct gtctcaaaac aaaatttgca aaggtcacag   2280
gtcacgaggc cttgcaggtt acccagtatg atattggctt cctcttcagt aacccactgg   2340
aaaccagcaa gcttccttta cttctacagt aaaagacccc gcagatgggc ctgatttggc   2400
ttttatagtt gagcctcccc accgggcggt ggtggtgtac acctttaatc ccagcactca   2460
ggaggcagag agaggcaggc agatctcaga gtttgaggct agcctggtct acagagtgag   2520
```

| | |
|---|---|
| ttccaggaca gccagggcta cacagagaaa acctgtatgg aaaacaaaaa taaaacaaat | 2580 |
| ttaaaaaaca aaaaaaaaaa aaaaaaaaaa | 2610 |

<210> SEQ ID NO 11
<211> LENGTH: 28000
<212> TYPE: DNA
<213> ORGANISM: Mus musculus

<400> SEQUENCE: 11

| | |
|---|---|
| gtgtagcccc tggctgtcct ggaactcact ctgtagacca ggctggcctt gaactcaggg | 60 |
| atcagcctgc ctctgtgtcc ctagtgctgg gagtaaaggc atgtgccacc atggtcctct | 120 |
| taaatggttt tcttagctgt caaatatggg caccaataca tatggtttct ttgggttgtt | 180 |
| gaactatcac atataggcat gtagaactgt atttgagatt ctctgtctca ttcaggtttt | 240 |
| acattatatc ttcatgtgcc tcaccgctga gtaaaactct cattccttat tactattttt | 300 |
| tttaaaaaca tgctttttta aaaacaaaa taaagagaaa ccctgtcttg aaaaatcaaa | 360 |
| accaaccaac caaccaacca gaaaaaccca agaacttac tttatacttc ctgtgcatca | 420 |
| gtgttttgcc tgagtgtgtg tctgtgtgac ggtgtcagag ggtggagttg cagacagttg | 480 |
| tgagccgcca tgcagatgtt gagagttgaa cctgggaaga gcagtcagtg cccttaactg | 540 |
| ctgagccatc tctccagcct ccttattact atttaaaaat ttttattttt atcatatgta | 600 |
| tgtgagttgg ctagttttat gtcaacttga tgcaacctag agttgtctaa aggaagatgg | 660 |
| aaactcaatt gaaaaaatgc ctccttaagt tccacctgta gggcattgcc ttaattagtt | 720 |
| attgatggga gtgtgttcta cccattttgg gctggtggtc ctgagttcta taagaaaata | 780 |
| ggctgagtaa gacacaagga gcaagtcagt aagcagcaca cctccattgg ctcctgcctc | 840 |
| caggctcctg cactgtttga attcttgtcc tgatttcctt aaatgatgaa cagttatata | 900 |
| aggaaacgta agccagatga agcttttcct tcctacattg ctttggcctt tgtactggct | 960 |
| ggttttgtgt caccttgacc cgggctggat ttatcaccga gaaggagct tcagctggag | 1020 |
| aagtgccgcc atgagatcca gctgtaaggc attttctcaa ttagtgatca aggggaaagg | 1080 |
| cccccttgtgg gtggtgccag ctctgggctg gtagtcttag ttctataaga aagcaagctg | 1140 |
| agcaagccag gggaagcaag ccagtaaaga acatccctgc atggcctctg catcagctcc | 1200 |
| tgcttcctga cctgcttgag gtccagtcct gactttggtg atgaacattg ttgtggaagt | 1260 |
| gtaagctaaa taaacccttt cctccccact ttgcttgttg gtcatgatgt ttgcgcagga | 1320 |
| atagaaacct tgactaacac agccatgcta ttttatcaca gcaatagaac cttaactaag | 1380 |
| acagtgtgca agtgttttgc ctgcatatac gtatgtgtcc taagtgcgtg ctggatggtt | 1440 |
| gtggaggtca ggtgagggca ttggagaccc tggagctaga gtaacagaca gttgtaagct | 1500 |
| tccatgtaag tactgggaac ccaggccctc tgcaagagct ttaagtatgt tcttaacctc | 1560 |
| tgaaccatct ctctacccca caccccagtt tctatgttta cctacattta tagaggcctg | 1620 |
| acacagtttc atattcttta ccacttcagt cttgtgggga attcatgaga ggagactgct | 1680 |
| cagatagagt tttaatctga tagtctttat tagtgagcca gtacaacact aagtgtttgg | 1740 |
| gaccccagtg gagcactgag cctttttcag ggtaagcttt ttgagcacaa aaaccgggtc | 1800 |
| ctggggtgat ataccttagt tcacaagagc aattagccag gagcacaacc actgaagcca | 1860 |
| aaaagcaagg ttcgtgcatg gagagacttt cccacagctg tggacttgga tggcttccgg | 1920 |
| ctttgtttta gttttggcag gtggtgctgt ctgtgtgctg tgttttccag cctgagtggt | 1980 |

```
actttctttta tggagtcggt tgtactaagg tctgggggcc tgttacacca gcacctcgtg   2040
acagaggtga aagtcaataa atacttggac acccttaaga gacacgttgc tagggtgtgt   2100
gtactctgat caggatccaa agggaataaa ttagtaaata aaatgaaaa aaaagagcga    2160 gagatattac tgttagtgtc acacaataag gtcagagagc agaaggtgaa attatttaag   2220
gtcacatgga atatatatag tcggtgttaa tggtccaact ttgaacatag gttgtaccat   2280
gaggatcccc agcccgaaag tggctgggga tatagctgag ttggtagagt gttcctgatc   2340
cccaatattt cataaaccat acctggtggt acatgcctgt aatccctgcc tgtggaggga   2400
gcagatggag tatcagatgc tcaaaggcac tgggcacact aggttataaa gaaggaaaaa   2460
aaaaaaggtc ttgaagtttt gatgaggata ggttgaggga ggtgcgaaat ggatagaatg   2520
ggagtggggg gttagagggt gtctgtgatc atgacaataa gaaatagaat attctaaaaa   2580
cttggggaga gcttcaaggt cgccttcatc tacacaatga gttagaggcc tgcctgagat   2640
gcagtaaatc ttgtctggaa aagaaaaag aaagaaaca gaaacaaaa acaaatcgc      2700 ttgaaagcct ctttcaaaca ctcaggggct tcgtagatgt taagaactga agtgtcaagg   2760
ttggcaagac tggatcctct tacatttata cagctggtat ccagtttact cagccttcag   2820
atgagtgaat gaaaaaagt gtaagccaga tgtggtggct ttaatcccag cacttgggag    2880
cagaggcagg aggatttctg agtttgaggc cagcctggtc tacagagtga gttccaggac   2940
agccagggat acacagagaa accctgtctt gaaaaacggg gtggggtggg ggggtgggga   3000
aacggacgga tggagggacg gggacagaat gaaaaagaaa ggaatgaaca agaaaagtgg   3060
aaatgagtca ggataaagtg ggagtaaata cctatgtcct ctatgggcct atttatctct   3120
accgggtcat ctgaaaacca cgtggtctat ctagccggtg accccgccca cttccaagct   3180
ccacccttca tctgtttccg tacttgcgcg ttggctgagc tgttttggcc ccggggagga   3240
cccgtagcct cagcctcggc tggcgtccgt agccgggaaa cccagaactc tagcttgagg   3300
tccgcgatgt cgggtgaaga cgttccgcac cgggcagagt cctccgaggc ccgtgcggcc   3360
gcggtcagcg acatccagga tctgatgcga cgcaaggagg agatcgaggc ggagatcaag   3420
gctaattacg acgtcctgga gagcgtgagt gtggcgggga ggcctgcgga cgaggctcgg   3480
ggtcgctgcc aagcagtgtc ctagaggggg tctttgctgc gtgccacacg cccctttaag   3540
cattttttct ttacgtggga ttaattttca ttttcggaag cattaacttt gcattttaaa   3600
gttttttgtt tgtttgtttt taacgcagcc cctaagctgg cttcgaactc gtgatcctcc   3660
tgcttcatct ttctgagtgc gggaatcgcg ggcctgtgca accatgatat aggccttagt   3720
gaaactgcct cggtcgcaag gatagactat ttgctgaggc atagtgataa tcgctactgt   3780
cactttctgt aggtgacatt accaggtttg gcctcgccac ccgctttttct ttaggacttt   3840 ataaatgtca actgggagaa ttaattgggc atcttgttaa aatgcacgtt gtagccaggg   3900
gaggcatccc tatttaagcc cagcgtttag agagtggagg caggggatc aggacttgag    3960 ggttattctt gcctacatag taagctcgag gctgtcctgg gttatattag accttgtctc   4020
aaaaaaaaac caaaaaaaaa aaaaaaaaa aaaacaaaa agaaaagta aaatgaaat       4080 gcagactcta attgggatag ggaaaagact ctggatttta agaaaccct cacctctgct    4140 aattgctctt ttaagtggag ccagattaag cacattgtct ttactgtaaa aggggaaaca   4200
gggccagagt ggagccaatg cttgcccagt taggaagggg gaatggttgg ctctgtgatc   4260
tgtttacctc ctaagcagat atattttca taaaaccccca agtcagtgta tagaggaagg    4320
ggaggctaaa tcacactcat tgctgggcac aatgacatct gggtgatggg tgccagatga   4380
```

```
cggtgtcata tagaggttct acaggccagg taggtgctga ccatgtgcct gaaaggtact   4440
atcttgtatg tgtgctgtgc caggaaactg tcacagcagt attgttaact tgtgtccctg   4500
aagctcaaag gggcggagtc aggggctgga gagatggctc agtggtttaa aggcactggc   4560
catcataagg actggagttg agatccagaa tttactactg tgtaagttca cacgcccgtg   4620
gagacgttta aacagacaca aatctcttta agaaaaaaa aacacaaaaa cccgtgtgtg   4680
tgtgtgtgtg tgtgtgtgtg tgtacacata tatctgtgta tgtatggata cacatatatg   4740
tgtatatatg tatgtgtata tgtatgtatg tatatgtgtg tgtgtataca catatatctg   4800
tgtgtgtgta tgaaaggaga agtcacttgt ttaaagtcac aggcctccgg cttggtaaag   4860
cttaaaacag ataaaaagca attttttgtt ttgttttgtc ttgttttttcg aatgagagtt   4920 tcttttttgta gctctggctg tcctgaactc agagatccac cagcctctgc ctctcaagtg   4980
ctaggattta aggcgtgcac taccatcggc tggcaaaaag caatttctta aactgcagta   5040
acttgcctaa ctccagtaga atcagacatc tcacgtattg tcttttggta ttggcctacc   5100
ctttactatt tagctgggtg tggtgttgca tacctgcagc ccgaagcaag caaaagcatg   5160
gagattgcca cacgttcagg gccagtctgt tttacacagt gagctctagg actatatagt   5220
ggaacagcaa gaccctgtct gaacaaacca gcgtttgggg aggctaggag tatagctcgg   5280
tttgtcggat gcataccgca gagacctcaa gacctgagtt tggtccctag aactcaaggc   5340
tgttactggt ccatgtctgg gatcccaact ggacaggcag agacagaaga tgcccgggtt   5400
tatgggcagc cagtccagcc tgtttgatga gctgtaggct ggtgagacag catgtctcaa   5460
aggaggtaga tagtgttcct gagatgcccc cttgagatta tcctctgact ggcacatgtg   5520
tggcatctgc atacacacaa acctattaga aaccaaatca aaagaggaaa aactataact   5580
attttctctt aaatataagg taagagtgta tgttaattgc ctctggctaa tttttttttt   5640
ttttggttgc tgagggcttg aatcttaaaa tttgtctgct ctgatttatt tcatattatt   5700
attattatta ttattatttt agggacaggc tcccagctgg gtggtgatgt ctcatttctt   5760
tattctaagc acttgggagg cagaggcagg tggatctctt gagtttgtgg tcagcctggt   5820
ctacagagtg agttccagga caatcagggc tacacagaga aaccctgtct caaaaaacaa   5880
aacagaaaaa aaaaaagaca ggctctcagt atgcagctta gactacatat gtgaaactct   5940
gtccctcccc cacataaaag taaaaacaga ttataaatga taaattagat atcactatta   6000
aaactcctat ttcataatac gtagtcaaga ctataagaag agaagccaca ggatggaagg   6060
aagtggttgc acatcctctc ataagctggt gtctgggata tagaaaacgg agcgataaaa   6120
cacagtcata aatacacaga tagtgtactg agaacagggc agagggtcta agtgaatggt   6180
ccttaaatta aatacatatg attgatagag aagctggtga acacattcag gacatcggtt   6240
aaaagctcca cgtgctcttg cagaggacct gggttcagtt cccagcactc acacatgcgt   6300
ggtaactgca cttccagggt acccgatgcc gcttctgacc tccgcaggca ccgcacacac   6360
atggtgcaca tctatccgta gatccaaaac acttgcacac atagaggaac tcttaaaggc   6420
ccagcatgct gaacagccac agtgtagtta aaatcacagt gccatactcc ctcatactca   6480
ccaggatggg gataacgaga atatgggtaa tatcttaagg agactatgga gaaattggaa   6540
ataccataca actgtaagat ggtgtaactg ctgtccaaaa acagttcggc agtttctcaa   6600
aaaggtaaac atagagttaa catagaactc agaaaatcca ttcctcattt gatattatga   6660
ttgttgcaaa tatatcatcc aaaagttcat acatagctgt agtgagagct ttggtttctt   6720
```

```
tggaaatgct tgggttttt tttttttttt tttaagattt atttatttat tatatgtaag    6780
tacactgtag ctgtctccag acgctccaga agagggcatc agatctcatt atggatggtt   6840
gtgagcctgg gatttgaact caggactttt tggaagagca ggcagtgctc ttaaccgctg   6900
agccagtctc cagcccggaa atgcttgttt ttgttataat cccaagtgcc caccacagca   6960
gctgattgtg atttgccttg aactccagca ggagcctggt tctgcaagct gtagctcgat   7020
cctgtgcttg ggtagcgtgg aattgtgggg gcttttttaga ggatatataa atgttagcgc  7080
tctgagccgt ggagttgttg tcggttgttg ggtggttgtt gttggttgct gttggtctag   7140
ctggttaagt agtcctatgc aaagaagaag aaattagata tcctgatcaa acttgcccca   7200
aggaactcag atgttcctaa tgagcaggaa gtagtctaac aatgacatcg ccccctttcc   7260
cctctaccct ttcttccctc ctgtcaagtc ttaggggggtt gaaagggtgg aaaaaaaaaa  7320
aaagggtgg agaagggtgg aagaaagaac acaaaatagc caaagttggg ctacacacac   7380
tgtttaaaat agctagaaaa caggaagcaa ctcatattct ctagctaaca gataagtgaa   7440
acatagtcaa cccatacagt ggggtttgaa ggtaacaagg agttgtgagt tatatataaa   7500
tacttgttca tgctattggg taaataaccc ttgaaagcat tgtgataaag aagatacaaa   7560
acaccttgta tcgtgtgtgt tatctctctc atcttgctat gtacttctgg ctatctccca   7620
gtacttacta tatagcccag gctagccttg aattcttggc agtttgttgc agcctcctgg   7680
gtgctgagat tataggtggg caccactaca cctagcttcc ttttttgaca cacgtctggc   7740
taaaaataca agctggcctt gaactcactc tgtagttcta gctggcctcc aatttataat   7800
tttcctgtct tggcttgcct caatgttggg attataagtg ggtgtcagtg tgcttggcat   7860
tgcaaggttt catgtatatg aaatgtcctg ttctgagtct cagatgttcc ctgaaggctc   7920
ccatattaaa agttgggtgc ccacagtgat gctcttgata catggtggaa cccttaagag   7980
gtgcagctct gtaggtcatt ggaagcatgc ccttggtggg gtggttactg taggttgtag   8040
ttggcatggc cttgctaggg tagctgctat aggtcattgg agggcttttt cttttttgtct  8100
tttccttcct cctaggatca tgatggaagt gacttccatg ataatgttct gcctctccac   8160
agagctaaaa acaaagagtc ccaaataaac ctaccgacag acatcaaaca acgcatctgc   8220
caagttctgt tctgaaactc caaaactatg agctccaata agcctcttct gtctatgttg   8280
gttataatac tcagacgtag tctcagagtt tcagagggac agtgtgggag cctgcctcac   8340
atacatagat agttgctaaa gctggcccta aagcagaggt ccctctagtt ccagtgactc   8400
aggaggctcc tcaggaggct gaggcaggag gattggttgg acccaggaaa cagcctgggt   8460
aacatagtga ggctaagtat aaagtgttaa aatgaatgca ctgtttgaa taaggcatag    8520
atttccagtg ttcagatcca gaacctgctg gtggatatca aatacaaagg cttccatcct   8580
tccctaactc ccagccactc ggtttctttc cctggcggca gccggtgcca tccagtgatg   8640
ggaggaatct tggtatgcct tgtaggtctt tatttttaga agagtccaaa ccctggtcct   8700
agctgcattc tctggagttt acgtcctgtt gggagggagg cgttgcagag gtcaggtgag   8760
ggatggagct gagagagaag gctctgaagg cccttggggt gttgtgttgt tgctttaatt   8820
aattggtttt ggagagatta tctcatgtac ccaaggctaa tctggagctc actgtgtaac   8880
caaggatgac cttgaacttt gatcctcctg cctctacatc ctgtaccacc aggtctagct   8940
tgggggtggg gggctggggg gataagtcca atgttttatg tatgctaggc aagcactcta   9000
gcaaccgagc tacatcctat atccctagcc ctacttatta ctgtgtgtgt gtgtgtgtgt   9060
gtgtgtgtgt gtgtgtgtgt gtactgtaga gaatcaaatc caagattggc atatgccagt   9120
```

```
gctctaccac tgaccatcca gccttgcttt gtgtacacta ttctcatgca ttgcttgcat   9180
tattttttaa agacttcatt ttatgaatgt gtatatagtg tggcccgggg cattgatgag   9240
gagtgcatat ggaggtcaga ggacagcttt gtgcagtttg tgtgccttt  tcatcttcat   9300 gtggacccca ggaattgaac tcaggttgtt ggtctttaat tcactgatcc atctctatga   9360
cctcgttgct ttcattatta atacttaatt aaaactggta cccactgcag agggtagcta   9420
taaggacaca gttacagagc ctgatgtgtg ctaaagacat cactatgtgc taaagacatc   9480
actgtgtggt cctcgtttct ttcatcatga gttagaagta caaggtctag ggaattgca    9540 tcttggtgtt ttcacctgtg agatttttt  ttaaccacat ctctttcctc agcaaaaag    9600 gaattggcat gaacgaaccg ctggtggact gtgagggcta tccccgggcg gatgtggact   9660
tgtaccaggt ccgaacagca aggcacaaca tcatctgtga gtgaccctcg ctggggctgt   9720
cttggcttgt ggtgggttg  ctggagacac aggggtgat  tagcattgag cactgcaaag   9780
cttttctgct ttgacacaat taccttgtca aagtaaggaa ctgagaagca agcggacagg   9840
gtggatggca gagttgcatg tcgatggctt tattattatt ttttttatt  ttaaatactt   9900 tgcttcaaag ctaaatgtgg tggcacacgc ctttgatccc agcattcagg aggcagaggt   9960
agatggatct ctgtgaggtt gagtccagcc tggtctacag agtgagtccc aggccagaca  10020
gctgaaaaaa aaccctgtct caaaacaaaa caaaacaaaa acaaacaaca aaaatccatg  10080
aacaaacaaa caaaaaaact tggcttcaag ctgggcatgg tggcacacag ctctaaggct  10140
agctgtttga ggccagtctg ggctgcatac aaaagtacag aacggggctg gggagatggc  10200
tcagtggtta agagcactca ctgactgcta ttccagaggt cctgagttca atcccagca   10260 acaatatggt ggctcacaac catctgtaac acaaccacct cttctggtgt gtctgaagaa  10320
agcaacaggg tactcacata cataaaggat tttttaaaa  aaagtaaaaa aacaaggaat  10380
gaaagcttta ctttgttatg ggacttcatt gaattaacaa tggaagccca aatcagtcac  10440
tccccagccc catggagtcc atgaagtagg ttcccactgt gcaaatagca aagacccagg  10500
ctggctctca gactgaagta tcagtataaa ggccagcaga accaggttct gcctgtcttc  10560
aggcccatgg ctgtgttcag gcaggagaca ggcgacagga ggaacggtcc tggcctccca  10620
ccctgagtgt gccattggtt agcattttcc tgccaggaag gctgggcaag cctgtcccgc  10680
tgcaggccca tcactctcct gagggagtct tacacatggc ctttgtctta atgaagtacc  10740
tgttagagaa tggcacctgc agaggacact gggtttgtgt ttctgttata acaagccaca  10800
agactgtatt gtgtctgaca gttctggagg tgagacagcc agaaggtctg ctgacagaat  10860
ccaggtgtca gtggggctgg ctcccctag  gggctggggc tggtggtgta cctttgtct   10920 ttgcagaggc cacctgtgtt tcctggctct tggccaggat cctctgtctt tagaagtagt  10980
gctcacatct ttctagcctt tgcagctgtt atggaatctt gtcctctccc cctcctgcct  11040 ccctcttag  cttgttaaga cccgggcccc cccagaaaat ccaggctcgt cccttctccc  11100
agggtcctga ggtcacatgt gcactggctt cgggatgagg gtgtgaacat cttttacttg  11160
gcactgtaga taatcagccc tccatcccag ctgtactagg gggtcagtca cccatggttt  11220
gcatttcatg atttccactg agtatgccgg actccggctt tatccacagt gttttggtaa  11280
aggagctgcc tttataagca gggtgcagag taagatgcac gctcccttaa agccacagtg  11340
tgggagagag cacctcagaa catccttttt cccctgaaga ttctgatgtt aaaaaggttc  11400
agtcttacag gaaataaact gaggagatgc ggagaatagg gaaactatgt gaagactgca  11460
```

```
aatgtgaggg aaattctgag cttaaccoca aaccoctgag cccccaggga tggggctcac    11520
cccttctgca gaagcagggc cggggaagtt tgccgaatgc tgattttcag tgctgattga    11580
cttcgtgtcc caacagcatt ctttccgctg acttgaactg cagcagtgtt atattctctg    11640
tgtttgtgtg tgggtgtgtg tgggcgcaca tgccctgctg ggagcggaac ctggggcttc    11700
gtgctagagc ttactgtacc acttaggctt ttcagctatg cttagcctat ttctggacgc    11760
tttacactgt tctactccat gttaatttta tatcatctta atgactttat tatgtgttaa    11820
taatatgatt gaacaattcc cccttattag tattcttttg aaagacaatt cccacaagtt    11880
taatgtattc ttaaacatgg attttcttaa gggaacaatc ctaggcttac attgaaattg    11940
ggaaagtaat acagaaaggt ctcatatgct gagtccttag tcgctaatca ccagcaagtg    12000
ctagcatggt acatttgtgg cagcttaaac ttaattttga ataattgct gcagaagtgt    12060
ttaccoccag gcaatgaaaa ccttttgaat tctgatatgg aattgtaata tatcagcaac    12120
tcagtcattg gtcctctcac ccacagcagt gtggagaata cagattgtgt ctaagacagt    12180
gactctactg taagcctccc tggcctgggg tctggttttt cccctcaca tctgcctctg     12240
tggactgagt acccaagtcc cctaatgcct gcgggcccta cctttgctca cagtgacagg    12300
caggctagat gaccacacag ccacacagcc ccacagtcac ggctcctgca gagttggaga    12360
gtctgtgacc caagggtgcc acatgtggat tggctatcag ggcgatggca gcaggcggcc    12420
ttggagactg cggagagttc tattgatcca gtggcctggg ttgaataagg actgggatcc    12480
aaagaagaag gaaaatattt ttttttagtt ttaaaaggac attaaatgcc ggctgcttgc    12540
aggaccagtc tccagacctg ctggacgacc acgtgattc attttgtttt cacttttatt     12600
tacatgtata ggtgttttgc ctgcatacgg tatgtgtgcc aagtgcctgc aaaggccaga    12660
agaggacatt agatccctg ggactagagt tacagacagt tgtgagcctc tatgtgttgg     12720
gaattgaacc tgggtcctct ccagtgctct taactgctga tccatctctc tagcccctga    12780
ttcaatatta taaatcagct tttagcacta aaacttggag gcagtctcct tctcaaagtc    12840
ctcagttttt agcctttcta ggaaaatcaa agatttggca gcattaaatc tgcctctcac    12900
gcctcatcag ttgcaagagc ccagtagtag gtgcctgact gacactcagc atcccacacg    12960
tggctcacta ggctcttgtg tcttatccac ctcctctatt taagagaaaa aaaaaaagac    13020
aggcttgtat gtatttgagg ctaacoctaa acaaaatact tagctgagca tggccttgaa    13080
cttttttttt cttttaaaga tttatttaat attatacata aatacactgt agctgtcttc    13140
agacgcacca gaagaggatg tcagatctca ttacgggtgg ttgtgagcca ccatgtggtt    13200
gctgggattt gaactcagga cttttgggag agcagtcagt attctcaccc gctgagccct    13260
ctcgccagcc cagccttgaa cttttgatcc ttctgcttct gcctcttgag tgctgggatt    13320
acaggcaggc accaccacgt gagttttatg tggtgctggg gatcaaacac ctcttgtggg    13380
gactcagcaa gctctgccaa cagagctaca ctgagctcca gtgaaatcct tccagcagac    13440
attcttcctc agccttgttt tgtggtgtct tttccttgag agtcttaagt acctaacact    13500
ggtctcctga tctcctcctg cctccctga tctcctcctg cctccctg atctcctcct      13560
gatcctcccc ctgtctccca ggtgttgtga ttgcagatgt gcagcatcct gcccagccac    13620
ttggcttttg tgtgacttct gtggttgtcc cttatttgta tttgaggtca gggcatagtt    13680
gcagctggat ggaacctgat ttctactcac cttcaggtc tcagcagggg ctgtgctgca     13740
tttgaggggc cttcttgctg ttctgaatta tccggtcatc cgatgtgatt atattatagt    13800
cacctgttct gtagctgcct tgctcactag acttcctcac tagtgaggta ggccctgtgt    13860
```

```
ctggctcaca gacttctctg ttcctcagac tctggctttg tgtctagcac ctaataagca    13920
cttcttaaat attctgatgt gttagttcct ttttggttgc tgtgacaaaa tacctgataa    13980
aagaaactta aggccgggca tggtggcgca tgcctttaat cccagcactt gggagacaga    14040
ggcaggcaga tttctgagtt caaggacagc ctggtctaca gagtgagttc caggacagcc    14100
agggctacac agagaaatcc tgtctcgaaa acaaaaaac aaacaaaaa tatatatata      14160
tatataaaga aaagaaaag aaacttaaga aggaagtttg gctcacaggg gcagaacaaa     14220
cttcccactg gagaagacgt gatggtagga gcctcaggta gctggttaga gagagggtca    14280
ctgcagcagg aggcgaagag ttgaatgttg gtcctgtctc gtgggatggt gccgcccgca    14340
ttcagggagg actgttctcc ttcagttcag catctctgga aatgtccttc cataagcttc    14400
caggggctgg gcttggacag ttctgaatct catgaggttg acaacataca ccattgcagc    14460
gagtgaattc agctgtccca gctcctctgt cctgtgtccc gcgctagctt cctgtgccct    14520
gacatggtgt tctctctcca ggtctccaga atgatcacaa ggcactgatg aagcaagtgg    14580
aggaggccct gcaccagctg cacgctcggg acaaagagaa gcaggctcgg acatggctg     14640
aagcccgaga gaggccatg aaccgcaggc tggcctccaa cagccccgtc ctgccccagg     14700
cctttgccag agtgaacagt atcagccccg gttccccagc cagtattgcg gtaatcttgc    14760
tggctctccc aaatccactc ctaacagtac tgagagttag gtagccctgg gcttcggagg    14820
cctgtcagaa ggcaaacccg tcctctcatt ctgtggctct gaattccttt attccttaa     14880
cacatgctgg ccagagcttg gtgtgcatag gggcagccca cggactcagg gagagaccta    14940
tggtgggacc atctgggaca cagtgtagaa agtgatccat gccccaaaga agaaaagagg    15000
tgttcttctt ggagccattt tcctggacac ggaaagaaaa aaaaatgaca agagcttaaa    15060
gcgatgtcag tgttctttga tagatcctag agcggcatta ctgtgatggg ctgctcctgc    15120
catgtgtgac ccaccaaagg acacagagga gtcacagagc tgcacattta gcaccgcagc    15180
caatttcaca gtattttat tggtgctgaa aagaagccag gcaggacttg ttgagcacca     15240
gtaattttgt ctgcacagat ctgcctgttc tgtgtctttg atgtgaagac agctgtatgc    15300
tgtgtgctct ctcactcggt ctgttcccag ggttcactca gggccgggtc acagatgaag    15360
ccttcattac gttttatggc tgagcaatat ccattatgtg ataggcatgt tcttgttggt    15420
cagttaatgg atgtctggat ctcttctgct ttggggctat tatacgtaat gcggcagtga    15480
atattcatgt agaagtttgt atgtggctgt gcatggatat tgaataccgt ggctgctgtg    15540
ggtggcacca ctgctctccg tgtgtgaccc tcgaggacaa gccacacatg gctcctggga    15600
agcacaaatg gattcttttc tttctttttt tctttagtat tttgaaacag ggtttctctg    15660
tgtagccctg gctgtcctgg aactccatct gtagaccagg ctggcctcag actcacagac    15720
atccacctgc ctctgcctcc cccattaaag acatgtgtca ccagacagaa ctggattctg    15780
aattcggatc ctacaaatca tcccaagact gggggataaa gggatggctc agttgttaag    15840
agcactgact gctcttccga aggtcctgag ttcaaatccc agcaaccaca tggtggctca    15900
caaccatctt taactagttt taggggatcc agttctctct tctggcctcc atgggcaact    15960
gacatacaag ttcacagaca ctcaagcagg caaaatgccc aaacacatta gataataaaa    16020
taaaataatt aaaaaaaata atcacaagct taaaaacggt cacaaggcca ctgggtatgg    16080
tggtatttt tcataatccc aactactgag gcagctgagt caggacttac ccaagtttgg    16140
gcaacttagg aaaattgtgt tttgaaatac gaaagactga ggatgtagct gttgggtaga    16200
```

```
gctcttgcct gggttggatt cctactgctg tgaacaattt ttaaaaagca aaataaagtc  16260
aagacatagg actacagact gcacgtcaac tctagtcaga gctggattcg caaccccag   16320
cgcctgacta gtcggcctct ggtgggtgtt tgttaaagag accagtaagt agtgtctgta  16380
atcttgggat ctgaaataaa aggaccacac tggttctggc tggccttagg cgtatggctg  16440
ctgcttaggg actcggagga ccaatgtttg tcttctcaaa aaaaaaaaa aaaaaaaaa    16500
aaaccaggcc taggctaaac tgcctccttg ccttgaacct gcctcagaag ctgcagaaca  16560
cagctcatgt cctcaaggtg tccactgggt acacctggac accatttgct aggtctgtcc  16620
tagaaggaac ctccagaatg aggcacctgc ctactccctg atcctactcg aggagttgaa  16680
atctttgacc tcgttactta gagcctgcca ttctttccct gtaggaaaca agctcttggt  16740
cttgccacag agttgtagat taagcggtac aaatgaccag aaaatgcatc caacctctcg  16800
ggttggcttt acattttct cctgtctta gggcctgcaa gtggatgacg aaattgtgga    16860
gttcggctcc gtgaacaccc aaaacttcca gtcagtgcag aacgtgggca ctgtggtgca  16920
gcatagcgag ggggtaagtc ggggtgccct ggcatccggg tgtcccacaa gccacagagg  16980
cctgctgctc gcacagatca ggggatagtg tggaagtcca ggagcagggg gccacagatt  17040
caggctctgg tccaaggatg acacagtttg cttaagggct ggatcactga ctccatcacc  17100
agggctccat ccccataaat tgcaccctc taaagcccag tctcctactc catcacaccg   17160
aggggccagt cagccagcct ttcagtatga gagctttcca gagggaagca ggagttcagc  17220
ccatagcgct gggtatctgt ctgtctgtct gggattttcc ggcccagaag ctgttggggg  17280
gatcctcact gctgacagca gtggtggtgc ctctctctct ccctggagag cttttttcttc 17340
catttgccac atttgtctta cacagctgag tcttttacac agttgatggc cctcctggtg  17400
ctcttgtcta aatccctcct ctgtgtcatc cagtaacagt aactaagcta gaagctgcct  17460
tattttggca catgccctgt tccctgcag ctgttattgg ggtccagttc tccatcactg   17520
ccttctctag accttgtgat gtttccagct tcacccaggg tggccgacca cgtacgtgtg  17580
cacgtggtca catgcttttc taggtggcac ctgtaaagaa gggtggccgg ctctgagaga  17640
tcgtgtatac ttgaggcgtc ttattctgtc tcaggctggc ctggatctca ctgtgtggcc  17700
taggatgatc ttgagccttc tggttgtcct tcctcccgtg cactggaagt acagtgtgcc  17760
tggccatgcc tgtttttatg taatacggag ctatctctct agcccgtgga tataggttct  17820
tcttttctg acacatatat ttcccaggaa tttattctat aattagttta gtgtaattag   17880
acacacatta ccaggccact tttcccccca aatggatagt agttgtcccg gtaccattta  17940
tcattatgaa tactttaccc actagtttac actgtcacct ctgttaatat cagatatatg  18000
ggtggtgttc tctttgttct gacccttttt ggagttgctt agaagaatcc atttgtccct  18060
gtctgctttc ctttaacacc ttgctataga gtgagtccaa ggaccatttg gaaagttggt  18120
aggccaagac cacagatgct tgtctgtctg gtacagtggg ctctcaacct tcctaacgct  18180
gccaccctt aatacagttc ctcatgttgt ggtggcccca accataaaat tacttttctt   18240
gctacctcat gactgtactt tggctactgt tagaaacagt aatataaaca tctgtgtttt  18300
cagatggtct caggggagcc ctgtgaagtg ggtgtctcac cccaagaagg ttacaaccca  18360
caggttgaga accactggtc tcgttggaca gctcagccat ccctgctggc tctgctggtt  18420
ctggcccaga ggcttctgtg agggccagcc aggacacctg cagacaccat ggccacccaa  18480
agggtccagc gaggctgtac atccacttcc accccatggt cggcccgagc cttcagttac  18540
tcatcctgcg gcttcataca ccacttgagt gcactacctc aggcagcgag agcagtgagg  18600
```

```
gggtcgcatc tcagaagatg cacagttatg tctttcttac ctcttagtga cttgctaggt   18660
ccagcccacg cctggggaga agggaattgg acctcctgaa gggaggcatg tgagaggact   18720
tggggcctat cattaaactg ccctccgagg gctccagcct ctctactcgc cctgccctca   18780
cttgtccagt ttgtggaagc tttccttgtg ttagcggtcc ctcatctctg tcatgtcttc   18840
ccagtgtttg tgtctgtggc tgtccagcct tgctagcctg ctgttcttca tcatctcagt   18900
gacatcatct ctgtgacagt gcgctgccac gcccagtgtg cgtatttgca gatgtgtttt   18960
taaagatgtc ctgttacatt ctgaattcag acccatggaa aacagaacca aagcacaaaa   19020
ttggcacaaa gtcttcaggt tcgtttcctg gcttcctttt agcttttttt caaaagactt   19080
actttgggga gtcccaatgt gcccgctgtc taaaagccaa gtggccatgg taatttgaaa   19140
gccacaccgc tgatctcagt cctgaccctc agggccctgc ttgagagtca ggagtctggg   19200
ttctcatcgt ctcttctgtg acttaaacaa acaaaaccc caggtctgtc tgtgctgtta   19260
gcatttcgga agtttccaat tttattacga ttctgctttt gtagagcaaa ctgtttctcat   19320
cagctttcct tccaaaagta tagtgtttgg atcaaacgcg tatattctca aagcgcaagc   19380
aatcttgatg ggaaaaaaat ttactgtctt gaccctaagg gtgtgtggtt cagtggcagg   19440
tcccttttca ggtgcccagt catgggtttg gtcaacaaaa gtgttgttgt tgttgttgtt   19500
gttgttgttg ttttgcaaca acaatttctg tctgccctgg ctgtcctaga gcacactatg   19560
tagacagact ggcctcacag agatccaatt acctctgcct actgagtgct gggattaaag   19620
gggtgcacca ccatgcccag cacactgttt tttgggtttt ggttttattt tatttattgt   19680
ttgtttgttt gtttgtttgt tgttatagc cctggctgtc ctggaactca ctttgttgac   19740
caggctgccc ttgaactcag aaatctgcct gcctctgtct cccgagtgcc gggattaaag   19800
gcgtgtgcca ccacacccag cttttggttt ttttaaatac atgtgtgtgc acactcgcat   19860
gcacctttat aataaaaaca atgcatattt agtttagcca caggaatgga gtaaattctc   19920
cattacatat tacaacatga gtattgaaaa cataatataa agtgaaagag accaaacagg   19980
aggccataca attcctcaac gaagttgtcc taaaaagcag atctagaaag ctagaaggga   20040
gattggctgg tggttgctgg gcgggagggt gagggtgagg accatgtgct gatggtcttt   20100
tggatgatgc agacagaccc tctgcagtta ggaggtggtg atgggtctga gagcaggaga   20160
cccactgagc cctgctttac tgtatataaa ttgtgtctca gtaagaagcc tactgcatat   20220
ttatgtcaca tacaaattca cattgcaaaa atgtttaaag tgaaaatcaa agcactgtgt   20280
ctgtctctct ctgtaactcc ctcccctgcc ctccctgcc ctccctgcc ctccctgcc   20340
ctccctgcc ctccctccc ctccctgcc ctccctccc ctgccctccc ctccccatgt   20400
gtgcttactt ctggactgag ggctggggtc cagcattgaa caaaaatcaa agagagggac   20460
cttgctttga gagcagacat gagttcagta gttccggacg accaattttta tatcctgacc   20520
agagttgaca ggagaagcct tcgcaggaga gctggaggag agcagtgggg tcctggtgta   20580
gtttggggta gaaggagtgt tcctaagtac tgaccctcgg agtaaggact gacccttggt   20640
gtgtatagaa actgatctgt ggagtggcca ctagagagcg cccttcagct ggttctcagg   20700
ccttggaggc aggaggatca aagcagccag attgttgatt ggtgctcaga accatgaatc   20760
agggaggtga ccagggccag gccatgcagg gccagcctcg gagtccctta caaagaaaat   20820
gatgactttt ttttcctggg gagcagcagg gagctgctgt accacccaaa gctggggaga   20880
gtttgtctca gagattgcat ggtgctagtg agagaacagg tttgggggtg tgtccagcat   20940
```

```
gtgggtctgt gtcctcatag ggtctcaagt aggaatcaag tgtcagatgc cggaacttaa      21000
ggagacagtt ctcattcaag tcgacatagt tcctaccatg cttttaccct cccaccattt      21060
ttaatttctt catggttcat taatgctggg gcccaaagtg gtcaatttca tggtcagaaa      21120
atggtatctc cacatactga gtcctcttga gtggaaggaa gcagaggctg gaatgacctt      21180
ctttgccttt cagaagcccc tgaatgtgac ggtgatccgc agaggagaga agcaccagct      21240
cagactgatt ccaacccgct gggcaggaaa aggactgctg gggtaatgct gggctctgct      21300
tcccatgctc tcacaccctg gcacccacag agagtgcgct cagatagagc tggggatgct      21360
ggtacccata gagagtgtgc tcagatagag ctggggatgc tggtacccat agagagtgtg      21420
ctcagataga gctgaggatg ctggtaccca tagagagtgt gctcagatag agctggggat      21480
gctggcaccc atagagagtg tgctcagata gagctgagga tgctggcacc catagagagt      21540
gtgctcagat agagctgggg atgctggtac ccatagagag tgtgctcaga tagagctggg      21600
gatgctggca cccatagaga gtgtgctcag atagagctgg ggatgctggc acccatagag      21660
agtgtgctca gatagagctg aggatgctgg tacccataga gagtgtgctc agatagagct      21720
ggggatgctg gtacccatag agagtgtgct cagatagagc tggggatgct ggcacccata      21780
gagagtgtgc tcagatagag ctgggaatgc tggtacccat agagagtgtg ctcagataga      21840
gctgaggatg ctggtaccca tagagagtgt gctcagatag agctggggat gctggtaccc      21900
atagagagtg tgctcagata gagctgggga tgctggtacc catagagagt gtgctcagat      21960
agagctgagg atgctggtac ccatagagag tgtgctcaga tagagctggg gatgctggca      22020
cccatagaga gtgtgctcag atagagctga ggatgctggc acccatagag agtgtgctca      22080
gatagagctg gggatgctgg tacccataga gagtgtgctc agatagagct ggggatgctg      22140
gcacccatag agagtgtgct cagatagagc tggggatgct ggcacccata gagagtgtgc      22200
tcagatagag ctgaggatgc tggtacccat agagagtgtg ctcagataga gctggggatg      22260
ctggtaccca tagagagtgt gctcagatag agctgggggat gctggcaccc atagagagtg      22320
tgctcagata gagctgggaa tgctggtacc catagagagt gtgctcagat agagctgagg      22380
atgctggtac ccatagagag tgtgctcaga tagagctggg gatgctggta cccatagaga      22440
gtgtgctcag atagagctgg ggatgctggc acccatagag agtgtgctca gatagagctg      22500
ggaatgctgg tacccataga gagtgtgctc agatagagct ggggatgctg gtacccatag      22560
agagtgtgct cagatagagc tggggatgct ggcacccata gagagtgtgc tcagatagag      22620
ctgggaatgc tggtacccat agagagtgtg ctcagataga gctggggatg ctggtaccca      22680
tagagagtgt gctcagatag aacactcagg tccactaaag gatagccatc cccagagtgc      22740
agaaactggt ggttaataac cgtttttatg aatgaggcta caggcaagag tcctcaggtc      22800
acctgagagt ctcacttctc aatccctggg cattgtcttt aagagaaaga aaagtgacca      22860
gtgctcagca ggtaaaggtc tttctgcaaa tctctgacct gagtcagatc ccaggactca      22920
cttggtggaa ggagagaact gactcctgca ggctctgcgt gccacacacc cagactctct      22980
tatatacaca atgaaacact gtaaaatata cattaaaaaa tacaattcta gccgggcagt      23040
ggtggcgcac gcctttaatc ccagcactcg ggaggcagag gcaggtggat ttctgagttc      23100
gaggccagcc tggtctacaa agtgagttcc aggacagcca gggctacaca gagaaaccct      23160
gtctcgaaaa aacaaaaacc aaaccaaacc aaaaccaaaa ccaaacagtc tttaaaagag      23220
aagaagtgtt cacctgcagg tttcctaggc tggagctgtc aggcttgagc cggtctctgt      23280
tttctcttac agctgcaaca ttattcctct ccagagatga ctgtttcctg ggatctgcct      23340
```

```
gcaggaagct gcctcagctg gccccgtgct tgggcctgga ggcgtttcct cgttctctag    23400
gctcccttaa gtgtaaggat ctggagaaga atggtcgaag cctgggcatc gaggtggaag    23460
agacgctttg gctgcctgat gtaatctctc tgggttgagg cattattaaa agtgtgattt    23520
gtgcctagct acgtcttgtg caaattaggc catagcctgt ctgggaattc tctagattat    23580
gagccagtga gtggggatga ctctggcgag taatgatttg atgtcatttt ccttttggag    23640
acggactcag tgtgtaatcc tgactatcct ggaattccct gtgtagacca ggctggcctt    23700
gagctgacag agatcccccct gcctctgcct cattagtatt gggatgagag gcatatactg    23760
acatggctgg ctagactctg aggaatatgt attatacata tataatttat acttattttt    23820
gagaatttcg tacatgcaca tagtacattt ctatatttcc tgtcatctca agtccctctc    23880
agacctcccc tcgtacccac ttcccaggtt cttgccctct tttgttttt tcttttttaa    23940 ataaataacc tactaagtgc catttgtgct gtcagtatat tcatggtgtg ggatcttcca    24000
ctggaggaat gtggtcaacc ttccagagac cacacccta acctccacag gacttgagta    24060
cccctacttt ttcttggaag cagggtctca tgtagcccag tccagcctca gatttgcctt    24120
gaagctgaag atgttctctt ctgctgtctc tccctccaat gtccaactgc agtatcaccc    24180
accgcctagg ggtgggggct tgctggagac cggatctcac aagttcagac tggcctggag    24240
ctcagtgtac ccgcactggc cttacccttg ggatcttgct gccctggtct cctggtatta    24300
tagtgtatgc caccaaacct tgttacaggt tagagaaact gtcagataaa gccagtcttg    24360
tagctgtgtg attgtgacca ctgtcagtcc caccaggatg ccctgtgagc tcacagccaa    24420
gcccaggagg agttgggaag gaagtcctgc gaagcaaacg agttcctggg ccgcagtccg    24480
gttgattctt gggtgggaaa ctgaaagccg gagctcagac tctaggcaag tgtccctccg    24540
tgggctgagc agctggcagt ctctaccctg gagcagtgct ttgagagcct gatgcatcct    24600
ctgaggctga ggctgtggag tcaccgtagc cccattaaga aatcagcaaa gaccaggtgt    24660
ggtggctcaa acgtttttaat cccagcactc aggaggcagg ggcaggcgga tttctgagtt    24720
aaggccagcc tggtctacag agtgagctcc aggacagcca aggaaggcta cacagaaaaa    24780
ttctgtctca aaacaaaatt tgcaaaggtc acaggtcacg aggccttgca ggttacccag    24840
tatgatattg gcttcctctt cagtaaccca ctggaaacca gcaagcttcc tttacttcta    24900
cagtaaaaga ccccgcagat gggcctgatt tggcttttat agttgagcct ccccaccggg    24960
cggtggtggt gtacaccttt aatcccagca ctcaggaggc agagagaggc aggcagatct    25020
cagagtttga ggctagcctg gtctacagag tgagttccag gacagccagg gctacacaga    25080
gaaaacctgt atggaaaaca aaataaaaac aaatttaaaa aacaaacaaa attgagcctc    25140
ttgggatcag catgggaagc taaggagtgc ttgcctgttg ctgaggtgac tgcattgatg    25200
gatgctgctt tgctgcttcc tttcatattc tgtcttttga gatggtaaaa ttggtgtggg    25260
tgactctgtt tttcttcctt tctccatgtg ccccagttat ctcccagtt gcctcccgtt    25320 tctgttttgg atgtctggtc ctttctacaa ggaagcttgc gtccttgcat tggatttccg    25380
cgggatggag gcagagacca gctttgtctg atggcagtca gtactgacat gtgcttcctg    25440 cttttgagtcc gcacacacaa ctcaaaagcc tcccctaagc tgcttcatcc agacagcctc    25500
acgccacccc tctcccgtag ccagactggc tctgtttact agggtttgct gtttcagttg    25560
tgggttataa atccaagtat tttccagact ctttataagt ctcacactgt aataaaacac    25620
agcttgtacc attcaagaga taggcatgtg atcaccagca ctggggcgtg gtgtggtggt    25680
```

```
ggacttgtcc atagtcattc atatcctctc taagaggctg caataggcct tgcactgctc    25740
agaaagccac ctttgggctc ccctatgact tgcttcaaca ggaataacgc taatggattt    25800
tttttttttt tttttaaag atttatttat tattatatgt aagtacactg tagctgtctt    25860
cagacactcc agaagaggga gtcagatctt gttacggatg gttgtgagcc accatgtggt    25920
tgctgggatt tgaactctga accttcggaa gagcagtcgg gtgctcttac ccactgagcc    25980
atctcaccag ccccaacgct aatggattta accaagctgg gcttgcgtgg taacagcaag    26040
atggtgcact ctccacataa cttcaatccc agtttactaa acttctctgc atgctgtgtc    26100
ctggtgagaa ggtgggcagt tgtgtgtaac acctgtgagg ccaaaaaaat tgggttttag    26160
cactgggaga attttattaa ctgcttcata ccacttcttg cctggcttcc tggagaggca    26220
tgagcacaca tctgttcacc ttgcactgat ggcaaactga aggaacccac ccaaatcagc    26280
cctgtgagcc cgtgagcctc ctggggttgc ttagaggctc tctcggcact atggatatac    26340
aactcgcagg cagctagctc cactgaaatc tcctttcaca cagtaaagtc ttgtgtagtc    26400
caggctgact gaacagaccc ttctggcttc atctgcctag ttctggattt gtaggtggga    26460
catcatgcct ggcccaacgt ctagtttttt gttttgtttt gttttttaaga tttatttatt    26520
tatttattac atgcaagtac actgtagctg tcttcagacg ccccagaaga gggagtcaca    26580
tctcattacg gatgattgtg agccaccatg tggttgctgg gatttgaact cgggaccttc    26640
ggaagagcaa tgagtgatct taaccactga gccatctatc cagcccccaa cgtctagttt    26700
ttatttatgt atttatttat tcattcaatc atccgttcat tcatttattt attttactgc    26760
ttttatgacc tccggaaggg cttcctgaca cttgagggaa ccccaccacc caaccccac    26820
cgagttttt gagcaggtct ccgtttcccc tcccctacga atgcccaatc tggagaaaat    26880
aactgcaaac actactttcg ttacatcttg tccaactta ggaaagtcag aatcgccagt    26940
gtaggggagt agctcttgtg gaagtgtcct ttaggaaaaa gctgtggcgt gagctgctag    27000
cccggcaggg ggcaggctgg tccgcctcga ggccgctttc tgggcacgtg attaccatcc    27060
tgcttccttg ctttcctgcg actagccgtt gccataggga cggagcttgg ttggcaaccg    27120
tcactaggga gtatggacag gagccctgg aggtctcttg ggatttcccg aggctggacg     27180
acccaaggct tttgagaaaa gaagtgggag cgtccctgta agtgcgaagt ggagggtgcg    27240
gctcgggttg gggtccgggc caggcagcgg caagggtgtg ggacctggga ggtccccagg    27300
aaaagaaact ggtggctcct ggacctcgtg gtaggataga cttgcgcacc tgtggcattg    27360
cccccgcctg ggtgtggaaa atgtcaaagt ggcattttt tcaaacaaaa gaactaaatt     27420
ctagctctgt cgtaagtcgt gcctcccagg gccacaaact ttttcatttc cttttccttt    27480
tccttttcct tttccttttc cttttccttt tcctttttcct tttccttttc cttttccttt    27540
tccttttcct tttcctttcc ttccttcctt ccttccttct ttctttcttt cttttttag    27600
aaagattgtg ctggcctaag aactcgagtg atcctcctgt ctctacctcc tgaatcgcag    27660
tattacagac atgggcctag ccccctgctc ccaaactctt gcttcatgta ggtgcaaaat    27720
gagagaatgt atcagaggaa ttaaatttt ttaaaaatg attttatgtg tgagactgtt      27780
ttgtctgcat gtatgtatgt gtaccaccta tgaagttccc gcagaataca gaagagggtg    27840
tcagatcccc tgaaactcaa gttacttatg gttctgagcg atcgtgtcat ggctgggagt    27900
caaacctggg tcttctgaaa gggcagccag agtgctctta atcactgagc catctctcca    27960
gcccagaatt aactttcttt ctttctttct ttctttcttt                           28000
```

```
<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
tgatccgcag aggagagaa                                               19

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
gatcccagga aacagtcatc tc                                           22

<210> SEQ ID NO 14
<211> LENGTH: 24
<212> TYPE: DNA
<213> ORGANISM: Artificial Sequence
<220> FEATURE:
<223> OTHER INFORMATION: Probe

<400> SEQUENCE: 14
aggactgctg ggctgcaaca ttat                                         24
```

PSMD9 INHIBITORS FOR THE TREATMENT OF HEPATIC LIPID DYSREGULATION

CROSS-REFERENCE TO RELATED APPLICATIONS

This application claims the benefit of provisional application No. 62/619,480 filed Jan. 19, 2019 and PCT application no. PCT/AU2019/050033 filed Jan. 21, 2019, both of which are hereby incorporated by reference as though fully set forth herein.

This invention was made with United States government support under Grant Number HL028481, awarded by the National Institutes of Health. The United States government has certain rights in the invention.

FIELD

The specification relates generally to the post-genomic identification of therapeutic targets and agents. In particular the specification relates to modulatory agents and methods for preventing or treating metabolic disorders such as fatty liver disease that are associated with dysregulation of lipid homeostasis.

DESCRIPTION OF THE ART

Reference to any published document in the specification is not, and should not be taken as, an acknowledgement that this publication forms part of the common general knowledge in any country. Bibliographic references are listed at the back of the specification.

The cross referencing of large datasets using a set of common biological samples, often referred to as systems biology, is an approach that has been utilised for almost two decades in an attempt to unravel the complexities of pathological traits in model systems. This approach has proven to be extremely valuable in identifying candidate genetic components and individual genes that maybe causative to a given trait. However, due mostly to technological limitations many of these pioneering studies were performed at a time when it was not possible to accurately quantitate arguably the most biologically relevant molecules, the proteome. Recent advances in proteomics technology have since demonstrated that it is now possible to quantify more than 10,000 proteins in a complex tissue such as the liver (Azimifar et al., 2014), which paves the way for systems biology approaches that now incorporate quantitative proteomic datasets. Indeed, two recent studies integrated such quantitative proteomic analyses with several other "omics" datasets from the livers of genetically diverse mouse strains, which elegantly highlighted both the power of these analyses and the astounding complexity of metabolic signalling in the liver (Chick et al., 2016). This was particularly true with regards to the apparent disconnect between transcriptional and translational control of liver metabolism. These studies, together with others (Wu et al., 2014), suggest that there is a significant lack of association between mRNA and protein expression for a set of given genes in the liver, where up to as many as 50% of proteins lack any statistical association with the abundance of their corresponding mRNA transcript. This finding alone suggests that prior studies aimed at identifying causal pathways in complex pathological traits using only transcriptomics, may well have had only 50% of the resolution of studies that incorporate proteomics data to their analysis. Furthermore, integration of other "omics" technologies such as lipidomics to investigate the contribution of proteome diversity on lipid metabolism in the liver has not been performed. Here, a trans-omics approach has been used that incorporates genomics, henomics, lipidomics and proteomics from the livers of 107 strains of mice (307 mice in total) from the UCLA hybrid mouse diversity panel (HMDP), to dissect the contribution of genetics to the propensity of eight week old male mice to display characteristic features of hepatosteatosis on a normal chow diet.

The HMDP is a panel of genetically diverse inbred mouse strains that encompasses the genetic variability of several common mouse strains as well as the BxD hybrid lines (Ghazalpour et al., 2012). The power of the HMDP has been demonstrated in several prior studies that have identified novel causal pathways in the development of complex metabolic traits including atherosclerosis, obesity, hypertriglyceridemia and type 2 diabetes. Accordingly, the HMDP is a proven and powerful panel from which to identify contributing factors that associate with the development of complex traits. It was proposed by the inventors to utilise the HMDP as a tool to identify signalling pathways that contribute to hepatosteatosis.

Hepatosteatosis, which encompasses non-alcoholic fatty liver disease (NAFLD), is characterised by an accumulation of lipids including triglycerides in the liver, a condition significantly influenced by genetics and environmental factors such as obesity and diets high in fat. NAFLD is associated with an increased risk for cardiovascular disease and metabolic syndromes such as insulin resistance, glucose intolerance and type 2 diabetes. Furthermore, approximately 15% of patients with NAFLD progress to a more serious complication known as non-alcoholic steatohepatitis (NASH), that manifests as fibrosis and inflammation in addition to NAFLD (Harris et al., 2017). NASH is a significant risk factor for the development of cirrhosis and hepatocellular carcinoma and it is primarily for these reasons that NAFLD is predicted to become the leading cause of end-stage disease and liver transplant in Western society over the next two decades Steatosis or fatty liver involves the accumulation of lipids in hepatocytes and diminished hepatocyte function and is thought to develop in response to hepatocellular insults, such as drugs. The role of lipids in hepatic pathology and hepatotoxicity is described for example in Mota et. al., *Metabolism* 65(8):1049-1061, 2016 and Musso et. al., *Nature Reviews, Drug Discovery* 15: 249-274, 2016.

There is growing evidence of the important roles of key enzymes in de novo lipogenesis (synthesis of new lipids—DNL) and their link to fatty liver diseases in man Indeed, DNL assessments such as by stable label techniques or fatty acid profiling is recognised as providing an instrumental marker of drug efficacy for novel NAFLD drugs and response to nutraceutical agents. In a review article by Tacer and Rozman *J. lipids* 2011 783976, the authors highlight the importance of genes in the DNL pathway in NAFLD and illustrate how their intervention is associated with reduction in NAFLD. Other relevant publications include: Jiang et al., *J Clin Invest.* 2005 April; 115(4):1030-8. Epub 2005 Mar. 10 showing inhibition of Stearoyl-CoA desaturase-1 (SCD1) reduced adiposity in mice. See also Xing Xian Yu et al. *Hepatology;* 42:362-371, 2005 who demonstrate antisense inhibition of acyl-coenzyme A:diacylglycerol acyltransferase 2 (DGAT2) reduces hepatic tryglyceride (TG) content and steatosis in mice; and Singh et al *PloS One* 2016 0164133 who showed that fatty acid synthase inhibitor, Platensimysin reduced DNL in lean and type 2 diabetes (T2D) monkeys and lowered plasma glucose.

There is an ongoing need to identify new strategies to manage defects in liver lipid metabolism, such as those found in fatty liver conditions that can lead to a body wide breakdown in homeostasis and disease development.

SUMMARY

As determined herein, dysregulated or elevated levels of PSMD9 either through over expression or as observed in mice models produce a signature of elevated lipid synthesis enzymes and pathological lipid species instrumental in the development of hepatic lipid dysregulation and fatty liver.

As determined herein, overexpression of PSMD9 leads to upregulation of proteasome and lipid signally pathways and an increase in pathological lipid species that are directly linked to fatty liver disease and insulin resistance. This indicates that PSMD9 is not elevated as a result of the presence of pathological lipids in the liver or blood.

As determined herein, administration of down modulators of PSMD9 is effective to prevent or treat the accumulation of pathological lipids in the subject. Specifically down modulation of PSMD9 expression prevented or reduced pathological lipid accumulation at least in the liver and plasma of a subject.

As determined herein, inhibition of PSMD9 with antisense oligonucleotides caused a significant reduction in key enzymes in the DNL pathway (including ACACA, ACACAB, FASN, SCD) in mice on a high fat (Western) diet and a significant reduction in key pathological lipids linked to fatty liver disease including diacylglycerols (DGs) and triacylglycerol (TGs).

Reference to "pathological lipids" includes one or more lipid species from a lipid class selected from acyl glycerols, diacylglycerol (DG) and triacylglycerol (TG), phosphatidylcholine (PC), phosphatidylethanolamine (PE), cholesteryl ester (CE) and ceramide (Cer) or their variants (e.g., dihexosylceramide (DHC)).

As determined herein, inhibition of PSMD9 in mice exposed to a Western diet for four weeks caused a reduction in markers of fibrosis (Vimentin, Smad7, collagen), ER stress (CHOP) and blood glucose. This indicates to the skilled person that inhibition of PSMD9 will provide a useful treatment or prophylactic for NASH and T2D.

Based upon the experimental results disclosed and enabled herein, PSMD9 inhibition is associated with a reduction in the following pathologies induced by a Western diet; hepatic steatosis, pathological lipid accumulation, de novo lipogenesis (DNL), hepatocyte ballooning, inflammatory response, hepatic fibrosis, endoplasmic reticulum (ER) stress and elevated blood glucose.

PSMD9 which has previously been identified as a transcriptional regulator and receptor. PSMD9 is also referred to in the scientific literature as 26S Proteosome Regulatory Subunit p27, Rpn4 and Bridge-1. It is known to interact with PSMC3 as part of a transient complex formed during the assembly of the 26S proteasome. As determined herein PSMD9 is a key regulator of the liver lipidome whose modulation permits favourable in vivo lipid remodelling (i.e., reduction in pathological lipid accumulation).

Accordingly, in one embodiment the present description enables a method of treating a subject suffering from hepatic lipid dysregulation or at risk of suffering from same, comprising administering a PSMD9 inhibitor to the subject.

Accordingly, in one embodiment the present description enables a method of treating or preventing hepatic lipid dysregulation in a subject. In one embodiment, the method comprises administering to a subject in need thereof a PSMD9 inhibitor comprising an agent that inhibits PSMD9 expression or PSMD9 polypeptide activity. In one embodiment, administration is for a time and under conditions sufficient to reduce pathological lipid species in the liver. Various diseases and conditions are associated with hepatic lipid dysregulation, in particular, fatty liver, fatty liver disease, NAFLD, NASH, T2D and insulin resistance. In one embodiment, the PSMD9 inhibitor selectively binds to PSMD9 nucleic acid and suppresses PSMD9 expression. In one embodiment, PSMD9 inhibitors are membrane penetrating to enable binding to PSMD9 nucleic acid and PSMD9 polypeptide.

As used herein, the term "subject" means any animal including humans, for example a mammal Exemplary subjects include but are not limited to humans and non-human primates.

For example, the subject is a human Reference to a subject includes a cell or tissue of the subject. In one embodiment, the subject has been identified as suffering from fatty liver or hepatosteatosis or as at risk from fatty liver or hepatosteatosis. In one embodiment, the subject has been previously tested for pathological lipid accumulation known in the art or as disclosed herein. Testing may take place on a biological sample from the subject. A biological sample includes a tissue sample including blood, plasma or serum from a subject. Other forms of testing are instrumental such as by sonography, computer tomography, magnetic resonance imaging and the like. In one embodiment, a cell of a subject is a cell of the liver.

The term "hepatic lipid dysregulation" includes early stage lipid dysregulation (fatty liver) such as found in subjects with elevated levels of pathological lipids. As determined herein this early stage may be identified by assessing the level of pathological lipids (e.g., one or more of DG, TG, PC, PE, CE and/or DHC). The term also encompasses fatty liver disease also referred to as hepatosteatosis and non-alcoholic fatty liver disease and in some embodiments to its pathological sequalae.

A reduction in lipids, lipid species and pathological lipid species may be 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% relative to a suitable control. In some embodiments, reduction is 20%, 30%, 40% 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, 97%, 98%, or 99% or 100% or more, relative to a suitable control.

In one embodiment of the method the hepatic lipid dysregulation is selected from the group comprising; fatty liver, NAFLD, NASH, metabolic syndrome, T2D, and insulin resistance. In some embodiments, the subject has been diagnosed with a condition associates with hepatic lipid dysregulation selected from the group consisting of fatty liver, NAFLD, NASH, metabolic syndrome, T2D, and insulin resistance.

In one embodiment, the PSMD9 inhibitor is or comprises a peptide, a peptidomimetic, a small molecule inhibitor, a polynucleotide, or a polypeptide molecule.

In accordance with the present description, the PSMD9 inhibitor reduces the accumulation of pathological lipid species in the subject. In one embodiment, the subject is assessed and determined to exhibit prior to treatment, elevated levels relative to a control of pathological lipid species in the liver or plasma. In one embodiment, the PSMD9 inhibitor is administered in order to reduce the accumulation of pathological lipid species in the subject. In one embodiment, the PSMD9 inhibitor is administered in order to reduce the accumulation of pathological lipid species in the liver or plasma of a subject.

In one embodiment, the PSMD9 inhibitor is in the form of a pharmaceutical or physiological composition comprising the PSMD9 inhibitor as the active ingredient.

In one embodiment, the PSMD9 inhibitor is in the form of a pharmaceutical or physiological composition comprising the PSMD9 inhibitor and a suitable diluent and/or carrier. The agents described may be in the form of a composition or kit comprising same.

In one embodiment, the PSMD9 inhibitor is an inhibitor of PSMD9 expression.

In one embodiment, PSMD9 activity is determined by evaluating the level or activity of a protein whose expression is correlated with PSMD9 expression in a liver cell as determined herein. In one embodiment, the level or activity of PSMD9 in blood, plasma, serum from a subject is determined.

In one embodiment, PSMD9 activity is determined by evaluating the level of PSMD9 polypeptide in a cell or tissue including blood, plasma or serum, of a subject.

In one embodiment, the peptide is a phosphopeptide or phosphomimetic.

In one embodiment, the polypeptide comprises an anti-PSMD9 antibody or an antigen binding fragment thereof.

In one embodiment, the PSMD9 modulator is a polynucleotide. Polynucleotide sequences include oligonucleotides.

Oligonucleotide modulators are known in the art and/or are as described herein. In one embodiment, oligonucleotides comprise sequences complementary or substantially complementary to at least one PSMD9 nucleotide sequence. PSMD9 nucleotide and amino acid sequences are known in the field, include variants including variants for multiple species, and are identified in publically available sequence databases. Illustrative PSMD9 sequences are described in the sequence listing.

In one embodiment, the polynucleotide is an antisense oligonucleotide.

In one embodiment, the antisense oligonucleotide is about five, six, seven, eight, nine, 10, 11, 12, 13, 14, 15, 16, 17, 18, 19, 20, 21, 22, 23, 24, 25, 26, 27, 28, 29, 30 nucleotides or more in length.

In one embodiment the PSMD9 modulator is an inhibitory oligonucleotide selected from an isolated or synthetic antisense RNA or DNA, siRNA or siDNA, miRNA, miRNA mimics, shRNA or DNA and chimeric antisense DNA or RNA. In one embodiment, the inhibitory RNA is selected from a shRNA, gRNA siRNA, miRNA, miRNA mimic or chimeric antisense RNA. PSMD9 inhibitors may comprise or encode an antisense, siRNA, shRNA, miRNA, ribozyme, DNAzyme or other nucleic acid molecules. Such agents are typically isolates, or non-naturally occurring and are made synthetically or recombinantly PSMD9 inhibitors may be conjugates or chimeric molecules comprising mixtures of the molecules described herein.

In one embodiment, the polynucleotide is a vector for the expression of the PSMD9 modulator.

In one non-limiting embodiment, the modulator is a dominant negative modulator comprising PSMD9 or a non-functional variant thereof that does not upregulate the level of pathological lipids in the subject or liver. In another embodiment, the modulator is a chemically modified RNA encoding a non-functional variant.

In one embodiment, the vector is a viral vector or a non-viral vector.

Any suitable viral or non-viral vector may be employed. An adenoviral associated or non-viral vector, for example, is useful for administering to the liver.

In one embodiment, the hepatic lipid dysregulation comprises upregulation of pathological lipid species as described herein.

In one embodiment, the description enables the use of a PSMD9 inhibitor in the manufacture or preparation of a medicament for use in the treatment or prevention of hepatic lipid dysregulation in a subject.

In one embodiment, the description enables a PSMD9 modulator for use or when used in the treatment of hepatic lipid dysregulation in a subject.

In one embodiment the hepatic lipid dysregulation is fatty liver disease (steatosis) or non-alcoholic or alcoholic fatty liver disease.

In one embodiment, the PSMD9 inhibitor reduces markers of NASH or T2D or insulin resistance, such as inflammation, fibrosis, ER stress or glucose levels in the subject.

In one embodiment, the method further comprises measuring the level of one or more lipid species in a sample from the subject at a time such as before, during and/or after treatment to determine the effect of the PSMD9 inhibitor in lowering pathological lipid species or reducing lipid abundance in the subject.

In one embodiment, the method further comprises measuring one or more markers of inflammation, fibrosis, ER stress, T2D or insulin resistance at a time such as before, during and/or after treatment to determine the effect of the PSMD9 inhibitor in the subject.

In one aspect, the present description enable a PSMD9 inhibitor for use in treating or preventing or preventing progression of fatty liver, fatty liver disease, NASH, T2D and or insulin resistance in a subject in need thereof.

In one embodiment, there is provided a pharmaceutical composition comprising a PSMD9 inhibitor and a pharmaceutically acceptable carrier and/or diluent for use in the treatment or prevention of metabolic syndrome, fatty liver, fatty liver disease, NASH, T2D or insulin resistance in a subject.

In one embodiment, there is provide the use of a PSMD9 inhibitor in the manufacture of a medicament for use in the treatment or prevention of a condition selected from the group comprising metabolic syndrome, fatty liver, fatty liver disease, NASH, T2D or insulin resistance in a mammalian subject.

In one embodiment, the description enables a method of reducing pathological lipid species in a subject comprising administering a PSMD9 inhibitor to thereby reduce pathological lipid species in the subject. In one embodiment PSMD9 inhibition of PSMD9 expression of PSMD9 protein level or activity includes at least 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, 97%, 98%, or 99% or 100% proportionately less expression, level or activity in a treated cell compared to a suitable control, or at least 1.5 fold, 2-fold, 3-fold, 4-fold, 5-fold, 6-fold, 10-fold, 20-fold, 50-fold, 100-fold, 150-fold, 1000-fold, or 10000-fold or more suppression of PSMD9 expression or activity in a treated cell compared to a suitable control. In another embodiment the description enables a method of reducing pathological lipid species in the liver of a subject comprising administering a PSMD9 inhibitor to the subject thereby reducing pathological lipid species in the liver of the subject.

Reducing pathological lipid species includes reductions of at least about 10% to about 50% in the liver and/or plasma. Reductions or reduced accrual of particular pathological lipid classes or species may be monitored in subjects with fatty liver.

In one embodiment, subjects administered PSMD9 inhibitors display lower levels of pathological lipid species in the liver and/or plasma, and markers indicating one or more of reduced inflammation, reduced ER stress, reduced fibrosis and reduced blood glucose.

In one embodiment, PSMD9 expression inhibition is mediated by oligonucleotides that are complementary to a PSMD9 polynucleotide sequence determined from a mammalian species. Illustrative nucleotide sequences are set out in SEQ ID NO: 1, 3, 6 and 7. Genbank Accession no NM-002813 disclosing a human sequence and sequences of published variants and isoforms thereof are available. In one embodiment In one embodiment the antisense sequence is complementary to any of the published nucleotide sequences for PSMD9 or has at least 80% sequence identity thereto.

In embodiments where the PSMD9 inhibitor is a polynucleotide, in one embodiment the polynucleotide is a modified oligonucleotide targeting PSMD9.

In one embodiment, the compound is single-stranded.

In one embodiment, the compound is double-stranded.

In one embodiment, the modified oligonucleotide comprises at least one modification selected from at least one modified internucleoside linkage, at least one modified sugar moiety, and at least one modified nucleobase.

In one embodiment, the modified oligonucleotide comprises: (a) a gap segment consisting of linked deoxynucleotides; (b) a 5' wing segment consisting of linked nucleosides; and (c) a 3' wing segment consisting of linked nucleosides; wherein the gap segment is positioned immediately adjacent to and between the 5' wing segment and the 3' wing segment and wherein each nucleoside of each wing segment comprises a modified sugar.

Any embodiment herein shall be taken to apply mutatis mutandis to any other embodiment unless specifically stated otherwise.

The above summary is not and should not be seen in any way as an exhaustive recitation of all embodiments of the present disclosure.

BRIEF DESCRIPTION OF THE FIGURES

Some figures contain colour representations or entities. Coloured version of the figures are available from the Patentee upon request or from an appropriate patent office. A fee may be imposed if obtained from a patent office.

KEY TO SEQUENCE LISTING

Figure 1:
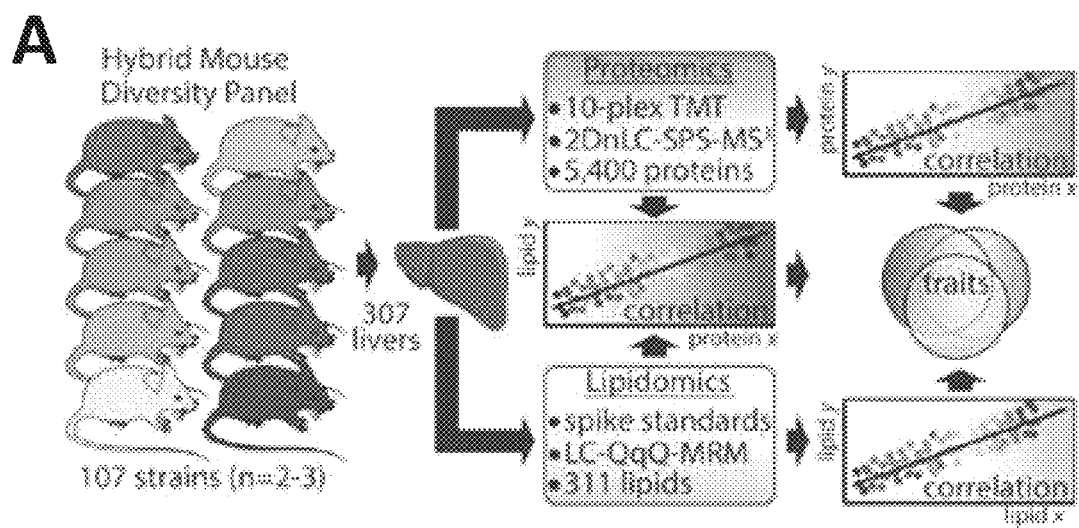
FIG. 1 illustrates a proteomic and lipidomic analysis of the Hybrid Mouse Diversity Panel (HMDP) (A) Overview of the trans-omic analysis of 307 livers from 107 strains of the HMDP (n=2-3 from each strain). Following proteomic and lipidomics quantitation, bioinformatics analyses identified correlations between and within the datasets to define proteomic and lipidomic signatures across the strains. (B) Percent coefficient of variation (CV) of the proteomic (blue bars) and lipidomic (pink bars) analysis highlighting technical, intra-strain (within strains), and inter-strain (between strains) variation. (C) Unsupervised hierarchical clustering of liver proteomics data from the HMDP over 107 strains (n=2-3; 307 individual livers). (D) Scatterplot highlighting inter-strain variation in protein abundance in the HMDP compared to the Diversity Outbred (DO—top panel (Chick et al., 2016)) and BXD (bottom panel (Williams et al., 2016)) cohorts of mice. (E) Box-plots of the average (all livers, Log 2 µmol/µmol PC) of lipid species from seven classes of lipid including diacylglycerols (DG) and triacylglycerols (TG) and the sphingolipids (Cer=ceramide, dhCer=dihydroceramide, MHC=monohexosylceramide, DHC=dihexosylceramide, GM3=GM3 ganglioside). (F) Variation of total triacylglycerol (bars) and diacylglycerol (dots) abundance across the strains in the HMDP (µmol TG or DG/µmol phosphatidylcholine (PC)).
Figure 1:
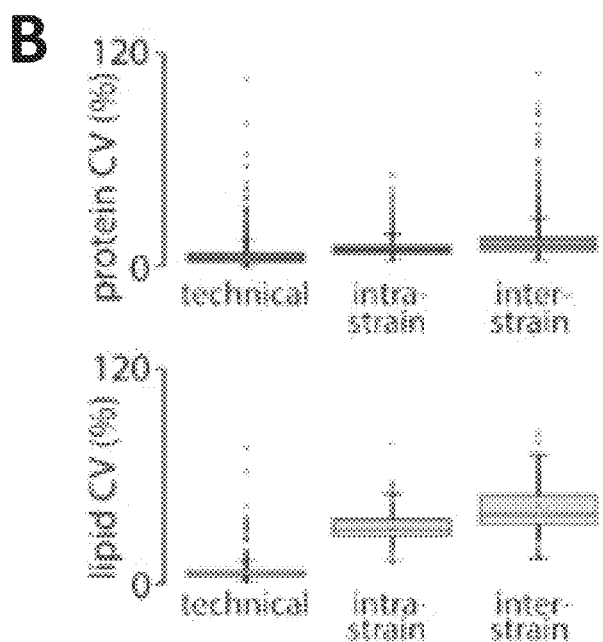
Figure 1:
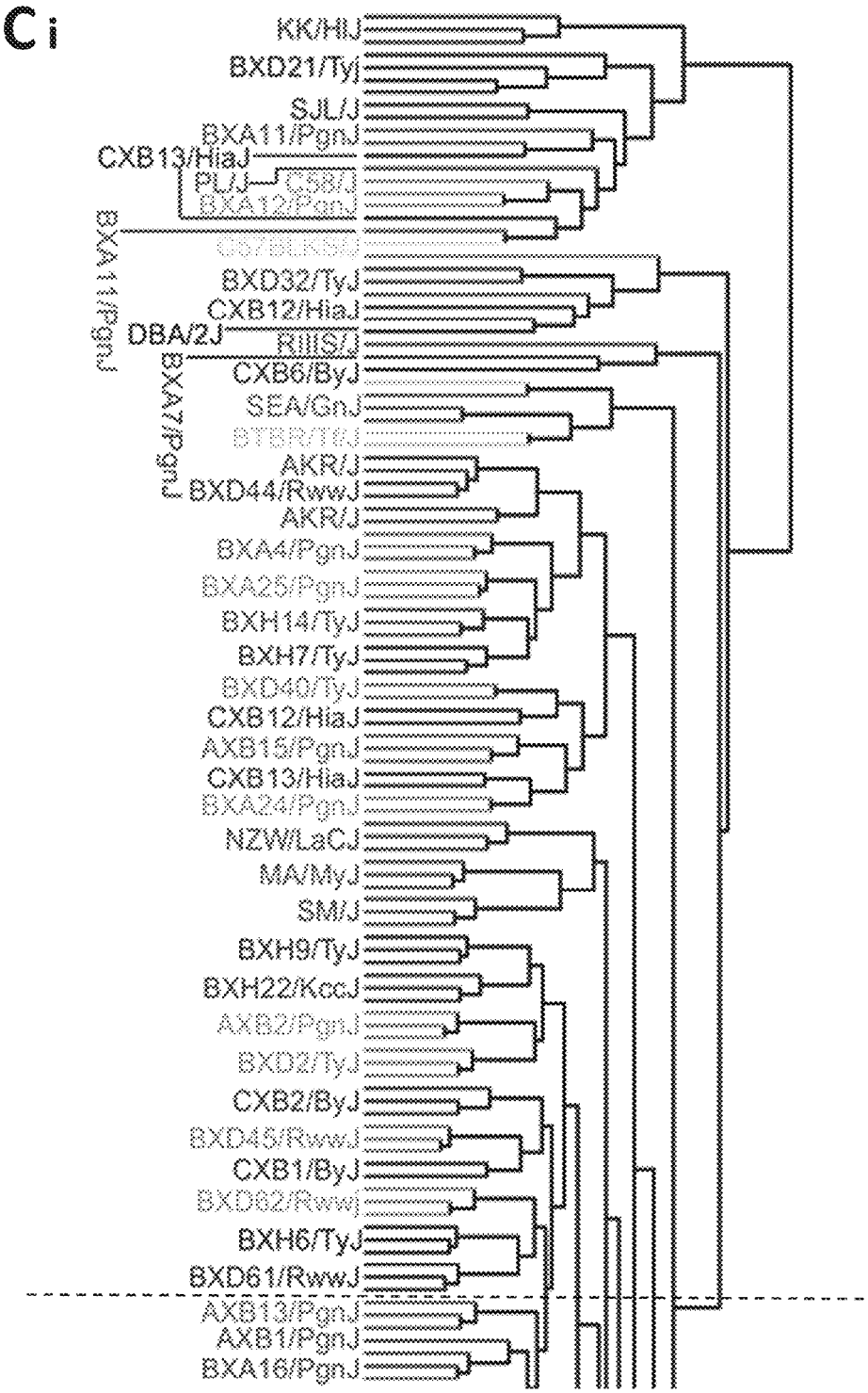
Figure 1:
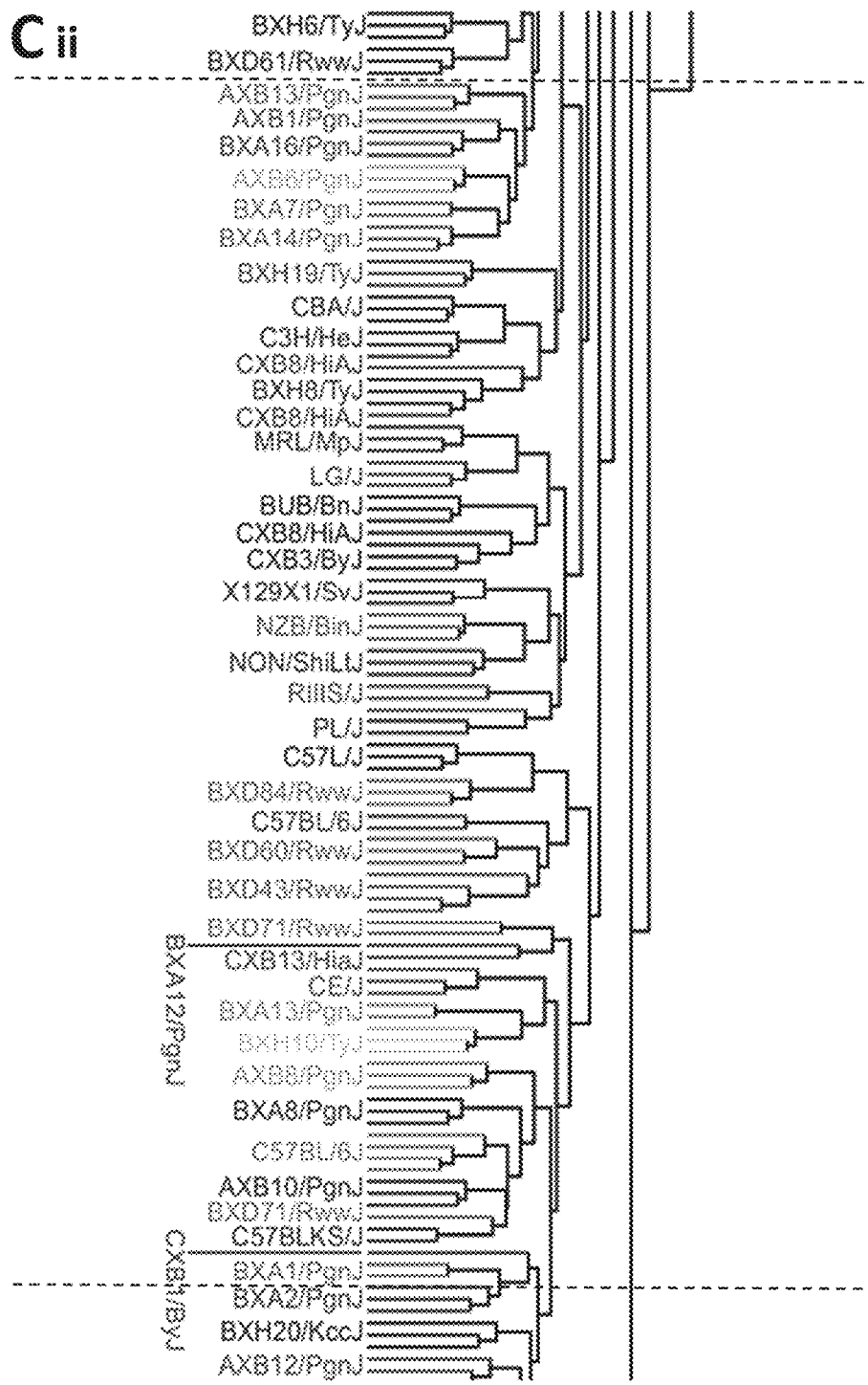
Figure 1:
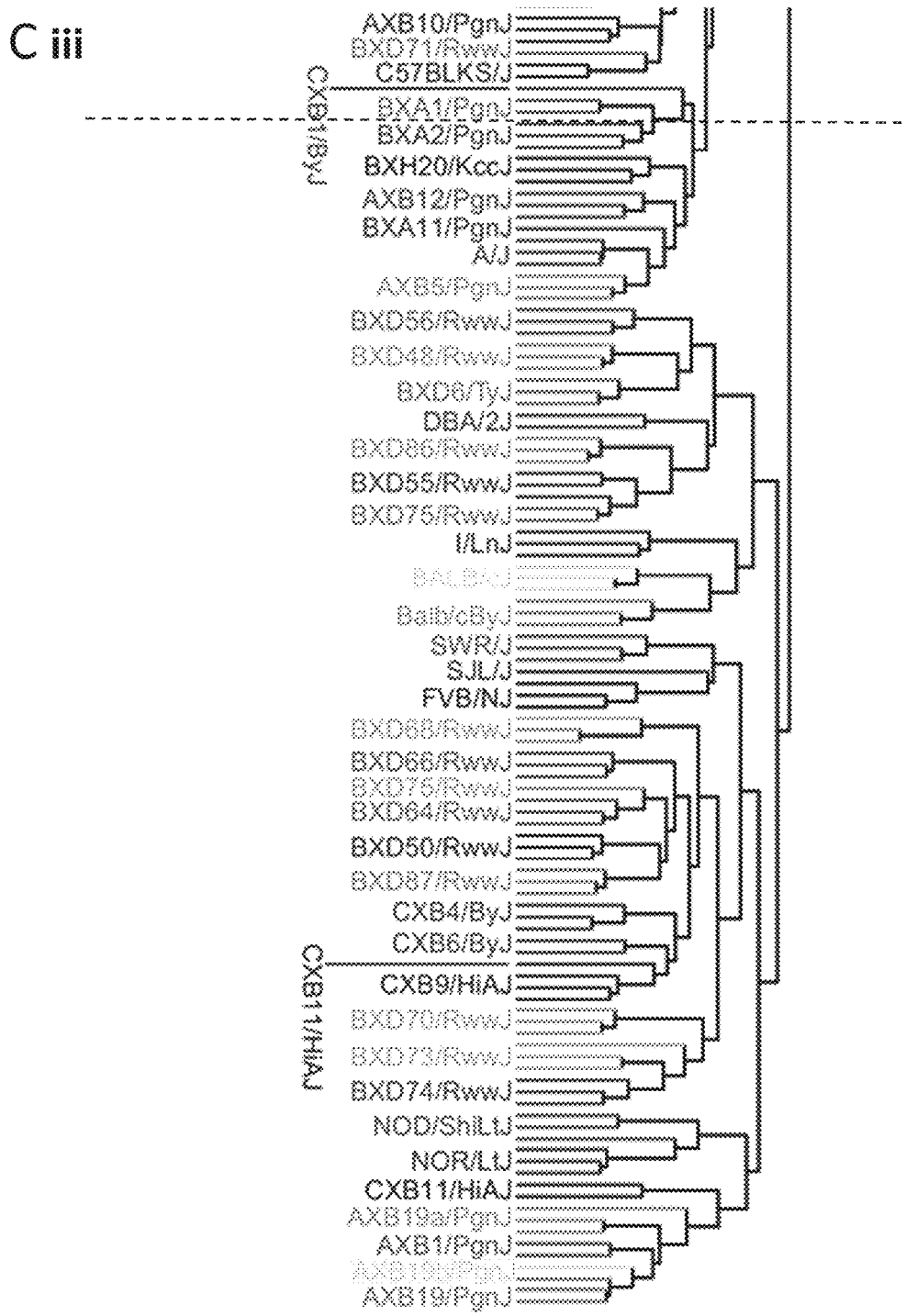
Figure 1:
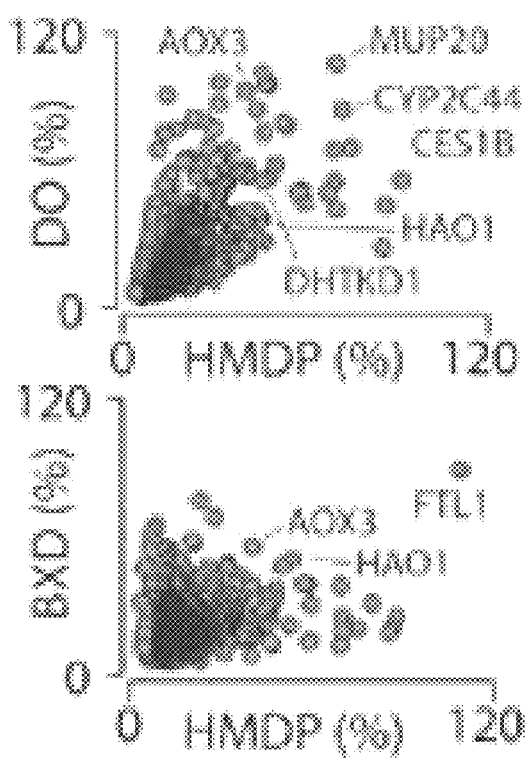
Figure 1:
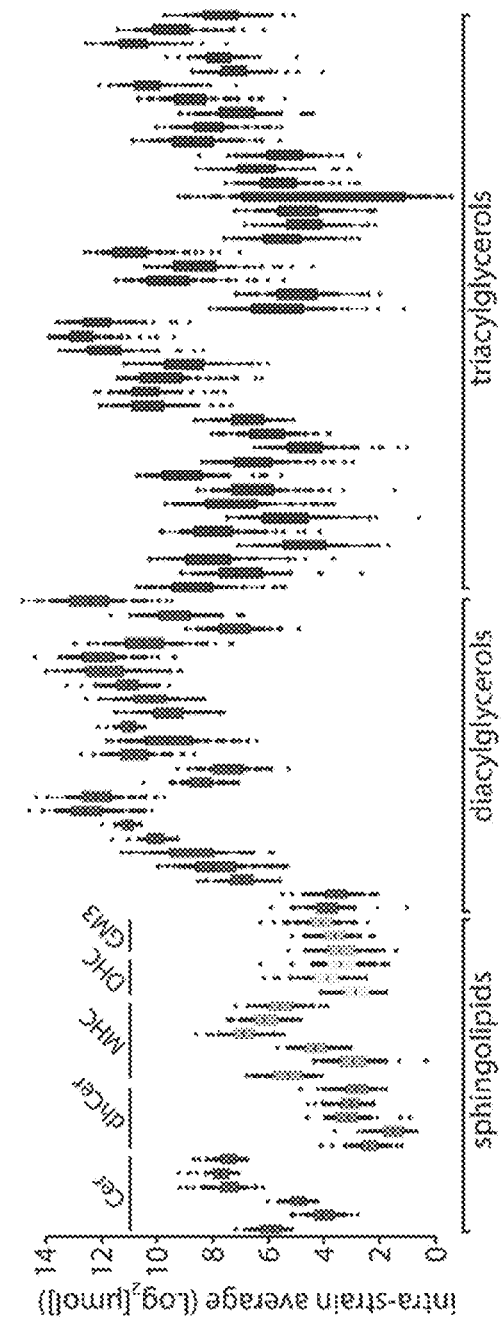
Figure 1:
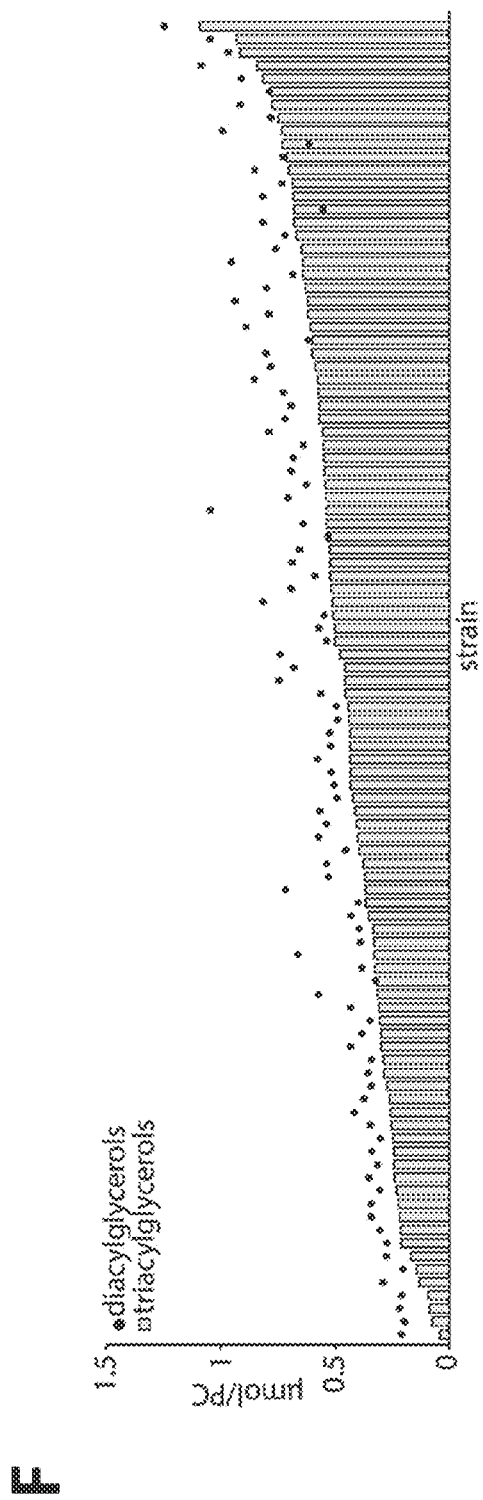

SEQ ID NO:1 human PSMD9 nucleic acid sequence GenBank NM-002813 2368 nucleotides.

SEQ ID NO:2 human PSMD9 amino acid sequence encoded by SEQ ID NO:1.

SEQ ID NO:3 mouse PSMD9 nucleic acid sequence GenBank NM-026000.

SEQ ID NO:4 mouse PSMD9 amino acid sequence.

SEQ ID NO: 5 polynucleotide sequence of mouse PSMD9 CDS included in adenovirus for overexpression studies.

SEQ ID NO: 6 nucleotide sequence of ASO 3 directed against mouse PSMD9 (Ion no. 998276).

SEQ ID NO: 7 nucleotide sequence of ASO 5 directed against mouse PSMD9 (Ion no. 998263).

SEQ ID NO: 8 nucleotide sequence of ASO 6 directed against mouse PSMD9 (Ion no. 988164).

SEQ ID NO: 9 nucleotide sequence of scrambled ASO control.

SEQ ID NO: 10 nucleotide sequence of mouse PSMD9 mRNA GenBank NM-026000.2

SEQ ID NO: 11 nucleotide sequence of mouse PSMD9 genomic sequence GenBank no. NC-000071.6 truncated sequence of target region nucleotides 123225001 to 123253000.

SEQ ID NO: 12 forward primer for probeset RTS37638 PSMD9.

SEQ ID NO: 13 reverse primer for probeset PSMD9.

SEQ ID NO: 14 probe for probeset PSMD9.

DETAILED DISCUSSION OF PARTICULAR EMBODIMENTS

As used herein, the singular forms "a", "an" and "the" include plural referents unless the context clearly dictates otherwise. For example, reference to "an isolated peptide" means one or more isolated peptides.

Throughout this specification and claims, the word "comprise," or variations such as "comprises" or "comprising," will be understood to imply the inclusion of a stated integer or group of integers but not the exclusion of any other integer or group of integers.

The term "and/or", e.g., "X and/or Y" shall be understood to mean either "X and Y" or "X or Y" and shall be taken to provide explicit support for both meanings or for either meaning.

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O(CH$_2$)$_2$—OCH$_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"cEt" or "constrained ethyl" means a bicyclic furanosyl sugar moiety comprising a bridge connecting the 4'-carbon and the 2'-carbon, wherein the bridge has the formula: 4'-CH(CH$_3$)—O-2'.

"Chemical modification" in a compound describes the substitutions or changes through chemical reaction, of any of the units in the compound. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Double-stranded compound" means a compound comprising two oligomeric compounds that are complementary to each other and form a duplex, and wherein one of the two said oligomeric compounds comprises an oligonucleotide.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase. "Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification. "Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites," are defined as unique nucleobase positions within a target nucleic acid.

"Specifically inhibit" a target nucleic acid means to reduce or block expression of the target nucleic acid while exhibiting fewer, minimal, or no effects on non-target nucleic acids reduction and does not necessarily indicate a total elimination of the target nucleic acid's expression.

"Sugar moiety" means an unmodified sugar moiety or a modified sugar moiety.

"Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Target gene" refers to a gene encoding a target.

"Targeting" means specific hybridization of a compound to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"PSMD9" is annotated as proteosome 26S subunit, non-ATPase 9. SEQ ID NOs 1 (human) and 3, 10, 11 (mouse) provide human and mouse nucleotide sequence for human and mouse PSMD9. Other variant sequences are known in the art and all variants are expressly contemplated herein for use in the production of suitable modulators using art recognized methods. The term "identity" or "identical" as used herein refers to the percentage number of amino acids that are identical or constitute conservative substitutions. Identity may be determined using sequence comparison programs such as GAP (Deveraux et al., 1984, Nucleic Acids Research 12, 387-395), which is incorporated herein by reference. In this way sequences of a similar or substantially different length to those cited herein could be compared by insertion of gaps into the alignment, such gaps being determined, for example, by the comparison algorithm used by GAP. Reference to "PSMD9" herein includes mammalian isoforms, mutants, variants, and homologs or orthologs from various species, including without limitation murine and human forms. Mouse and human protein PSMD9 sequences display X % identity as determined by NCBI BLAST based on illustrative full length sequences:

As used herein, a subject "at risk" of developing a disease or condition may or may not have detectable disease or symptoms of disease, and may or may not have displayed detectable disease or symptoms of disease prior to the treatment according to the present disclosure. "At risk" denotes that a subject has one or more risk factors, which are measurable parameters that correlate with development of the disease or condition, as known in the art and/or described herein.

As used herein, the terms "treating", "treat" or "treatment" is an approach for obtaining beneficial or desired clinical results in at least some subjects. These include administering an inhibitor as described herein to thereby reduce or eliminate at least one symptom of a hepatic lipid dysfunction condition or to slow progression of the disease or condition. Ideally this will include reduced fatty liver. As used herein, the terms "preventing", "prevent" or "prevention" include administering a modulator of the disclosure to thereby stop or hinder the development of at least one symptom of hepatic lipid dysfunction, reduce the rate of accumulation of pathological lipid species in the liver.

An "effective amount" refers to at least an amount effective, at dosages and for periods of time necessary, to achieve the desired result. For example, the desired result may be a therapeutic or prophylactic result. An effective amount can be provided in one or more administrations. In some examples of the present disclosure, the term "effective amount" is meant an amount necessary to effect treatment of hepatic lipid dysregulation. In some examples of the present disclosure, the term "effective amount" is meant an amount necessary to effect a change in a factor associated with a disease or condition as hereinbefore described. For example, the effective amount may be sufficient to effect a change in the level of pathogenic lipid species such as in the liver or plasma. The effective amount may vary according to the disease or condition to be treated or factor to be altered and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. Accordingly, this term is not to be construed to limit the disclosure to a specific quantity, e.g., weight or number of binding proteins. The effective amount can be administered in a single dose or in a dose repeated once or several times over a treatment period. For proteins or peptides the effective amount includes from about 10 ug/kg to 20 mg/kg body weight of protein or peptide.

A "therapeutically effective amount" is at least the minimum concentration required to effect a measurable improvement of a particular disease or condition. A therapeutically effective amount herein may vary according to factors such as the disease state, age, sex, and weight of the patient, and the ability of the modulator to elicit a desired response in the individual. A therapeutically effective amount is also one in which any toxic or detrimental effects of the PSMD9 inhibitor are outweighed by the therapeutically beneficial effects. In one example, a therapeutically effective amount shall be taken to mean a sufficient quantity of PSMD9 inhibitor to reduce or inhibit one or more symptoms of hepatic lipid dysfunction such as fatty liver, fatty liver disease, NAFLD, NASH, T2D and insulin resistance. As used herein, the term "prophylactically effective amount" shall be taken to mean a sufficient quantity of PSMD9 inhibitor to prevent or inhibit or delay the onset of one or more detectable symptoms of hepatic lipid dysfunction such as fatty liver, fatty liver disease, NAFLD, NASH, T2D and insulin resistance. As determined herein PSMD9 inhibition is associated with a reduction in the following pathologies or symptoms induced by a Western diet; hepatic steatosis, pathological lipid accumulation, de novo lipogenesis (DNL), hepatocyte ballooning, inflammatory response, hepatic fibrosis, endoplasmic reticulum (ER) stress and elevated blood glucose. Improvements in any one or more of these pathologies or a reduction in or a reduction in changes in marker levels indicative of these pathologies provides the skilled person with a frame work to determine a therapeutic or prophylactic effect.

It will be apparent that "inhibition" of PSMD9 includes partial inhibition such as, for example, by at least about 20% or 30% or 40% or 50% or 60% or 70% or 80% or 90% or 95% inhibition. In some embodiments the PSMD9 inhibitor completely suppresses PSMD9 activity expression in the subject or a cell of the subject for a time and under conditions sufficient to reduce lipid abundance in the liver or to reduce the rate of accumulation of pathlogical lipids in the subject.

Peptides and Peptidomimetics

The term "peptide" refers to a sequence of two or more amino acids (e.g. as defined hereinabove) wherein the amino acids are sequentially joined together by amide (peptide) bonds. The sequence may be linear or cyclic. When the sequence is cyclic, the peptide may further comprise other bond types connecting the amino acids, such as an ester bond (a depsipeptide) or a disulfide bond. For example, a cyclic peptide can be prepared or may result from the formation of a disulfide bridge between two cysteine residues in a sequence. Peptide sequences specifically recited herein are written with the amino or N-terminus on the left and the carboxy or C-terminus on the right. A "peptide residue" refers to a sequence of amino acids, that is, amino acids connected by amide bonds, wherein the N-terminus and the C-terminus are not necessarily in free form but may be further linked to additional amino acids or to other radicals. Thus a single peptide may include a large set of possible peptide residues as defined herein. Optionally substituted amino acids and peptides include, although are not limited to phosphoamino acids, phosphopeptides, methylated amino acids, methylated peptides, glycoamino acids, glycopeptides, acylated amino acids, acylated peptides, isoprenylated amino acids, isoprenylated peptides, alkylated amino acids, alkylated peptides, sulfated amino acids, sulfated peptides, glycophosphatidylinositol (GPI anchor) amino acids, glycophosphatidylinositol peptides, ubiquitinated amino acids and ubiquitinated peptides.

Suitable peptides, such as foldamers or stapled peptides, can modulate the level of PSMD9 in a cell, tissue (including blood) or subject to effect lipid remodelling. In one embodiment, the cell is a liver cell.

Peptides include phosphopeptides and phosphomimetic peptides. Peptides may be prepared by various synthetic methods known in the art via condensation of one or more amino acids. Peptides may be prepared according to standard solid-phase methods such as may be performed on a peptide synthesizer. Liquid phase methods are also known in the art.

Phosphopeptides may be prepared for example by phosphate assisted peptide ligation.

Phophomimetics retain at least one amide bond while others are replaced by an alternative linker, retain or even enhance the biological activity of a peptide for example by reducing enzymatic degradation in vivo leading to longer half-lives which can be advantageous in some embodiments. Peptides with for example phosphomimetic modifications may be readily synthesized by non-fermentatic methods.

A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub., provides a general discussion of prior art techniques for the design and synthesis of peptidomimetics. Suitable amide bond surrogates include the following groups: N-alkylation, retro-inverse amide, thioamide, thioester, phosphonate, ketomethylene, hydroxymethylene, fluorovinyl, vinyl, methyleneamino, methylenethio, alkane and sulfonamido.

Peptides and peptidomimetics will generally have a backbone of 4 to 20, or 7 to 16 amino acids in length. Molecules having backbones at the upper end of these ranges will generally comprise beta and/or gamma amino acids or their equivalents.

Polypeptide or Polypeptide Fragment PSMD9 Modulators

In some embodiments a PSMD9 inhibitor is a polypeptide inhibitor or antagonist, which may modulate PSMD9 activity by one or more of a number of different mechanisms, for example by specifically binding to PSMD9 or a PSMD9 binding partner thereby reducing interaction of PSMD9 and the binding partner, or, alternatively, competing with PSMD9 for interaction with a binding partner.

In some embodiments a PSMD9 modulator is an antibody or PSMD9-binding fragment thereof that binds to PSMD9 and inhibits its activity. The antibody is generally an antibody modified to penetrate or be taken up (passively or actively) in mammalian cells including liver cells.

The term "antibody" as used herein includes polyclonal antibodies, monoclonal antibodies, bispecific antibodies, fusion diabodies, triabodies, heteroconjugate antibodies, and chimeric antibodies. Also contemplated are antibody fragments that retain at least substantial (about 10%) antigen binding relative to the corresponding full length antibody. Antibody-based peptides such as linear, monocyclic, bicyclic, stapled or structurally constrained peptides known in the art or polypeptides that penetrate cells of the subject and particularly liver cells and inhibit PSMD9 expression or activity are expressly contemplated. Such antibody fragments are referred to herein as "antigen-binding fragments". Antibodies include modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light (VL) and heavy chain (VH) variable regions which may be joined directly or through a linker, or Fd fragments containing the heavy chain variable region and the CHI domain.

A scFv consisting of the variable regions of the heavy and light chains linked together to form a single-chain antibody and oligomers of scFvs such as diabodies and triabodies are also encompassed by the term "antibody". Also encompassed are fragments of antibodies such as Fab, (Fab')2 and FabFc2 fragments which contain the variable regions and parts of the constant regions. Complementarity determining region (CDR)-grafted antibody fragments and oligomers of antibody fragments are also encompassed. The heavy and light chain components of an Fv may be derived from the same antibody or different antibodies thereby producing a chimeric Fv region. The antibody may be of animal (for example mouse, rabbit or rat) or human origin or may be chimeric or humanized.

As used herein the term "antibody" includes these various forms. Using the guidelines provided herein and those methods well known to those skilled in the art which are described in the references cited above and in such publications as Harlow & Lane Antibodies: a Laboratory Manual, Cold Spring Harbor Laboratory, (1988) the antibodies for use in the methods of the present invention can be readily made.

The antibodies may be Fv regions comprising a variable light (VL) and a variable heavy (VH) chain in which the light and heavy chains may be joined directly or through a linker. As used herein a linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the Ig portion of the fusion polypeptide. In another embodiment, recombinantly produced single chain scFv antibody, preferably a humanized scFv, is used in the methods of the invention.

In one embodiment, the antibodies have the capacity for intracellular transmission. Antibodies which have the capacity for intracellular transmission include antibodies such as camelids and llama antibodies, shark antibodies (IgNARs), scFv antibodies, intrabodies or nanobodies, for example, scFv intrabodies and VHH intrabodies. Yeast SPLINT antibody libraries are available for testing for intrabodies which are able to disrupt protein-protein interactions. Such agents may comprise a cell-penetrating peptide sequence or nuclear-localizing peptide sequence such as those disclosed in Constantini et al. (2008). Also useful for in vivo delivery are Vectocell or Diato peptide vectors such as those disclosed in De Coupade et al. (2005).

In addition, the antibodies may be fused to a cell penetrating agent, for example a cell-penetrating peptide. Cell penetrating peptides include Tat peptides, Penetratin, short amphipathic peptides such as those from the Pep- and MPG-families, oligoarginine and oligolysine. In one example, the cell penetrating peptide is also conjugated to a lipid (C6-C 1 8 fatty acid) domain to improve intracellular delivery (Koppelhus et al., 2008). Examples of cell penetrating peptides are known in the art. Thus, the invention also provides the therapeutic use of antibodies fused via a covalent bond (e.g. a peptide bond), at optionally the N-terminus or the C-terminus, to a cell-penetrating peptide sequence.

Antibodies which specifically target mammalian PSMD9 are available from various commercial sources.

Small Molecule PSMD9 Modulators

PDSM9 modulators may be small molecules. Small molecules are molecules having a molecular mass less than 2000 daltons. Small molecules may be in the form of pro-drugs or active metabolites. Small molecules may be used in the form of a salt wherein the counter ion is pharmaceutically or physiologically acceptable. Suitable salts are known in the art. The skilled person will understand the use of small molecules in the form of solvates such as hydrates. Small molecules may also be in amorphous or crystalline form.

Small molecules useful for the present application of down modulating PSMD9 can be identified using standard procedures, such as without limitation screening a library of candidate compounds for binding to PSMD9 and then determining whether any of the compounds which bind to PSMD9 also down modulate PSMD9 activity or binding. In silico modelling of compounds can also be useful as can high throughput chemical screening, functional based assays or structure activity relationships.

Small molecules, peptides etc and other agents can be screened by competitive fluorescence polarization binding assays and then progress to more selective quantitation of PSMD9 inhibition, binding and specificity. Activity studies may be conducted using dilutions of agents and in vitro or in vivo screens for their ability to modulate lipid metabolism. Such screens, identified herein or known in the art are applied in vivo and used to test and develop candidate agents and determine their stability and toxicity, bioavailability etc. Thus, the term "in the manufacture of a medicament" encompasses in vitro and in vivo screening and development. Natural products, combinatorial synthetic organic or inorganic compounds, fragment libraries, peptide/polypeptide/protein, nucleic acid molecules and libraries or phage or other display technology comprising these are all available to screen or test for suitable agents.

Natural products include those from coral, soil, plant, or the ocean or Antarctic environments. Libraries of small organic molecules can be generated and screened using high-throughput technologies known to those of skill in this art. See for example U.S. Pat. No. 5,763,623 and United States Application No. 20060167237. Combinatorial synthesis provides a very useful approach wherein a great many related compounds are synthesized having different substitutions of a common or subset of parent structures. Such compounds are usually non-oligomeric and may be similar in terms of their basic structure and function, for example, varying in chain length, ring size or number or substitutions. Virtual libraries are also contemplated and these may be constructed and compounds tested in silico (see for example, US Publication No. 20060040322) or by in vitro or in vivo assays known in the art. Libraries of small molecules suitable for testing are available in the art (see for example, Amezcua et al., Structure (London), 10: 1349-1361, 2002). Yeast SPLINT antibody libraries are available for testing for intrabodies which are able to disrupt protein-protein interactions (see Visintin et al., supra). Examples of suitable methods for the synthesis of molecular libraries can be found in the art. Bicyclic peptides are recently described in Liskamp Nature Chemistry 6, 855-857 2014. Agents may be hydrocarbon-stapled peptides or miniature proteins which are alpha-helical and cell-penetrating, and are able to disrupt protein-protein interactions (see for example, Wilder et al., Chem Med Chem. 2(8): 1149-1151, 2007; & for a review see, Henchey et al., Curr. Opin. Chem. Biol., 2(6):692-697, 2008. See also U.S. Publication No. 2005/0250680.

Thus, agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is suited to peptide libraries, while the other four approaches are applicable to peptide, non-peptide oligomer or small molecule libraries of compounds. Libraries of compounds may be presented, for example, in solution, or on beads, chips, bacteria, spores and plasmids or phage as known in the art.

In one embodiment a small molecule PSMD9 modulator is a reversible or an irreversible inhibitor of PSMD9.

In one embodiment, a small molecule PSMD9 modulator is an inhibitor of the expression of PSMD9.

Oligonucleotide PSMD9 Modulators

In one embodiment the present disclosure enables the use of an antisense compound to PSMD9. Such antisense compounds are targeted to nucleic acids encoding the PSMD9. In one embodiment, the antisense compound is an oligonucleotide. However, other oligomeric antisense compounds, including but not limited to oligonucleotide mimetics are contemplated.

In certain embodiments, compounds described herein are antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid. In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, each modified oligonucleotide is 12-30 linked nucleosides in length.

In certain embodiments, compounds are double-stranded. Such double-stranded compounds comprise a first oligomeric compound having a region complementary to a target nucleic acid and a second oligomeric compound having a region complementary to the first oligomeric compound. The first oligomeric compound of such double stranded compounds typically comprises or consists of a modified oligonucleotide. The oligonucleotide of the second oligomeric compound of such double-stranded compound may be modified or unmodified. The oligomeric compounds of double-stranded compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

Hybridization of an antisense compound with its target nucleic acid is generally referred to as "antisense". Hybridization of the antisense compound with its target nucleic acid inhibits the function of the target nucleic acid. Such "antisense inhibition" is typically based upon hydrogen bonding-based hybridization of the antisense compound to the target nucleic acid such that the target nucleic acid is cleaved, degraded, or otherwise rendered inoperable. The functions of target DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

"Hybridization" as used herein means pairing of complementary bases of the oligonucleotide and target nucleic acid. Base pairing typically involves hydrogen bonding, which may be Watson-Crick, Hoogsteen or reversed Hoogsteen hydrogen bonding, between complementary nucleoside or nucleotide bases (nucleobases). Guanine (G) and cytosine (C) are examples of complementary nucleobases which pair through the formation of 3 hydrogen bonds. Adenine (A) and thymine (T) are examples of complementary nucleobases which pair through the formation of 2 hydrogen bonds. Hybridization can occur under varying circumstances.

A "nucleoside" is a base-sugar combination. The base portion of the nucleoside is normally a heterocyclic base. The two most common classes of such heterocyclic bases are the purines and the pyrimidines. "Nucleotides" are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar.

"Specifically hybridizable" and "complementary" are terms which are used to indicate a sufficient degree of complementarity such that stable and specific binding occurs between the antisense compound and target nucleic acid. It is understood that the antisense compound need not be 100% complementary to its target nucleic acid sequence to be specifically hybridizable. An antisense compound is specifically hybridizable when binding of the antisense compound to the target nucleic acid interferes with the normal function of the target molecule to cause a loss of activity, and there is a sufficient degree of complementarity to avoid non-specific binding of the antisense compound to non-target sequences under conditions in which specific binding is desired, for example, under physiological conditions in the case of therapeutic treatment.

"Complementary" as used herein, refers to the capacity for precise pairing between a nucleobase of the antisense compound and the target nucleic acid. For example, if a nucleobase at a certain position of the antisense compound is capable of hydrogen bonding with a nucleobase at a certain position of the target nucleic acid, then the position of hydrogen bonding between the antisense compound and the target nucleic acid is considered to be a complementary position. The antisense compound may hybridize over one or more segments, such that intervening or adjacent segments are not involved in the hybridization event (e.g., a loop structure or hairpin structure). In one embodiment, the antisense compound comprises at least 70% sequence complementarity to a target region within the target nucleic acid.

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a PSMD9 nucleic acid may be tolerated provided that the compound remains able to specifically hybridize to a target nucleic acid. Moreover, a compound may hybridize over one or more segments of a PSMD9 nucleic acid such that intervening or adjacent segments are not involved in the hybridization event (e.g., a loop structure, mismatch or hairpin structure).

For example, an antisense compound in which 18 of 20 nucleobases are complementary to a target region within the target nucleic acid, and would therefore specifically hybridize, would represent 90% complementarity. In this example, the remaining noncomplementary nucleobases may be clustered or interspersed with complementary nucleobases and need not be contiguous to each other, or to complementary nucleobases. As such, an antisense compound which is 18 nucleobases in length having 4 non-complementary nucleobases which are flanked by 2 regions of complete complementarity with the target nucleic acid would have 77.8% overall complementarity with the target nucleic acid and would thus, fall within the scope of the present disclosure. Percent complementarity of an antisense compound with a region of a target nucleic acid can be determined routinely using BLAST programs (basic local alignment search tools) and PowerBLAST programs known in the art (Altschul et al., 1990; Zhang and Madden, 1997).

In certain embodiments, the compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a PSMD9 nucleic acid, a target region, target segment, or specified portion thereof.

In certain embodiments, compounds described herein, or specified portions thereof, are fully complementary (i.e. 100% complementary) to a target nucleic acid, or specified portion thereof. For example, a compound may be fully complementary to a PSMD9 nucleic acid, or a target region, or a target segment or target sequence thereof. As used herein, "fully complementary" means each nucleobase of a compound is capable of precise base pairing with the corresponding nucleobases of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

In some embodiments, the antisense molecule is substantially identical with at least a region of the coding sequence of the target gene to enable down-regulation of the gene. In some embodiments, the degree of identity between the sequence of the antisense molecule and the targeted region of the gene is at least 60% sequence identity, in some embodiments at least 75% sequence identity, for instance at least 85% identity, 90% identity, at least 95% identity, at least 97%, or at least 99% identity.

Calculation of percentage identities between different amino acid/polypeptide/nucleic acid sequences may be carried out as follows. A multiple alignment is first generated by the ClustalX program (pairwise parameters: gap opening 10.0, gap extension 0.1, protein matrix Gonnet 250, DNA matrix IUB; multiple parameters: gap opening 10.0, gap extension 0.2, delay divergent sequences 30%, DNA transition weight 0.5, negative matrix off, protein matrix gonnet series, DNA weight IUB; Protein gap parameters, residue-specific penalties on, hydrophilic penalties on, hydrophilic residues GPSNDQERK, gap separation distance 4, end gap separation off). The percentage identity is then calculated from the multiple alignment as (N/T)*100, where N is the number of positions at which the two sequences share an identical residue, and T is the total number of positions compared.

Alternatively, percentage identity can be calculated as (N/S)*1 00 where S is the length of the shorter sequence being compared. The amino acid/polypeptide/nucleic acid sequences may be synthesized de novo, or may be native amino acid/polypeptide/nucleic acid sequence, or a derivative thereof. A substantially similar nucleotide sequence will be encoded by a sequence which hybridizes to any of the nucleic acid sequences referred to herein or their complements under stringent conditions. By stringent conditions, we mean the nucleotide hybridizes to filter-bound DNA or RNA in 6x sodium chloride/sodium citrate (SSC) at approximately 45° C. followed by at least one wash in 0.2×SSC/ 0.1% SDS at approximately 5-65° C. Alternatively, a substantially similar polypeptide may differ by at least 1, but less than 5, 10, 20, 50 or 100 amino acids from the peptide sequences according to the present invention Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequences which are altered by the substitution of different codons that encode an amino acid with a side chain of similar biophysical properties to the amino acid it substitutes, to produce a conservative change.

For example small non-polar, hydrophobic amino acids include glycine, alanine, leucine, isoleucine, valine, proline, and methionine; large non-polar, hydrophobic amino acids include phenylalanine, tryptophan and tyrosine; the polar neutral amino acids include serine, threonine, cysteine, asparagine and glutamine; the positively charged (basic) amino acids include lysine, arginine and histidine; and the negatively charged (acidic) amino acids include aspartic acid and glutamic acid. The accurate alignment of protein or DNA sequences is a complex process, which has been investigated in detail by a number of researchers. Of particular importance is the trade-off between optimal matching of sequences and the introduction of gaps to obtain such a match. In the case of proteins, the means by which matches are scored is also of significance. The family of PAM matrices (e.g., Dayhoff, M. et al., 1978, Atlas of protein sequence and structure, Natl. Biomed. Res. Found) and BLOSUM matrices quantify the nature and likelihood of conservative substitutions and are used in multiple alignment algorithms, although other, equally applicable matrices will be known to those skilled in the art. The popular multiple alignment program ClustalW, and its windows version ClustalX (Thompson et al., 1994, Nucleic Acids Research, 22, 4673-4680; Thompson et al., 1997, Nucleic Acids Research, 24, 4876-4882) are efficient ways to generate multiple alignments of proteins and DNA. Frequently, automatically generated alignments require manual alignment, exploiting the trained user's knowledge of the protein family being studied, e.g., biological knowledge of key conserved sites. One such alignment editor programs is Align (http://www.gwdg.de/dhepper/download/; Hepperle, D., 2001: Multicolor Sequence Alignment Editor. Institute of Freshwater Ecology and Inland Fisheries, 1 6775 Stechlin, Germany), although others, such as JalView or Cinema are also suitable. Calculation of percentage identities between proteins occurs during the generation of multiple alignments by Clustal. However, these values need to be recalculated if the alignment has been manually improved, or for the deliberate comparison of two sequences. Programs that calculate this value for pairs of protein sequences within an alignment include PROTDIST within the PHYLIP phylogeny package (Felsenstein; http://evolution.gs.washington.edu/phylip.html) using the "Similarity Table" option as the model for amino acid substitution (P). For DNA/RNA, an identical option exists within the DNADIST program of PHYL1 P.

The molecules may comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. In an embodiment, the NA molecules specifically target one given gene. In order to only target the desired mRNA, the antisense reagent may have 1 00% homology to the target mRNA and at least 2 mismatched nucleotides to all other genes present in the cell or organism. Methods to analyze and identify siRNAs with sufficient sequence identity in order to effectively inhibit expression of a specific target sequence are known in the art. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group).

The length of the region of the antisense complementary to the target, in accordance with the present invention, may be from 10 to 100 nucleotides, 12 to 25 nucleotides, 14 to 22 nucleotides or 15, 16, 17 or 18 nucleotides.

In certain embodiments, a compound described herein comprises an oligonucleotide 10 to 30 linked subunits in length. In certain embodiments, compound described herein comprises an oligonucleotide is 12 to 30 linked subunits in length. In certain embodiments, compound described herein comprises an oligonucleotide is 12 to 22 linked subunits in length. In certain embodiments, compound described herein comprises an oligonucleotide is 14 to 30 linked subunits in length. In certain embodiments, compound described herein comprises an oligonucleotide is 14 to 20 linked subunits in length. In certain embodiments, compound described herein comprises an oligonucleotide is 15 to 30 linked subunits in length. In certain embodiments, compound described herein comprises an oligonucleotide is 15 to 20 linked subunits in length. In certain embodiments, compound described herein comprises an oligonucleotide is 16 to 30 linked subunits in length. In certain embodiments, compound described herein comprises an oligonucleotide is 16 to 20 linked subunits in length. In certain embodiments, compound described herein comprises an oligonucleotide is 17 to 30 linked subunits in length. In certain embodiments, compound described herein comprises an oligonucleotide is 17 to 20 linked subunits in length. In certain embodiments, compound described herein comprises an oligonucleotide is 18 to 30 linked subunits in length. In certain embodiments, compound described herein comprises an oligonucleotide is 18 to 21 linked subunits in length. In certain embodiments, compound described herein comprises an oligonucleotide is 18 to 20 linked subunits in length. In certain embodiments, compound described herein comprises an oligonucleotide is 20 to 30 linked subunits in length. In other words, such oligonucleotides are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

Where there are mismatches to the corresponding target region, the length of the complementary region is generally required to be somewhat longer. In an embodiment, the inhibitor is a siRNA molecule and comprises between approximately 5 bp and 50 bp, in some embodiments, between 10 bp and 35 bp, or between 15 bp and 30 bp, for instance between 18 bp and 25 bp. In some embodiments, the siRNA molecule comprises more than 20 and less than 23 bp.

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics.

In certain embodiments, a double-stranded compound comprises a first strand comprising the nucleobase sequence complementary to a target region of a PSMD9 nucleic acid and a second strand. In certain embodiments, the double-stranded compound comprises ribonucleotides in which the first strand has uracil (U) in place of thymine (T) and is complementary to a target region. In certain embodiments, a double-stranded compound comprises (i) a first strand comprising a nucleobase sequence complementary to a target region of a PSMD9 nucleic acid, and (ii) a second strand. In certain embodiments, the double-stranded compound comprises one or more modified nucleotides in which the 2' position in the sugar contains a halogen (such as fluorine group; 2'-F) or contains an alkoxy group (such as a methoxy group; 2'-OMe). In certain embodiments, the double-stranded compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the double-stranded compound comprises one or more linkages between adjacent nucleotides other than a naturally-occurring phosphodiester linkage. Examples of such linkages include phosphoramide, phosphorothioate, and phosphorodithioate linkages. The double-stranded compounds may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000. In certain embodiments, the first strand of the double-stranded compound is an siRNA guide strand and the second strand of the double-stranded compound is an siRNA passenger strand. In certain embodiments, the second strand of the double-stranded compound is complementary to the first strand. In certain embodiments, each strand of the double-stranded compound consists of 16, 17, 18, 19, 20, 21, 22, or 23 linked nucleosides.

In certain embodiments, a single-stranded compound described herein can comprise any of the oligonucleotide sequences targeted to PSMD9 described herein. In certain embodiments, such a single-stranded compound is a single-stranded RNAi (ssRNAi) compound. In certain embodiments, a ssRNAi compound comprises the nucleobase sequence complementary to a target region of a PSMD9 nucleic acid. In certain embodiments, the ssRNAi compound comprises ribonucleotides in which uracil (U) is in place of thymine (T).

In certain embodiments, ssRNAi compound comprises a nucleobase sequence complementary to a target region of a PSMD9 nucleic acid. In certain embodiments, a ssRNAi compound comprises one or more modified nucleotides in which the 2' position in the sugar contains a halogen (such as fluorine group; 2'-F) or contains an alkoxy group (such as a methoxy group; 2'-OMe). In certain embodiments, a ssRNAi compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the ssRNAi compound. In certain embodiments, the ssRNAi compound comprises one or more linkages between adjacent nucleotides other than a naturally-occurring phosphodiester linkage. Examples of such linkages include phosphoramide, phosphorothioate, and phosphorodithioate linkages. The ssRNAi compounds may also be chemically modified nucleic acid molecules as taught in U.S. Pat. No. 6,673,661. In other embodiments, the ssRNAi contains a capped strand, as disclosed, for example, by WO 00/63364, filed Apr. 19, 2000. In certain embodiments, the ssRNAi compound consists of 16, 17, 18, 19, 20, 21, 22, or 23 linked nucleosides.

Because the siRNA may carry overhanging ends (which may or may not be complementary to the target), or additional nucleotides complementary to itself but not the target gene, the total length of each separate strand of siRNA may be 10 to 1 00 nucleotides, 15 to 49 nucleotides, 17 to 30 nucleotides or 1 9 to 25 nucleotides. The phrase "each strand is 49 nucleotides or less" means the total number of consecutive nucleotides in the strand, including all modified or unmodified nucleotides, but not including any chemical moieties which may be added to the 3' or 5' end of the strand. Short chemical moieties inserted into the strand are not counted, but a chemical linker designed to join two separate strands is not considered to create consecutive nucleotides.

The phrase "a 1 to 6 nucleotide overhang on at least one of the 5' end or 3' end" refers to the architecture of the complementary siRNA that forms from two separate strands under physiological conditions. If the terminal nucleotides are part of the double-stranded region of the siRNA, the siRNA is considered blunt ended. If one or more nucleotides are unpaired on an end, an overhang is created. The overhang length is measured by the number of overhanging nucleotides. The overhanging nucleotides can be either on the 5' end or 3' end of either strand. The siRNA according to the present invention display a high in vivo stability and may be particularly suitable for oral delivery by including at least one modified nucleotide in at least one of the strands.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

The term "microRNA" (abbreviated miRNA) is a small non-coding RNA molecule (containing about 22 nucleotides) found in plants, animals and some viruses, that functions in RNA silencing and post-transcriptional regulation of gene expression. The prefix "miR" is followed by a dash and a number, the latter often indicating order of naming Different miRNAs with nearly identical sequences except for one or two nucleotides are annotated with an additional lower case letter. Numerous miRNAs are known in the art (miRBase V.21 nomenclature.

In one embodiment, modulatory oligonucleotides mimic the activity of one or more miRNA. The term "miRNA mimic", as used herein, refers to small, double-stranded RNA molecules designed to mimic endogenous mature miRNA molecules when introduced into cells. miRNA mimics can be obtained from various suppliers such as Sigma Aldrich and Thermo Fisher Scientific.

In one embodiment, modulatory oligonucleotides inhibit the activity of one or more miRNA. Various miRNA species are suitable for this purpose. Examples include, without limitation, antagomirs, interfering RNA, ribozymes, miRNA sponges and miR-masks. The term "antagomir" is used in the context of the present disclosure to refer to chemically modified antisense oligonucleotides that bind to a target miRNA and inhibit miRNA function by preventing binding of the miRNA to its cognate gene target. Antagomirs can include any base modification known in the art. In an example, the above referenced miRNA species are about 10 to 50 nucleotides in length. For example, antagomirs can have antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In one embodiment, modulatory oligonucleotides are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids.

In one embodiment, modulatory oligonucleotides are synthetic. The term "synthetic nucleic acid" means that the nucleic acid does not have a chemical structure or sequence of a naturally occurring nucleic acid. Synthetic nucleotides include an engineered nucleic acid such as a DNA or RNA molecule. It is contemplated, however, that a synthetic nucleic acid administered to a cell may subsequently be modified or altered in the cell such that its structure or sequence is the same as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA. Consequently, it will be understood that the term "synthetic miRNA" refers to a "synthetic nucleic acid" that functions in a cell or under physiological conditions as a naturally occurring miRNA. In another example, the nucleic acid structure can also be modified into a locked nucleic acid (LNA) with a methylene bridge between the 2' Oxygen and the 4' carbon to lock the ribose in the 3'-endo (North) conformation in the A-type conformation of nucleic acids. In the context of miRNAs, this modification can significantly increase both target specificity and hybridization properties of the molecule.

Nucleic acids for use in the methods disclosed herein can be designed using routine methods as required. For example, in the context of inhibitory oligonucleotides, target segments of 5, 6, 7, 8, 9, 10 or more nucleotides in length comprising a stretch of at least five (5) consecutive nucleotides within the seed sequence, or immediately adjacent thereto, are considered to be suitable for targeting a gene. Exemplary target segments can include sequences that comprise at least the 5 consecutive nucleotides from the 5'-terminus of one of the seed sequence (the remaining nucleotides being a consecutive stretch of the same RNA beginning immediately upstream of the 5'-terminus of the seed sequence and continuing until the nucleic acid contains about 5 to about 30 nucleotides). In another example, target segments are represented by RNA sequences that comprise at least the 5 consecutive nucleotides from the 3'-terminus of one of the seed sequence (the remaining nucleotides being a consecutive stretch of the same RNA beginning immediately downstream of the 3'-terminus of the target segment and continuing until the nucleic acid contains about 5 to about 30 nucleotides). The term "seed sequence" is used in the context of the present disclosure to refer to a 6-8 nucleotide (nt) long substring within the first 8 nt at the 5-end of the miRNA (i.e., seed sequence) that is an important determinant of target specificity. Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target nucleic acid sequences), to give the desired effect.

Various online tools are available providing software and guidelines for designing RNAi/siRNA, for example Thermo Fisher, GeneScript, InvivoGen, and the siDESIGN tool. These are then tested empirically with typically at least 3 out of 10 siRNAs anticipated to result in mRNA knockdown rate of at least 75% where the transfection efficiency is at least 80%. Reference may be made to WO2005054270 and US20030186909.

Antisense Oligonucleotides

The present disclosure provides antisense oligonucleotides for inhibiting expression of PSMD9. Such antisense oligonucleotides are targeted to nucleic acids encoding PSMD9.

The term "inhibits" as used herein means any measurable decrease (e.g., 10%, 20%, 50%, 90%, or 100%) in PSMD9 expression.

As used herein, the term "oligonucleotide" refers to an oligomer or polymer of RNA or DNA or mimetics, chimeras, analogs and homologs thereof. This term includes oligonucleotides composed of naturally occurring nucleobases, sugars and covalent internucleoside (backbone) linkages, as well as oligonucleotides having non-naturally occurring portions which function similarly. Such modified or substituted oligonucleotides are often preferred over native forms because of desirable properties such as, for example, enhanced cellular uptake, enhanced affinity for the target nucleic acid and increased stability in the presence of nucleases.

The oligonucleotides may contain chiral (asymmetric) centers or the molecule as a whole may be chiral. The individual stereoisomers (enantiomers and diastereoisomers) and mixtures of these are within the scope of the present disclosure. Reference may be made to Wan et al. Nucleic Acids Research 42 (22:13456-13468, 2014 for a disclosure of antisense oligonucleotides containing chiral phosphorothioate linkages.

In forming oligonucleotides, phosphate groups covalently link adjacent nucleosides to one another to form a linear polymeric compound. In turn, the respective ends of this linear polymeric compound can be further joined to form a circular compound; however, linear compounds are generally preferred. In addition, linear compounds may have internal nucleobase complementarity and may therefore fold in a manner so as to produce a fully or partially double-stranded compound. With regard to oligonucleotides, the phosphate groups are commonly referred to as forming the internucleoside backbone of the oligonucleotide. The normal linkage or backbone of RNA and DNA is a 3' to 5' phosphodiester linkage. Antisense oligonucleotides of the disclosure include, for example, ribozymes, siRNA, external guide sequence (EGS) oligonucleotides, alternate splicers, primers, probes, and other oligonucleotides which hybridize to at least a portion of the target nucleic acid.

Antisense oligonucleotides of the disclosure may be administered in the form of single-stranded, double-stranded, circular or hairpin and may contain structural elements such as internal or terminal bulges or loops. Once administered, the antisense oligonucleotides may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H therefore results in cleavage of the RNA target, thereby greatly enhancing the efficiency of oligonucleotide-mediated inhibition of gene expression. Similar roles have been postulated for other ribonucleases, such as those in the RNase III and ribonuclease L family of enzymes. Further, in certain embodiments, one or more non-DNA-like nucleoside in the gap of a gapmer is tolerated.

The introduction of double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

The first evidence that dsRNA could lead to gene silencing in animals came in 1995 from work in the nematode, *Caenorhabditis elegans*. Others have shown that the primary interference effects of dsRNA are posttranscriptional. The post-transcriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels. More recently, it has been shown that it is, in fact, the single-stranded RNA oligomers of antisense polarity of the dsRNAs which are the potent inducers of RNAi (Tijsterman et al., 2002). A person having ordinary skill in the art could, without undue experimentation, identify antisense oligonucleotides useful in the methods of the present disclosure.

Modified Internucleoside Linkages (Backbones)

The naturally occurring internucleoside linkage of RNA and DNA is a 3' to 5' phosphodiester linkage. In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases. Antisense compounds of the present disclosure include oligonucleotides having modified backbones or non-natural internucleoside linkages. In certain embodiments, compounds targeted to a PSMD9 nucleic acid comprise one or more modified internucleoside linkages. In certain embodiments, the modified internucleoside linkages are phosphorothioate linkages. In certain embodiments, each internucleoside linkage of the compound is a phosphorothioate internucleoside linkage. Oligonucleotides having modified backbones include those that retain a phosphorus atom in the backbone and those that do not have a phosphorus atom in the backbone.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, that is, a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808, 4,469,863, 4,476,301, 5,023,243, 5,177,196, 5,188,897, 5,264,423, 5,276,019, 5,278,302, 5,286,717, 5,321,131, 5,399,676, 5,405,939, 5,453,496, 5,455,233, 5,466,677, 5,476,925, 5,519,126, 5,536,821, 5,541,306, 5,550,111, 5,563,253, 5,571,799, 5,587,361, 5,194,599, 5,565,555, 5,527,899, 5,721,218, 5,672,697 and 5,625,050.

Modified oligonucleotide backbones that do not include a phosphorus atom therein include, for example, backbones formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleotides include, but are not limited to, U.S. Pat. Nos. 5,034,506, 5,166,315, 5,185,444, 5,214,134, 5,216,141, 5,235,033, 5,264,562, 5,264,564, 5,405,938, 5,434,257, 5,466,677, 5,470,967, 5,489,677, 5,541,307, 5,561,225, 5,596,086, 5,602,240, 5,610,289, 5,602,240, 5,608,046, 5,610,289, 5,618,704, 5,623,070, 5,663,312, 5,633,360, 5,677,437, 5,792,608, 5,646,269 and 5,677,439.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphoro-thioate. In certain embodiments, each internucleoside linkage of the oligonucleotide is selected from phosphodiester and phosphorothioate and at least one internucleoside linkage is phosphorothioate.

Modified Sugar and Internucleoside Linkages

Antisense compounds of the present disclosure include oligonucleotide mimetics where both the sugar and the internucleoside linkage (i.e. the backbone), of the nucleotide units are replaced with novel groups. The nucleobase units are maintained for hybridization with the target nucleic acid.

An oligonucleotide mimetic that has been shown to have excellent hybridization properties is referred to as a peptide nucleic acid (PNA). In PNA compounds, the sugar-backbone of an oligonucleotide is replaced with an amide containing backbone, in particular, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082, 5,714,331, and 5,719,262.

The antisense compounds of the present disclosure also include oligonucleotides with phosphorothioate backbones and oligonucleotides with heteroatom backbones, for example, —CH2-NH—O—CH2-, —CH2-N(CH3)-O—CH2- [known as a methylene (methylimino) or MMI backbone], —CH2-O—N(CH3)-CH2-, —CH2-N(CH3)-N(CH3)-CH2- and —O—N(CH3)-CH2-CH2- [wherein the native phosphodiester backbone is represented as —O—P—O—CH2-] of U.S. Pat. No. 5,489,677, and the amide backbones of U.S. Pat. No. 5,602,240.

The antisense compounds of the present disclosure also include oligonucleotides having morpholino backbone structures of U.S. Pat. No. 5,034,506.

Modified Sugars

Antisense compounds of the present disclosure include oligonucleotides having one or more substituted sugar moieties. In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

Examples include oligonucleotides comprising one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl.

In one embodiment, the oligonucleotide comprises one of the following at the 2' position: O[(CH2)nO]mCH3, O(CH2)nOCH3, O(CH2)nNH2, O(CH2)nCH3, O(CH2)nONH2, and O(CH2)nON[(CH2)nCH3]2, where n and m are from 1 to about 10.

Further examples include of modified oligonucleotides include oligonucleotides comprising one of the following at the 2' position: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

In one embodiment, the modification includes 2'-methoxyethoxy (2'-O—CH2CH2OCH3 (also known as 2'-O-(2-methoxyethyl) or 2'-MOE), that is, an alkoxyalkoxy group. In a further embodiment, the modification includes 2'-dimethylaminooxyethoxy, that is, a O(CH2)2ON(CH3)2 group (also known as 2'-DMAOE), or 2'-dimethylaminoethoxyethoxy (also known in the art as 2'-O-dimethyl-aminoethoxy-ethyl or 2'-DMAEOE), that is, 2'-O—CH2-O—CH2-N(CH3)2.

Other modifications include 2'-methoxy (2'-O—CH3), 2'-aminopropoxy (2'-OCH2CH2CH2NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. In one embodiment a 2'-arabino modification is 2'-F.

Similar modifications may also be made at other positions on the oligonucleotide, particularly the 3' position of the sugar on the 3' terminal nucleotide or in 2'-5' linked oligonucleotides and the 5' position of the 5' terminal nucleotide.

Oligonucleotides may also have sugar mimetics, such as cyclobutyl moieties in place of the pentofuranosyl sugar.

Representative United States patents that teach the preparation of such modified sugar structures include, but are not limited to, U.S. Pat. Nos. 4,981,957, 5,118,800, 5,319,080, 5,359,044, 5,393,878, 5,446,137, 5,466,786, 5,514,785, 5,519,134, 5,567,811, 5,576,427, 5,591,722, 5,597,909, 5,610,300, 5,627,053, 5,639,873, 5,646,265, 5,658,873, 5,670,633, 5,792,747, and 5,700,920.

A further modification of the sugar includes Locked Nucleic Acids (LNAs) in which the 2'-hydroxyl group is linked to the 3' or 4' carbon atom of the sugar ring, thereby forming a bicyclic sugar moiety. In one embodiment, the linkage is a methylene (—CH2-)n group bridging the 2' oxygen atom and the 4' carbon atom, wherein n is 1 or 2. LNAs and preparation thereof are described in WO 98/39352 and WO 99/14226.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C—(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

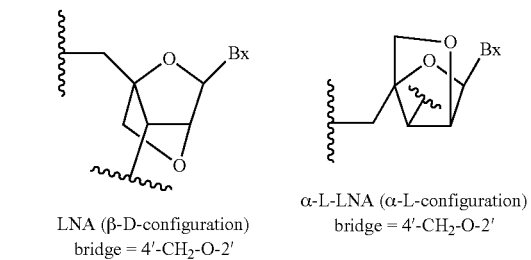

LNA (β-D-configuration)
bridge = 4'-CH$_2$-O-2'

α-L-LNA (α-L-configuration)
bridge = 4'-CH$_2$-O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

Natural and Modified Nucleobases

Antisense compounds of the present disclosure include oligonucleotides having nucleobase modifications or substitutions. As used herein, "unmodified" or "natural" nucleobases include the purine bases adenine (A) and guanine (G), and the pyrimidine bases thymine (T), cytosine (C) and uracil (U). Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to compounds described herein.

Modified nucleobases include other synthetic and natural nucleobases such as, for example, 5-methylcytosine (5-me- C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C☐C-CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Further modified nucleobases include tricyclic pyrimidines, such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as, for example, a substituted phenoxazine cytidine (e.g., 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one).

Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in U.S. Pat. No. 3,687,808, those disclosed in J. I. Kroschwitz (editor), The Concise Encyclopedia of Polymer Science and Engineering, pages 858-859, John Wiley and Sons (1990), those disclosed by Englisch et al. (1991), and those disclosed by Y. S. Sanghvi, Chapter 15: Antisense Research and Applications, pages 289-302, S. T. Crooke, B. Lebleu (editors), CRC Press, 1993.

Certain of these nucleobases are particularly useful for increasing the binding affinity of the oligonucleotide. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. In one embodiment, these nucleobase substitutions are combined with 2'-O-methoxyethyl sugar modifications.

Representative United States patents that teach the preparation of certain of the above noted modified nucleobases as well as other modified nucleobases include, but are not limited to, U.S. Pat. Nos. 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, 5,681,941 and 5,750,692.

In certain embodiments, compounds targeted to a PSMD9 nucleic acid comprise one or more modified nucleobases. In certain embodiments, the modified nucleobase is 5-methylcytosine. In certain embodiments, each cytosine is a 5-methylcytosine.

Conjugates

Antisense compounds of the present disclosure may be conjugated to one or more moieties or groups which enhance the activity, cellular distribution or cellular uptake of the antisense compound.

These moieties or groups may be covalently bound to functional groups such as primary or secondary hydroxyl groups.

Exemplary moieties or groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins and dyes.

Moieties or groups that enhance the pharmacodynamic properties include those that improve uptake, enhance resistance to degradation, and/or strengthen sequence-specific hybridization with the target nucleic acid.

Moieties or groups that enhance the pharmacokinetic properties include those that improve uptake, distribution, metabolism or excretion of the compounds of the present disclosure. Representative moieties or groups are disclosed in PCT/US92/09196 and U.S. Pat. No. 6,287,860. Moieties or groups include but are not limited to lipid moieties such as a cholesterol moiety, cholic acid, a thioether, for example, hexyl-S-tritylthiol, a thiocholesterol, an aliphatic chain, for example, dodecandiol or undecyl residues, a phospholipid, for example, di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Fatty acid modified gapmer antisense oligonucleotides are described for example in Hvam et al, *Molecular Therapy* 25(7) July 2017.

Chimeric Compounds

As would be appreciated by those skilled in the art, it is not necessary for all positions in a given compound to be uniformly modified and in fact, more than one of the aforementioned modifications may be incorporated in a single oligonucleotide or even at a single nucleoside within an oligonucleotide.

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

Certain embodiments disclosed herein provide a compound or composition comprising a modified oligonucleotide comprising: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine.

Antisense compounds of the disclosure include chimeric oligonucleotides. "Chimeric oligonucleotides" contain two or more chemically distinct regions, each made up of at least one monomer unit, that is, a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and if necessary, associated nucleic acid hybridization techniques known in the art.

Chimeric antisense compounds of the disclosure may be formed as composite structures of two or more oligonucleotides, modified oligonucleotides, and/or oligonucleotide mimetics. Such compounds have also been referred to in the art as hybrids or gapmers. Representative United States patents that teach the preparation of such hybrid structures include, but are not limited to, U.S. Pat. Nos. 5,013,830, 5,149,797, 5,220,007, 5,256,775, 5,366,878, 5,403,711, 5,491,133, 5,565,350, 5,623,065, 5,652,355, 5,652,356, and 5,700,922.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

Exemplary Oligonucleotides

Illustrative antisense platforms known in the art include without limitation, morpholino, lgen oligos, 2nd gen oligo's, gapmer, siRNA, LNA, BNA, or oligo mimetics like Peptide Nucleic acids. Oligonucleotides may be naked or formulated in liposomes. Oligonucleotides may be linked to a delivery means to cells or not. Oligonucleotides may use an endosome release agent or not.

Illustrative target specific siRNA to inhibit PSMD9 (Entrez Gene 5715 (human), SwissProt O00233 (human)) expression including human gene expression using RNA interference are available commercially, for example, from Cohesion Biosciences/Clinisciences (cat No. CRH3860), comprising 19-23 nucleotide siRNA synthetic oligonucleotide duplexes. Three different target specific siRNA are provided including 2'-OMe modification to provide enhanced stability and knockdown in vitro and in vivo.

PSMD9 sequences are described in publically available databases such as Genbank. A number of different variants are described by sequence. Variant 1 represents the longest transcript and encodes the longer isoform. The gene is conserved in mammalian species.

In one embodiment, the antisense compound is a second generation phosphorothioate backbone 2'-MOE-modified chimeric oligonucleotide gapmer designed to hybridize to the 3'-untranslated region of PSMD9 mRNA. In one embodiment, the oligonucleotide selectively inhibits PSMD9 expression in both primary human cells and in several human cell lines by hybridizing to RNA encoding PSMD9. In one embodiment the oligonucleotides inhibits expression of PSMD9 in the liver.

In one embodiment, all uracils are 5-methyluracils (MeU). Typically, the oligonucleotide is synthesized using 2-methoxyethyl modified thymidines not 5-methyluracils.

In one embodiment, all pyrimidines are C5 methylated (i.e., U, T, C are C5 methylated). In one embodiment, the sequence of the oligonucleotide may be named by accepted oligonucleotide nomenclature, showing each 0-0 linked phosphorothioate internucleotide linkage. In one embodiment, the PSMD9 antisense oligonucleotide has a nucleobase sequence comprising at least 8 contiguous nucleotide bases complementary to a PSMD9 polynucleotide sequence. In one embodiment, antisense oligonucleotides are complementary to at least 8 nucleotides from the 3'UTR, CDS and or 5'UTS or directed to at least one exon or one intron or a flanking region thereof.

In one embodiment, the PSMD9 inhibitor is an antisense oligonucleotide having 8 to 30 linked nucleosides having a nucleobase sequence comprising a complementary region comprising at least 8 contiguous nucleobases complementary to a target region of equal length within an exon of the PSMD9 transcript.

In one embodiment, the antisense oligonucleotide is a single stranded modified oligonucleotide. In one embodiment, the antisense olionucleotide is chimeric (such as a RNA:DNA).

In one embodiment the antisense oligonucleotide has at least one modified internucleoside linkage, sugar or nucleobase.

Illustrative antisense oligonucleotides comprise a central gap region of 8-14 DNA nucleotides adjoined on either end with 2'-O-methoxyethyl RNA (MOE) nucleotides and phosphorothioate (PS) backbone chemistry. See Teplova et al. Nat. Struct. Biol 1999, 6:535-539; Monia et al. J. Biol. Chem. 1993, 268:14514.

In one embodiment, the internucleoside linkage is a phosphorothioate internucleoside linkage, the modified sugar is a bicyclic sugar or 2'-O-methyoxyethyl and the modified nucleobase is a 5-methylcytosine.

Depending upon the length of the antisense oligonucleotide gapmers may comprise for example a 5-10-5 design, that is, five 2'-O-methoxyethyl nucleotides at the 5' end, 10 deoxynucleotides in the center, five 2'-O-methoxyethyl nucleotides at the 3' end, and phosphorothioate substitution throughout. 16mer gapmers may employ a 2-12-2, 3-10-3 or 4-8-4 design etc.

In one embodiment, the PSMD9 antisense oligonucleotide comprises a gap segment consisting of linked deoxynucleosides; a 5' wing segment consisting of linked nucleosides; and a 3' wing segment consisting linked nucleosides; wherein the gap segment is positioned immediately adjacent to and between the 5' wing segment and the 3' wing segment and wherein each nucleoside of each wing segment comprises a modified sugar.

In one embodiment, PSMD9 antisesne oligonucleotides are designed to referentially affect liver (see Sehgal et al J. Hepatology. 2013 59:1354-1359; Koller et al. Nucleic Acids Res. 20' 11:39:4795-4807; Prakash et al. J. Med. Chem. (2016), 59, 2718-2733.)

In one embodiment a series of chimeric 20-mer phosphorothioate antisense oligonucleotides containing 2'-O-methoxyethyl groups at positions 1 to 5 and 16 to 20 targeted to murine and human PSMD9 mRNA are synthesized and purified on an automated DNA synthesizer using phosphoramidite chemistry. In one embodiment the 3'/5' ends are locked nucleic acid or 2'O-methoxyethyl ribose.

In one embodiment the antisense oligonucleotide comprises a conjugated GalNAc. Triantennary N-acetylgalatosamine conjugated ASO. Such ASO are described for example by Prakash et al (above).

In one embodiment, the PSMD9 antisense inhibitor comprises: a gap segment consisting of 8 linked deoxynucleosides; (b) a 5' wing segment consisting of 4 linked nucleosides; (c) a 3' wing segment consisting 4 linked nucleosides; wherein the gap segment is positioned immediately adjacent to and between the 5' wing segment and the 3' wing segment, wherein each nucleoside of each wing segment comprises a 2'-O-methyoxyethyl sugar, wherein each cytosine is a 5'-methylcytosine, and wherein each internucleoside linkage is a phosphorothioate linkage. Other 16-mer gapmers will be designed in a 2-12-2 or 3-10-3 configuration as known in the art.

In one embodiment, the PSMD9 inhibitor antisense oligonucleotide is in a salt form.

In one non-limiting embodiment, the oligonucleotide may be synthesized by a multi-step process that may be divided into two distinct operations: solid-phase synthesis and downstream processing. In the first operation, the nucleotide sequence of the oligonucleotide is assembled through a computer-controlled solid-phase synthesizer. Subsequent downstream processing includes deprotection steps, preparative reversed-phase chromatographic purification, isolation and drying to yield the oligonucleotide drug substance. The chemical synthesis of the oligonucleotide utilizes phosphoramidite coupling chemistry followed by oxidative sulfurization and involves sequential coupling of activated monomers to an elongating oligomer, the 3'-terminus of which is covalently attached to the solid support.

Detritylation (Reaction a)

Each cycle of the solid-phase synthesis commences with removal of the acid-labile 5'-O-4, 4'-dimethoxytrityl (DMT) protecting group of the 5' terminal nucleoside of the support bound oligonucleotide. This is accomplished by treatment with an acid solution (for example dichloroacetic acid (DCA) in toluene). Following detritylation, excess reagent is removed from the support by washing with acetonitrile in preparation for the next reaction.

Coupling (Reaction b)

Chain elongation is achieved by reaction of the 5'-hydroxyl group of the support-bound oligonucleotide with a solution of the phosphoramidite corresponding to that particular base position (e.g., for base2: MOE-MeC amidite) in the presence of an activator (e.g., 1H-tetrazole). This results in the formation of a phosphite triester linkage between the incoming nucleotide synthon and the support-bound oligonucleotide chain. After the coupling reaction, excess reagent is removed from the support by washing with acetonitrile in preparation for the next reaction.

Sulfurization (Reaction c)

The newly formed phosphite triester linkage is converted to the corresponding [O, O, O)-trialkyl phosphorothioate triester by treatment with a solution of a sulfur transfer reagent (e.g., phenylacetyl disulfide). Following sulfurization, excess reagent is removed from the support by washing with acetonitrile in preparation for the next reaction.

Capping (Reaction d)

A small proportion of the 5'-hydroxy groups available in any given cycle fail to extend. Coupling of these groups in any of the subsequent cycles would result in formation of process-related impurities ("DMT-on (n-l)-mers") which are difficult to separate from the desired product. To prevent formation of these impurities and to facilitate purification, a "capping reagent" (e.g., acetic anhydride and N-methylimidazole/acetonitrile/pyridine) is introduced into the reactor vessel to give capped sequences. The resulting failure sequences ("DMT-off shortmers") are separated from the desired product by reversed phase HPLC purification. After the capping reaction, excess reagent is removed from the support by washing with acetonitrile in preparation of the next reaction.

Reiteration of this basic four-step cycle using the appropriate protected nucleoside phosphoramidite allows assembly of the entire protected oligonucleotide sequence.

Backbone Deprotection (Reaction e)

Following completion of the assembly portion of the process the cyanoethyl groups protecting the (O, O, O)-trialkyl phosphorothioate triester internucleotide linkages are removed by treatment with a solution of triethylamine (TEA) in acetonitrile. The reagent and acrylonitrile generated during this step are removed by washing the column with acetonitrile.

Cleavage from Support and Base Deprotection (Reaction f)

Deprotection of the exocyclic amino groups and cleavage of the crude product from the support is achieved by incubation with aqueous ammonium hydroxide (reaction f). Purification of the crude, 5'-O-DMT-protected product is accomplished by reversed phase HPLC. The reversed phase HPLC step removes DMT-off failure sequences. The elution profile is monitored by UV absorption spectroscopy. Fractions containing DMT-on oligonucleotide product are collected and analyzed.

Acidic Deprotection (Reaction g)

Reversed phase HPLC fractions containing 5'-O-DMT-protected oligonucleotide are pooled and transferred to a precipitation tank. The products obtained from the purification of several syntheses are combined at this stage of the process. Purified DMT-on oligonucleotide is treated with acid (e.g., acetic acid) to remove the DMT group attached to the 5' terminus. After acid exposure for the prescribed time and neutralization, the oligonucleotide drug substance is isolated and dried.

Following the final acidic deprotection step, the solution is neutralized by addition of aqueous sodium hydroxide and the oligonucleotide drug substance is precipitated from solution by adding ethanol. The precipitated material is allowed to settle at the bottom of the reaction vessel and the ethanolic supernatant decanted. The precipitated material is redissolved in purified water and the solution pH adjusted to between pH 7.2 and 7.3. The precipitation step is repeated. The precipitated material is dissolved in water and the solution filtered through a 0.45 micron filter and transferred into disposable polypropylene trays that are then loaded into a lyophilizer. The solution is cooled to −50° C. Primary drying is carried out at 25° C. for 37 hours. The temperature is increased to 30° C. and a secondary drying step performed for 5.5 hours. Following completion of the lyophilization process, the drug substance is transferred to high density polyethylene bottles and stored at −200° C.

Target Nucleic Acid

"Targeting" an antisense compound to a particular nucleic acid can be a multistep process. The targeting process usually also includes determination of at least one target region, segment, or site within the target nucleic acid for the antisense interaction to occur such that the desired effect, for example, inhibition of expression, will result. The term "region" as used herein is defined as a portion of the target nucleic acid having at least one identifiable structure, function, or characteristic. Within regions of the target nucleic acids are segments. "Segments" are defined as smaller or sub-portions of regions within a target nucleic acid. "Sites" as used herein, means positions within the target nucleic acid.

Since the "translation initiation codon" is typically 5'-AUG (in transcribed mRNA molecules; 5'-ATG in the corresponding DNA molecule), the translation initiation codon is also referred to as the "AUG codon", the "start codon" or the "AUG start codon". A minority of genes have a translation initiation codon having the RNA sequence 5'-GUG, 5'-UUG, or 5'-CUG, and 5'-AUA, 5'-ACG and 5'-CUG have been shown to function in vivo. Thus, the terms "translation initiation codon" and "start codon" can encompass many codon sequences even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. The terms "start codon" and "translation initiation codon" as used herein refer to the codon or codons that are used in vivo to initiate translation of an mRNA transcribed from a gene encoding.

A "translation termination codon" also referred to a "stop codon" may have one of three RNA sequences: 5'-UAA, 5'-UAG and 5'-UGA (5'-TAA, 5'-TAG and 5'-TGA, respectively in the corresponding DNA molecule). The terms "translation termination codon" and "stop codon" as used herein refer to the codon or codons that are used in vivo to terminate translation of an mRNA transcribed from a gene encoding PSMD9 regardless of the sequence(s) of such codons.

The terms "start codon region" and "translation initiation codon region" refer to a portion of the mRNA or gene that encompasses from about 25 to about 50 contiguous nucleotides in either direction (i.e., 5' or 3') from the translation initiation codon. Similarly, the terms and "stop codon region" and "translation termination codon region" refer to a portion of the mRNA or gene that encompasses from about 25 to about 50 contiguous nucleotides in either direction (i.e., 5' or 3') from the translation termination codon. Consequently, the "start codon region" or "translation initiation codon region" and the "stop codon region" or "translation termination codon region" are all regions which may be targeted effectively with the antisense compounds of the present disclosure.

The "open reading frame" (ORF) or "coding region", which is known in the art to refer to the region between the translation initiation codon and the translation termination codon, is also a region which may be targeted effectively. In one embodiment, the intragenic region encompassing the translation initiation or termination codon of the ORF of a gene is targeted.

Other target regions include the 5' untranslated region (5'UTR), known in the art to refer to the portion of the mRNA in the 5' direction from the translation initiation codon, and thus including nucleotides between the 5' cap site and the translation initiation codon of the mRNA (or corresponding nucleotides on the gene), and the 3' untranslated region (3'UTR), known in the art to refer to the portion of the mRNA in the 3' direction from the translation termination codon, and thus including nucleotides between the translation termination codon and 3' end of the mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself, as well as the first 50 nucleotides adjacent to the cap site. In one embodiment, the 5' cap region is targeted.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA transcripts produced via the process of splicing of two (or more) mRNAs from different gene sources are known as "fusion transcripts". In one embodiment, introns, or splice sites, that is, intron-exon junctions or exon-intron junctions, or aberrant fusion junctions due to rearrangements or deletions are preferentially targeted. Alternative RNA transcripts can be produced from the same genomic region of DNA. These alternative transcripts are generally known as "variants".

"Pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription, that is through use of an alternative start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. In one embodiment, the pre-mRNA or mRNA variants are targeted.

The location on the target nucleic acid to which the antisense compound hybridizes is referred to as the "target segment". As used herein the term "target segment" is defined as at least an 8-nucleobase portion of a target region to which an antisense compound is targeted. While not wishing to be bound by theory, it is presently believed that these target segments represent portions of the target nucleic acid which are accessible for hybridization.

Once one or more target regions, segments or sites have been identified, antisense compounds are chosen which are sufficiently complementary to a target segment, that is, antisense compounds that hybridize sufficiently well and with sufficient specificity, to give the desired effect.

The target segment may also be combined with its respective complementary antisense compound to form stabilized double-stranded (duplexed) oligonucleotides. Such double stranded oligonucleotide moieties have been shown in the art to modulate target expression and regulate translation, as well as RNA processing via an antisense mechanism. Moreover, the double-stranded moieties may be subject to chemical modifications (Fire et al., 1998; Timmons and Fire, 1998; Timmons et al., 2001; Tabara et al., 1998; Montgomery et al., 1998; Tuschl et al., 1999; Elbashir et al., 2001a; Elbashir et al., 2001b). For example, such double-stranded moieties have been shown to inhibit the target by the classical hybridization of antisense strand of the duplex to the target, thereby triggering enzymatic degradation of the target (Tijsterman et al., 2002).

Compositions

Antisense compounds of the disclosure may be admixed, encapsulated, conjugated or otherwise associated with other molecules, molecule structures or mixtures of compounds, resulting in, for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921, 5,354,844, 5,416,016, 5,459,127, 5,521,291, 5,543,158, 5,547,932, 5,583,020, 5,591,721, 4,426,330, 4,534,899, 5,013,556, 5,108,921, 5,213,804, 5,227,170, 5,264,221, 5,356,633, 5,395,619, 5,416,016, 5,417,978, 5,462,854, 5,469,854, 5,512,295, 5,527,528, 5,534,259, 5,543,152, 5,556,948, 5,580,575, and 5,595,756.

Antisense compounds of the disclosure may be administered in a pharmaceutically acceptable carrier. The term "pharmaceutically acceptable carrier" refers to molecular entities that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, solvents, surfactants, excipients, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the disclosure.

In one embodiment, the pharmaceutical carrier is water for injection (WFI) and the pharmaceutical composition is adjusted to a physiologically and functionally acceptable.

In one embodiment, the salt is a sodium or potassium salt.

The oligonucleotides may contain chiral (asymmetric) centers or the molecule as a whole may be chiral. The individual stereoisomers (enantiomers and diastereoisomers) and mixtures of these are within the scope of the present disclosure.

Antisense compounds of the disclosure may be pharmaceutically acceptable salts, esters, or salts of the esters, or any other compounds which, upon administration are capable of providing (directly or indirectly) the biologically active metabolite.

The term "pharmaceutically acceptable salts" as used herein refers to physiologically and pharmaceutically acceptable salts of the antisense compounds that retain the desired biological activities of the parent compounds and do not impart undesired toxicological effects upon administration. Examples of pharmaceutically acceptable salts and their uses are further described in U.S. Pat. No. 6,287,860.

Antisense compounds of the disclosure may be prodrugs or pharmaceutically acceptable salts of the prodrugs, or other bioequivalents. The term "prodrugs" as used herein refers to therapeutic agents that are prepared in an inactive form that is converted to an active form (i.e., drug) upon administration by the action of endogenous enzymes or other chemicals and/or conditions. In particular, prodrug forms of the antisense compounds of the disclosure are prepared as SATE [(S acetyl-2-thioethyl) phosphate] derivatives according to the methods disclosed in WO 93/24510, WO 94/26764 and U.S. Pat. No. 5,770,713.

A prodrug may, for example, be converted within the body, e. g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference. Those skilled in the art of organic chemistry will appreciate that many organic compounds can form complexes with solvents in which they are reacted or from which they are precipitated or crystallized. These complexes are known as "solvates". For example, a complex with water is known as a "hydrate".

Administration

In one embodiment, the antisense compound of the disclosure is administered systemically. As used herein "systemic administration" is a route of administration that is either enteral or parenteral.

As used herein "enteral" refers to a form of administration that involves any part of the gastrointestinal tract and includes oral administration of, for example, the antisense oligonucleotide in tablet, capsule or drop form; gastric feeding tube, duodenal feeding tube, or gastrostomy; and rectal administration of, for example, the antisense compound in suppository or enema form.

As used herein "parenteral" includes administration by injection or infusion. Examples include, intravenous (into a vein), intraarterial (into an artery), intramuscular (into a muscle), intracardiac (into the heart), subcutaneous (under the skin), intraosseous infusion (into the bone marrow), intradermal, (into the skin itself), intrathecal (into the spinal canal), intraperitoneal (infusion or injection into the peritoneum), intravesical (infusion into the urinary bladder), intraperitoneal. Transdermal (diffusion through the intact skin), transmucosal (diffusion through a mucous membrane), inhalational.

In one embodiment, administration of the pharmaceutical composition is subcutaneous. The antisense compound may be administered as single dose or as repeated doses on a period basis, for example, daily, once every two days, three, four, five, six seven, eight, nine, ten, eleven, twelve, thirteen or fourteen days, once weekly, twice weekly, three times weekly, or every two weeks, or every three weeks.

In one embodiment administration is 1-3 times per week, or once every week, two weeks, three weeks, four weeks, or once every two months.

Illustrative doses are between about 10 to 200 mg. Illustrative doses include 5, 10, 20, 25, 50, 100, 150, 200, 250, 500, 1000, 1500, 2000, 2500 mg. Illustrative doses include 1.5 mg/kg (about 50 to 100 mg) and 3 mg/kg (100-200 mg) and 4.5 mg/kg (150-300 mg). Further illustrative doses include 5 mg/kg, 10 mg/kg, 15 mg/kg, 20 mg/kg, 25 mg/kg (13 to 2500 mg), 30 mg/kg, 35 mg/kg or 50 mg/kg daily, weekly, monthly, bi-weekly or bi-monthly.

The term "therapeutically effective amount" as used herein refers to a dose of the antisense compound sufficient for example to improve one or more markers, signs or symptoms of dysregulated hepatic lipid metabolism, or other conditions associated therewith.

In another embodiment, the administration is effective to provide a Cmax of the oligonucleotide in the plasma of a test or mammalian or human subject upwards of 2000 ng/mL.

In another embodiment, the administration is effective to provide a Cmin or Ctrough of the oligonucleotide in the plasma of the human subject of at least 1-2 ng/mL.

Polynucleotides Encoding Peptides or Polypeptides

In one embodiment, the polynucleotide PSMD9 modulator encodes a polypeptide so that delivery of the polynucleotide leads to expression of the modulator in a suitable cell. Dominant negative inhibitors are known in the art and are contemplated herein.

In one embodiment, the polynucleotide PSMD9 modulator encodes a programmable nuclease which inhibits PSMD9 activity by inactivating or reducing expression of psmd9 gene. Programmable nucleases include RNA guided engineered nucleases derived from CRISPR-cas, ZFN, TALEN and argonaute nucleases. Such targeted nucleases are particularly useful for modulating PSMD9 in cells ex vivo.

In one embodiment, the polynucleotide is provided in an expression vector to be delivered in vivo to a subject or in vitro to a cell or tissue. Transfection methods are known in the art. A vector may be a viral vector or a non-viral vector as known in the art. For example, viral vectors include lentiviral, retroviral, adenoviral, herpes virus and adeno-associated viruses known in the art. Non-viral vectors include plasmids, transposon-modified polynucleotides (such as the MVM intron), lipoplexes, polymersomes, polyplexes, dendrimers, inorganic nanoparticles, cell penetrating peptides and combinations thereof. A new class of vectors acts by passive permeabilization of the plasma membrane. It includes peptides, streptolysin O, and cationic derivatives of polyene antibiotics. Promoters including minimal promoters and other regulatory elements which may be tissue specific (such as the minimal TTRm promoter among others known in the art specific for the liver) will be apparent to the skilled person in the art from the teaching provided herein. Non-limiting examples of liver-specific regulatory elements are disclosed in WO 2009/130208, which is specifically incorporated by reference herein.

In another embodiment, the polynucleotide PSMD9 modulator is a synthetic chemically modified RNA that encodes a dominant negative PSMD9. Typically, chemically modified mRNAs comprise (i) a 5' synthetic cap for enhanced translation; (ii) modified nucleotides that confer RNAse resistance and an attenuated cellular interferon response, which would otherwise greatly reduce translational efficiency; and (iii) a 3' poly-A tail. Typically, chemically modified mRNAs are synthesized in vitro from a DNA template comprising an SP6 or T7 RNA polymerase promoter-operably linked to an open reading frame encoding the dominant-negative CIS. The chemically modified mRNA synthesis reaction is carried in the presence of a mixture of modified and unmodified nucleotides. In some embodiments modified nucleotides included in the in vitro synthesis of chemically modified mRNAs are pseudo-uridine and 5-methyl-cytosine. A key step in cellular mRNA processing is the addition of a 5' cap structure, which is a 5'-5' triphosphate linkage between the 5' end of the RNA and a guanosine nucleotide. The cap is methylated enzymatically at the N-7 position of the guanosine to form mature mCAP. When preparing dominant-negative PSMD9 chemically modified mRNAs, a 5' cap is typically added prior to transfection of cells ex vivo in order to stabilize the modified mRNA and significantly enhance translation. Systems for in vitro synthesis are commercially available, as exemplified by the mRNAExpress™ mRNA Synthesis Kit (System Biosciences, Mountain View, Calif). The general synthesis and use of such modified RNAs for in vitro and in vivo transfection are described in, e.g., WO 2011/130624, and WO/2012/138453.

Administration of the PSMD9 modulators described herein as pharmaceutical or physiological compositions will vary depending upon various factors appreciated by the skilled person and will depend upon the type of agent used. Therapeutically effective amounts are derived by the skilled person using only routine experimentation which includes but is not limited to dose escalation studies. The required dose may conveniently be presented as a single dose or as divided doses administered over appropriate intervals. The dose may vary with the dose form and route of administration used. Compositions can be formulated for administration to a subject by any conventional means including oral, parenteral, buccal, inhalation, rectal or transdermal administration routes. Any suitable dosage formulation can be employed and these are art recognized to include a wide range of materials that aid in stability and distribution including controlled release formulations.

PSMD9 modulators may be identified using art recognized screening tools, such as, for example, ELISA-type assays, FRET and time resolved-FRET assays, bead based assays followed by MALDI spectrometry to name a few. Alternatively biochemical assays or cell based screens such as protein complementation, two hybrid assays are used to probe potential protein interactions.

In silico screening assays are described in the prior art for identifying potentially interacting elements and molecules from three dimensional molecule databases which can then be modified to enhance interactions. Design of peptides and analogues, derivatives and mimetics is described in the literature, see, for example Bryan et al. Peptides 2011, 32(12):2504-2510.

In accordance with the present description the inventors have conducted a comprehensive analysis of the proteomes and lipidomes of livers from 107 mouse strains (307 mice in total) from the HMDP, with the aim of identifying post-genomic contributions to the complexities of hepatic function and lipid metabolism. The approach advantageously uses a pair-wise analysis of proteome and lipidome abundance in the exact same liver, of the exact same mouse from an inbred genetic panel. This allows for an unprecedented, individualized interrogation of protein:lipid cross talk, that eliminates the residual variability observed by other studies when analysing strain averaged data. Subsequent bioinformatics integration of proteomic and lipidomic data produced a rich resource to functionally characterise protein:lipid networks. The approach permits investigation of hepatic lipid metabolism in the context of arguably one of the most relevant biological effectors, proteins, which is independent of genetic QTL mapping, transcriptomics and environmental modulation. To the inventor's knowledge, a trans-omic analysis of hepatic lipid metabolism to this depth has not been performed.

Hepatic lipidomic studies have not previously been performed and the present description provides a much needed transomics approach which as described herein has led to identifying the observed genetic variability in particular hepatic lipids and the associated molecular pathways that are instrumental in the development of polygenic metabolic conditions such as fatty liver disease, hepatosteatosis, and dyslipidemia.

Between strains, dramatic and consistent variation in protein and lipid abundance in the liver was observed, enabling confident bioinformatics integration and identification of highly correlated protein:lipid pathways. This included a previously unappreciated inter-play between proteostasis and acylglycerol accumulation, and identified PSMD9 as a critical regulator of pathological lipid accumulation in the liver. Reference to "pathological lipids" includes one or more lipid species from a lipid class selected from acyl glycerols, diacylglycerol (DG) and triacylglycerol (TG), phosphatidylcholine (PC), phosphatidylethanolamine (PE), cholesteryl ester (CE) and ceramide (Cer) or their variants (e.g., dihexosylceramide (DHC)).

PSMD9 is a PDZ domain containing protein found associated with the proteasome and lipids, which has also been identified as a transcriptional regulator and receptor. As determined herein PSMD9 is a key regulator of the liver lipidome whose modulation permits favourable in vivo lipid remodelling (i.e., reduction in pathological lipid accumulation).

As determined herein, overexpression of PSMD9 (human or mouse) in the mouse liver, identified PSMD9 as a key regulator of pathological lipid accumulation in the liver or plasma.

As determined herein, administration of modulators of PSMD9 is effective to prevent or treat or avoid the accumulation of pathological lipids in the subject, or a cell or tissue of a mammalian subject.

Accordingly, the present description enables a method for treating a subject suffering from hepatic lipid dysregulation or at risk of suffering from same, comprising administering a PSMD9 modulator to the subject.

As used herein, the term "subject" means any animal including humans, for example a mammal Exemplary subjects include but are not limited to humans and non-human primates. For example, the subject is a human Reference to a subject includes a cell or tissue of the subject. In one embodiment, the subject has been identified as suffering from fatty liver or hepatosteatosis or as at risk from fatty liver or hepatosteatosis. In one embodiment, the subject has been previously tested for pathological lipid accumulation known in the art or as disclosed herein. Testing may take place on a biological sample from the subject.

The term "hepatic lipid dysregulation" includes early stage lipid dysregulation such as elevated pathological lipids. As determined herein this early stage may be identified by assessing the level of pathological lipids (e.g., one or more of DG, TG, PC, PE, CE and/or DHC). The term also encompasses fatty liver disease also referred to as hepatosteatosis and non-alcoholic fatty liver disease and in some embodiments to its pathological sequalae.

In one embodiment, the PSMD9 modulator is in the form of a pharmaceutical or physiological composition comprising the PSMD9 modulator.

In one embodiment, the PSMD9 modulator is administered for a time and under conditions sufficient to modulate the activity of PSMD9 in a subject or cell of a subject.

In one embodiment, the PSMD9 modulator is administered for a time and under conditions or sufficient to decrease or normalise the level of pathological lipid species, such as acylglycerols in the subject.

In one embodiment, the PSMD9 modulator is or comprises a peptide, a peptidomimetic, a small molecule, a polynucleotide, or a polypeptide.

In one embodiment, the PSMD9 modulator is an inhibitor of PSMD9 expression.

In one embodiment, PSMD9 activity is determined by evaluating the level or activity of a protein whose expression is correlated with PSMD9 expression in a liver cell as determined herein.

In one embodiment, PSMD9 activity is determined by evaluating the level of PSMD9 polypeptide in a cell or subject.

In one embodiment, PSMD9 activity is evaluated by determining the binding interaction to a binding site such as the PDZ domain of PSMD9.

In one embodiment, the peptide is a phosphopeptide or phosphomimetic.

In one embodiment, the polypeptide comprises an anti-PSMD9 antibody or an antigen binding fragment thereof.

In one embodiment, the PSMD9 modulator is a polynucleotide. Polynucleotide sequences include oligonucleotides.

Oligonucleotide modulators are known in the art and/or are as described herein. In one embodiment, oligonucleotides comprise sequences complementary or substantially complementary to at least one PSMD9 nucleotide sequence. PSMD9 nucleotide and amino acid sequences are known in the field, include variants including variants for multiple species, and are identified in publically available sequence databases. Illustrative PSMD9 sequences are described in the sequence listing.

In one embodiment, the polynucleotide is an antisense oligonucleotide.

In one embodiment, the antisense oligonucleotide is about five, six, seven, eight, nine, 10, 11, 12, 13, 14, 15, 16, 17, 18, 19, 20, 21, 22, 23, 24, 25, 26, 27, 28, 29, 30 nucleotides or more in length.

In one embodiment the PSMD9 modulator is an inhibitory oligonucleotide selected from an isolated or synthetic antisense RNA or DNA, siRNA or siDNA, miRNA, miRNA mimics, shRNA or DNA and chimeric antisense DNA or RNA. In one embodiment, the inhibitory RNA is selected from a shRNA, gRNA siRNA, miRNA, miRNA mimic or chimeric antisense RNA.

In one embodiment, the polynucleotide is a vector for the expression of the PSMD9 modulator.

In one non-limiting embodiment, the modulator is a dominant negative modulator comprising PSMD9 or a non-functional variant thereof that does not upregulate the level of pathological lipids in the subject or liver. In another embodiment, the modulator is a chemically modified RNA encoding a non-functional variant.

In one embodiment, the vector is a viral vector or a non-viral vector. Any suitable viral or non-viral vector may be employed. An adenoviral associated or non-viral vector, for example, is useful for administering to the liver.

In one embodiment, the hepatic lipid dysregulation is fatty liver disease or NAFLD. In one embodiment, the hepatic lipid dysregulation comprises upregulation of pathological lipid species as described herein.

In one embodiment, the description enables the use of a PSMD9 modulator in the manufacture or preparation of a medicament for use in the treatment or prevention of hepatic lipid dysregulation in a subject.

In one embodiment, the description enables a PSMD9 modulator for use or when used in the treatment of hepatic lipid dysregulation in a subject. In one embodiment the hepatic lipid dysregulation is fatty liver disease (steatosis) or non-alcoholic or alcoholic fatty liver disease.

The present description employs methods and material including the following: ASOs were designed and synthesized by Ionis Pharmaceuticals. Chimeric 16-mer phosphorothioate oligonucleotides targeted to mouse Psmd9 (5'-CTCTATGGGTGCCAGC-3') or control sequences (5'-GGCCAATACGCCGTCA-3') were synthesized and purified as described by Seth, P. P. et al. Synthesis and biophysical evaluation of 2',4'-constrained 2'O-methoxyethyl and 2',4'-constrained 2'O-ethyl nucleic acid analogues. The Journal of organic chemistry 75, 1569-1581, doi: 10.1021/jo902560f (2010). In the first study, ASOs were delivered by intraperitoneal injection (I.P.) twice weekly to chow-fed 8-week old C57BL/6J or DBA/2J mice (Jackson Labs) at a dose of 25 mg/kg for 1 week, and one group of mice were also treated with PBS (Vehicle, n=4 mice/group). Livers were analysed by proteomics and lipidomics for changes in protein and lipid abundance. In the second study, male C57BL/6J and DBA/2J mice were treated with vehicle (PBS), control ASO or Psmd9 ASO at 25 mg/kg by IP injection, twice weekly. Mice were treated for 4 weeks, and fed a Western diet for the same period (Research Diets D12079B) (n=8 mice/group). Mice were culled and tissues and plasma were harvested for lipidomic analysis as well as Western Blotting and qPCR. For the third study, male C57BL/6J and DBA/2J mice were fed a Western diet for 4 weeks and treated with either vehicle (PBS, n=6/group), control ASO (n=6/group) or Psmd9 ASO (n=8/group) at 25 mg/kg by IP injection weekly. Body weight and composition (determined by NMR, Bruko) were measured weekly, and food intake was monitored in the final 2 weeks. For the final week of diet, mice were provided with 5% deuterium oxide (Sigma) in the drinking water before tissues were harvested. Plasma ALT and AST were analysed using a commercial kit according to the manufacturer's instructions (TECO Diagnostics).

HMDP Animals

All mice were originally obtained from The Jackson Laboratory and were subsequently bred and housed at University of California, Los Angeles to generate offspring used in this study as previously described (Parks et al., 2013; Parks et al., 2015). Male mice were maintained on a chow diet (Ralston Purina Company) until 8-10 weeks of age before being fasted for 16-hours in a bedding free cage. All protocols for these studies were approved by the Institutional Care and Use Committee (IACUC) at University of California, Los Angeles. DBA mice exhibit much higher levels of DG compared to C57B16/J (C57) mice models.

Proteomics

Liver proteomic sample preparation: Frozen liver (10 mg) was homogenised in 6 M urea, 2 M thiourea, 50 mM triethylammonium bicarbonate (TEAB) pH 8.0 containing protease inhibitor cocktail (Roche; 11873580001) by tip-probe sonication and centrifuged at 16,000×g, 10 min at 4° C. Lysates were precipitated with 6 volumes of acetone overnight at −30° C. Protein pellets were centrifuged at 10,000×g, 10 min at 4° C. resuspended in 6 M urea, 2 M thiourea, 50 mM TEAB, pH 7.9 and quantified by Qubit fluorescence (Thermo Fisher; Q33212). Concentrations were normalized and 100 µg of protein reduced with 10 mM dithiothreitol (DTT) for 60 min at 25° C. followed by alkylation with 25 mM iodoacetamide (IAA) for 30 min at 25° C. in the dark. The reaction was quenched to a final concentration of 20 mM dithiothreitol and digested with lysyl endopeptidase Lys-C(Wako Pure Chemical Industries; 125-05061) at 1:50 enzyme to substrate ratio for 2 h at 25° C. The mixture was diluted 5-fold with 25 mM TEAB and digested with trypsin (Promega; V5111) at 1:50 enzyme to substrate ratio for 16 h at 30° C. The peptide mixture was acidified to a final concentration of 2% formic acid, 0.1% trifluoroacetic acid (TFA) and centrifuged at 16,000×g for 15 min. Peptides were desalted using hydrophilic lipophilic balance—solid phase extraction (HLB-SPE) 96-well plates (Waters; 186000128) followed by elution with 50% acetonitrile, 0.1% TFA and dried by vacuum centrifugation. For proteomic analysis of the HMDP by TMT multiplexing, peptides were resuspended in 30 µl of 250 mM TEAB, pH 8.5 quantified by Colorimetric Peptide Assay (Thermo Fisher; 23275) and normalized to 10 µg/10 µl. Peptides were labelled with 10-plex Tandem Mass Tags according to the manufacturer's instructions (Thermo Fisher; 90110; lot PI202555). Each 10-plex experiment contained 9 different strains with a tenth reference label (either 126 or 131 isobaric label) made up of the same peptide digest from pooled mix of C57BL/6J livers. A list of the sample labelling strategy and replicates is available in PRIDE proteomeXchange. Peptides were labelled in a final concentration of 50% acetonitrile for 90 min at room temperature followed by de-acylation with 0.25% hydroxylamine for 15 min at room temperature and quenching with 0.1% TFA. Peptides from each 10-plex experiment were pooled and desalted using HLB-SPE and dried by vacuum centrifugation. Approximately 12 µg of peptide was fractionated into 9 fractions on an in-house packed TSKgel amide-80 HILIC column as previously described (Palmisano et al., 2010). For proteomic analysis of adenovirus transduced livers by label-free quantification (LFQ), purified peptides were resuspended in 2% acetonitrile, 0.1% TFA quantified by Qubit and normalized to 1 µg/3 µl.

Proteomic liquid chromatography—tandem mass spectrometry: TMT-labelled peptides were analyzed on a Dionex 3500RS nanoUHPLC coupled to an Orbitrap Fusion mass spectrometer in positive mode. For proteomic analysis of the HMDP livers by TMT multiplexing, peptides were separated using an in-house packed 75 µm×40 cm pulled column (1.9 µm particle size, C18AQ; Dr Maisch, Germany) with a gradient of 2-30% acetonitrile containing 0.1% FA over 100 min at 250 nl/min at 55° C. An MS1 scan was acquired from 350-1400 m/z (120,000 resolution, 4e5 AGC, 50 ms injection time) followed by MS/MS data-dependent acquisition with CID and detection in the ion trap (1e4 AGC, 70 ms injection time, 30% normalized collision energy, 1.6 m/z quadrupole isolation width). Multi-notch isolation of the top 10 most intense MS/MS ions from 400-1000 m/z excluding the precursor ion and neutral loss clusters <40 m/z were subjected to MS3 with HCD and detection in the orbitrap (1e5 AGC, 200 ms injection time, 55% normalized collision energy, 2 m/z ion trap isolation width, 100-500 m/z) (McAlister et al., 2014). For proteomic analysis of adenovirus infected livers by LFQ, peptides were separated using an in-house packed 75 µm×50 cm pulled column (1.9 µm particle size, C18AQ; Dr Maisch, Germany) with a gradient of 2-30% acetonitrile containing 0.1% FA over 180 min at 300 nl/min at 55° C. An MS1 scan was acquired from 300-1500 m/z (60,000 resolution, 5e5 AGC, 50 ms injection time) followed by MS/MS data-dependent acquisition with HCD and detection in the orbitrap (1e5 AGC, 60 ms injection time, 30% normalized collision energy, 1.6 m/z quadrupole isolation width).

Proteomic Data Analysis: TMT labelled data were processed with Proteome Discoverer (v2.1) using Sequest (Eng et al., 1994). The precursor MS tolerance were set to 20 ppm and the MS/MS tolerance was set to 0.6 Da with a maximum of 2 miss-cleavage. The peptides were searched with oxidation of methionine set as variable modification, and TMT tags on peptide N-terminus/lysine and carbamidomethylation of cysteine set as a fixed modification.

All data were searched as a single batch with peptide spectral matches and protein false discovery rate set to 1%. Quantification was performed with the reporter ion quantification node for TMT quantification in Proteome Discoverer. TMT precision was set to 10 ppm and corrected for isotopic impurities. Only spectra with <50% co-isolation interference were used for quantification with an average signal-to-noise filter of >10. LFQ data were processed with MaxQuant (v1.5.3.30) using Andromeda (Cox and Mann, 2008) against the UniProt mouse or human databases.

Lipidomics

Sample Preparation: Liver tissue was cryomilled, suspended in PBS, sonicated and ~50 ug/10 ul transferred to a fresh tube, whilst 10 uL of plasma was used. Samples were processed and analysed by MRM LC-MS/MS as previously described (Alshehry et al., 2016).

A detailed description of the method is as follows. Lipidomic analysis was performed by liquid chromatography electrospray ionisation tandem mass spectrometry on an Agilent 1290 liquid chromatography system, utilizing Mass Hunter software. Liquid chromatography was performed on a Zorbax Eclipse Plus 1.8 μm C18, 50×2.1 mm column (Agilent Technologies). Solvents A and B consisted of tetrahydrofuran:methanol:water in the ratio (30:20:50) and (75:20:5) respectively, both containing 10 mM ammonium formate. Columns were heated to 50° C. and the autosampler regulated to 25° C. Lipid species (1 μL injection) were separated under gradient conditions at a flow rate of 400 μL/min. The gradient was as follows; 0% solvent B to 40% solvent B over 2.0 min, 40% solvent B to 1000% solvent B over 6.5 min, 0.5 min at 100% solvent B, a return to 0% solvent B over 0.5 min then 0.5 min at 0% solvent B prior to the next injection (total run time of 10 min).

The mass spectrometer was operated in dynamic/scheduled multiple reaction monitoring (dMRM) mode. There were 310 unique lipid species measured together with 15 stable isotope or non-physiological lipid standards. Mass spectrometer voltages used for the acquisition of data were; fragmentor voltage, 380 V and cell accelerator voltage, 5 V. The collision energy voltage was set individually for each lipid class and subclass. Acquisition windows were set to between 0.7 and 1.76 min depending on the chromatographic properties of the lipid. Further, there were several sets of isobaric lipid species which shared the same nominal parent ion mass and also give rise to the same product ions. Specifically, for isobaric species of PC, PC(O) and PC(P) the parent and product ions (m/z 184) the same. As a result a single MRM transition was used to measure the corresponding species within each subclass, using an increased MRM window time (22 combinations). Additionally there were eight occurrences of isobaric PE, PE(O) and PE(P) lipid species, representing the neutral loss of 141 Da, which were similarly combined into a single dMRM transition. Analysis of triacylglycerols was based on single ion monitoring. To perform this analysis in the dynamic/scheduled multiple reaction monitoring (dMRM) mode both Q1 and Q3 were set to the [M+NH4]+ values for each triacylglycerol species and the collision energy was reduced to 5 V to minimise collision induced dissociation.

While most lipid classes and subclasses have similar response factors for lipid species within the class, some classes show greater variation in response factors between species and consequently, correction factors were applied for some lipid classes. Diacyl- and triacylglycerol (DG and TG): Fragmentation of the ammoniated adducts of DG and TG leads to the loss of ammonia and a fatty acid. In this context it is important to recognize that for species which contain more than one of the same fatty acid, the loss of that fatty acid will result in an enhanced signal, as it is the end product from two competing pathways. Consequently, where an MRM transition was used that corresponded to the loss of a fatty acid that was present more than once, this was divided by the number of times that fatty acid was present.

Cholesteryl ester (CE): Response factors were determined with seven commercially available species and used to create a formula to extrapolate for all CE chain lengths and double bonds. Saturated species were characterized by the following relationship: $y=0.1486x-1.5917$, where y is the response factor relative to the CE 18:0 d 6 internal standard and x is the carbon chain length. For monounsaturated species, the response factor was multiplied by 1.84 and for polyunsaturated species by 6.0. Phosphatidylinositol (PI): A single response factor was calculated for all PI species to account for the use of the PE 17:0/17:0 as the internal standard for this lipid class. A nine point standard curve was created using commercially available PI 32:0 and subsequently spiked into solvent containing a fixed concentration of PE 17:0/17:0. The standard curve resulted in a linear response and indicated a response factor of 1.44 for phosphatidylinositol species relative to phosphatidylethanolamine standard Other lipid species were not corrected.

Quality Control Samples: Two types of quality control samples were utilized in this study. Plasma from six healthy volunteers was pooled and split into multiple aliquots. These samples are referred to as plasma quality control (PQC) samples. These samples are then subjected to extraction and LC-MS analysis alongside samples from the study to provide a measure of analytical variability across the study as a whole. Additionally identical lipid extracts were utilised, which were prepared by pooling the lipid extracts from multiple PQC samples using this mixture to prepare multiple aliquots which were referred to as technical quality control (TQC) samples. Analysis of these samples captures only the variation associated with the LC-MS performance. Within the analytical process every twenty-five plasma samples a PQC and TQC were included.

Data pre-processing: In this study, HMDP liver samples were run in two batches. An extraction batch consisted of ~200 samples each including PQC, TQC and blanks A median centering approach was used for correction of the batch effect. The median PQC concentration of each lipid for each batch was used as a reference point to align the samples with the entire cohort. The alignment was performed by calculating a correction factor to adjust the concentration of each PQC lipid in each batch to the median value for all batches.

Bioinformatics & Data analysis—Biweight midcorrelations were performed using R and q-values estimated using a ranked Benjamini-hochberg multiple comparison test with significance quoted $q<0.05$. Proteomic and lipidomic comparisons following modulation of Psmd9 and ACAD11 AP-MS were compared to respective controls using either 2-way t-tests or ANOVA and p-value data presented as permutation-based FDR corrected with significance quoted at p<0.05. To perform unsupervised hierarchical clustering of the HMDP proteomes and lipidomes, data was first median-centred and the similarity of each strain was assessed using Euclidean distance metric. Hierarchical clustering with complete agglomeration method was then applied to cluster strains with respect to their global profiles. To identify plasma lipid signatures to predict liver lipid, we computed pairwise ratios of plasma lipids. Given the large number of plasma lipid ratios and the much smaller mice sample size (p>>n), we applied a two-step approach to identify from all plasma lipid ratios the ones that are potentially predictive to the total amount of the six liver lipid classes (CE, Cer, DG, TG, COH, PE(P)). In the first step, we filtered plasma lipid ratios using their Pearson's correlation with the total amount of the liver lipids by retaining the top-10% most correlated ratios for each of the six liver lipid class. In the second step, we employed a clustering-based representative feature selection approach 22 to identify a set of diverse and representative plasma lipid ratios from all remaining lipids after step 1. This procedure leads to a reduction of plasma lipid ratios from 29403 to ~50 for each of the six liver lipid classes. Lastly, we utilised a Lasso regression approach with a repeated (10 times) 5-fold cross-validation procedure to test the predictive capability of the selected plasma lipid ratios for the total amount of each of the six liver lipid class. This prediction procedure leads to 50 prediction results that were referred to as "trails". We classified the predictability of each of the six liver lipid into high, median, and low based on the significance of models fitted on plasma lipid ratios in the 50 trails. The results of these tests were classified into high (100%), median (50-100%) or low (<50%) predictability based on the number of trials that passed significance (p<0.05) of the fitted model. Circos plot (Krzywinski, M. et al. Circos: an information aesthetic for comparative genomics. Genome research 19, 1639-1645, doi:10.1101/gr.092759.109 (2009)). was used to visualise the three way genetic interaction between SNPs, proteins, and lipid species. KEGG and gene ontology (GO) analysis was performed using The Database for Annotation, Visualization and Integrated Discovery (DAVID v6.8) hosted by the National Institute of Allergy and Infectious Diseases (NIAID), NIH, USA. Briefly, target lists were generated from external analyses and then entered as a gene list in DAVID. Background adjustment was enabled against the *Mus musculus* reference gene set and functional annotation clustering was performed with the classification stringency set at medium and p-value data presented as Benjamin Hochberg corrected. Network analysis was performed in Cytoscape and integrated data from the HINT and BioGRID databases and protein complexes from the CORUM database.

QTL mapping of proteins and Lipid—Datasets of liver lipidomics, proteomics or plasma lipids were mapped for association of each SNP using a linear mixed model. While minimum threshold of 50 strains was used as a requirement for detection of each protein for correlation analysis, both the entire lipidome (liver and plasma) as well as nearly 2500 proteins were detected in all 307 mice. We applied an efficient mixed-model association (fast-lmm) to identify SNPs associating with indicated traits as described below:

$$y = \ln \mu + x\beta + u + e$$

n=the number of individuals,
μ=the mean
β=the allele effect of the SNP
x is the (nxl) vector of observed genotypes of the SNP.

This model takes population structure into account, as "u" is the random effects due to genetic relatedness with var(u)=σ2uK and "e" denotes the random noise with var(e)=σ2eI. Here, "K" indicates the identity-by-state kinship matrix estimated using all SNPs, "I" represents the (nxn) identity matrix and "ln" is the (nxl) vector of ones. σ2u and σ2e were estimated using restricted maximum likelihood (REML) and computed p-values using the standard F-test to test the null hypothesis where β=0. Genome-wide significance threshold and genome-wide association mapping were determined as the family-wise error rate as the probability of observing one or more false positives across all SNPs for a given phenotype. To correct for false discovery, q-values were estimated from the distribution of p-values using the linear mixed model from the R package "qvalue" as previously described 11. This model has been tested rigorously, and the HMDP used to elucidate many validated QTLs for quantitative traits 13,40,41,54,55, including liver lipid species and protein levels. Significance was calculated at q-value <0.1 (cis-p-QTL=+/−10 Mb of the gene, approximated local adjusted p-value <1e-04; 1-QTLs=approximated global adjusted p-value <4.2e-6).

Cell Cultures and Treatments

HEK293 cells obtained from ATCC were maintained in DMEM+10% FBS. Transfections: Cells were plated onto cell culture treated plates or onto acid stripped coverslips at 60% confluence in growth media in the morning. Later that day cells were transfected with 500 ug of the appropriate plasmids using FuGene6 according to the manufacturer's instructions. 24-48 hours later cells were harvested for downstream processing (western blot/fractionation/proteomics) or fixed and mounted for confocal imaging.

Cloning & Expression Vectors

PCR amplification of genes of interest was performed from cDNA as previously described (Drew et al., 2014) using Phusion DNA polymerase (Thermofisher). Human PSMD9 and acad11 were cloned from Hep3B cDNA, whilst mouse PSMD9 was cloned from mouse liver cDNA. Amplified open reading frames were cloned into expression vectors using gateway technology or RE reactions (pDEST-47 GFP, C-term 3xFLAG, pAd-V5, Invitrogen). Expression vectors were sequence verified and subsequently amplified and purified by midi-prep (Promega) before use in downstream protocols. Fluorescently tagged organelle constructs were purchased from AddGene (plasmid #1817: Lamp1-RFP, #54503: DsRed2-Peroxisomes-4 and #58014: mTagRFP-T-Endosomes-14).

Confocal Imaging

Cells were plated and transfected as described above. When ready, cells were washed, fixed in 10% formalin for 30 minutes and then washed again before briefly storing in PBS. Coverslips were mounted on the stage of a Nikon Alr-Plus SI NIR Modified inverted scanning confocal microscope, covered with PBS and imaged using a 60x water immersion lens. Images were captured using NIS-Elements software and post-capture images were processed and standardized using image J software.

Immunoblot Analysis

Cells or tissue samples were homogenized in RIPA lysis buffer containing freshly added protease (complete EDTA-Free, Roche) and phosphatase inhibitors (Sigma) as previously described. Resolved proteins were transferred to PVDF membranes and subsequently probed with the following antibodies: PSMD9 (Sigma), cyp2c44 (Santa Cruz Biotech), β-actin (Cell Signalling Technologies), ACAD11 (invitrogen), porin/VDAC1 (mitosciences), pex14

(proscitech), pan 14-3-3 (Santa Cruz Biotech). Densitometric analysis was performed using BioRad Quantity One software.

Quantitative RT-PCR

Tissues were homogenized in RNAzol reagent and RNA was isolated by addition of BCP and precipitated in isopropanol (Drew et al., 2015). RNA was pelleted and washed twice in 70% ethanol and then resuspended in molecular grade water. cDNA synthesis was performed using 1 μg of RNA with M-MLV reverse transcriptase (Thermofisher). Quantitative real time PCR reactions were prepared using iTaq Fast SYBR Green Supermix (Biorad) with 10-20 ng of cDNA template and performed on an ABI Fast 7500 real time detection system. Quantification of a given gene, expressed as relative mRNA level compared with control, was calculated using the ddCT method after normalization to a standard housekeeping gene (36B4/rplp0 or cyclophillin A/ppia).

High Fat Diet fed mice—Male C57BL/6J mice were fed a chow or HFD (SF04-001, Specialty Feeds) for 12 weeks prior to plasma and liver collection in accordance with the AMREP Animal Ethics Committee at the Baker Heart & Diabetes Institute.

Adenovirus in Mice

Human PSMD9 (hPSMD9) and mouse PSMD9 (mPSMD9) (specifically the polynucleotide having the sequences set out in SEQ ID NO: 5 and its counterpart CDS from man) were cloned as described above and shuttled into adenoviral expression vectors (pAd. The generation of pAd-mPSMD9, pAd-Cont, pAd-hPSMD9 and pAd-GFP was carried out as previously described (de Aguiar Vallim et al., 2015; Marquart et al., 2010). Adenovirus particles were prepared using the AdEasy system (Agilent) or Virapower system (Invitrogen) and purified by CsCl gradient centrifugation. The virus was dialyzed for 48 hours and stored at −80° C. Particles were quantified by serial dilution methods by detection of plaques in HEK293A cells. Male C57BL/6J and DBA/2J mice (Jackson Labs, 8 week old) were injected with 109 plaque forming units (PFU) of adenovirus via tail vein injection. Livers and plasma were collected 5-7 days post-infection after a 4-5 hour fast.

Example 1

Multi-Layered Proteomic and Lipidomic Diversity of the Mouse Liver

To define the molecular basis of hepatic lipid metabolism, a quantitative proteomic and lipidomic analysis was performed of livers from 107 male strains of the HMDP (n=2-3/strain, 307 livers in total) (FIG. 1A). Every mouse was housed in the identical environment, fed the same chow diet and fasted for 16 h prior to analysis. Proteomic analysis was undertaken on livers by performing tandem mass tag (TMT) 10-plex LC-MS/MS experiments with synchronous precursor selection (SPS-MS3) acquisition that provides highly accurate relative quantification (McAlister et al., 2014). Each 10-plex experiment included a reference of pooled livers from C57BL/6J to normalize between each experiment. Proteomics analysis quantified a total of 5,453 proteins with 2,933 proteins quantified in >150 livers, and 1,671 proteins quantified in the liver of all mice in the entire study. Targeted lipidomics analysis was performed on the exact same cryo-milled sample of liver with multiple reaction monitoring (MRM) acquisition, which quantified 311 species of lipids across 23 classes (Alshehry et al., 2015).

To demonstrate the depth and accuracy of the datasets, proteome and lipidome variation was investigated and the inventors demonstrated that the average technical, intra- and inter-strain variation of the proteomics data was 6.4, 10.4 and 14.6%, respectively; while the lipidomics data was 8.6, 32.2 and 42.8%, respectively (FIG. 1B). As can be observed, the technical variation was <10% in each dataset, highlighting the reproducibility of the mass-spectrometry measurements across time and individual experiments. A notable difference in the variances is observed in the intra- and inter-strain variability (intra: 10.4 vs 32.2% and inter: 14.6 vs 42.8% for proteomics and lipidomics respectively). For the lipidomic analysis, 311 species were measured across 101 strains (n=3) using targeted MRM, which selects lipids based on scientific value, which is completely independent of their abundance. In this case many of these lipids may be of low abundance and thus more variable simply because they are closer to the threshold of detection. The quantitative performance of the data was further assessed by unsupervised hierarchical clustering. The proteomics and lipidomics data clustered 278/307 (90%) and 125/292 (43%) individual livers into their biological replicates of each strain, respectively (FIG. 1C). The fidelity of this analysis further suggests excellent technical and intra-strain reproducibility.

To further corroborate the robustness of the datasets, the inter-strain variation of liver proteins determined from the above analysis was compared to the liver proteomes of previously published collections of genetically diverse mouse strains including the BxD (Williams et al., 2016) and Diversity Outbred datasets (Chick et al., 2016) (FIG. 1D). This process identified proteins that varied considerably in their expression level but consistently across all three mouse collections. This confirmed the accuracy and reproducibility of all three datasets across different proteomic platforms and collections of genetically diverse mice.

Targeted analysis of the lipidome revealed considerable heterogeneity both in the relative abundance between individual lipids species in the same class (i.e. diacylglycerols), and the relative abundance between different strains. The dynamic range in the abundance of a select sub-group of specific lipid species is highlighted in FIG. 1E, which plots the average abundance of individual lipid species (log 2 μmol/μmol PC) for each strain as individual points, with the box plot depicting the inter-strain variation. These data demonstrate that some species including dihydroceramides (dhCer, blue boxes) are in the range of approximately 5 μmol/μmol PC, while specific diacylglycerols (DGs) are found at much higher levels (red boxes) of approximately 50 mmol/μmol PC. The boxplots indicate substantially more variation in the triacylglycerol (TG) species (purple boxes) across the strains than was observed for other lipids such as the ceramides (light blue boxes), which showed little variation across all HMDP strains. In fact, the level of total TGs and DGs varied by 27-fold and 6-fold across all 107 strains, respectively (FIG. 1F), which is notable considering all mice were of the same gender and age, fed normal chow diet and were housed and fasted under the exact same conditions. The abundance of total TG generally correlated with the abundance of total DG for each strain, however there were some strains where this was not the case. The level of total TG in the livers of several strains, was similar to that routinely observed in C57BL6/J mice fed a high fat diet (HFD) for 12 weeks. This is an important comparison considering that this is presumably a mostly genetic driven effect in the HMDP strains, and that C57BL6/J mice fed a HFD for this period of time are substantially obese and display clinically detectable hepatic steatosis. As mentioned above, there were some lipid species that were more tightly regulated than others, including total ceramides (Cer) and total unesterified cholesterol (COH), which displayed an approximately two-fold or less difference across all strains. These data potentially indicate that genetic diversity likely plays a major role in controlling the absolute level of specific lipid species that are important for sustenance (i.e. TG), whilst others fluctuate minimally due to their fundamental role in cellular processes and the many processes in place to maintain homeostasis. Indeed, COH is one of the most fundamental lipids in all cells and is an important building block for several other metabolites and for maintaining cell membrane integrity. Nevertheless, genetic variation amongst HMDP strains clearly contributes to large differences in many hepatic lipid species, and is thus an ideal platform for the investigation of biochemical pathways that regulate these lipids.

To identify protein networks that associate with hepatic lipid abundance, weighted correlation network analysis (WCNA) (Langfelder and Horvath, 2008) was performed on the proteomes of all 307 livers, and nine significant modules of co-regulated proteins were identified. Pathway enrichment analysis performed on these modules using KEGG and Gene Ontology (GO), was used to identify the pathways that these modules represent. Next, the eigenvector of these modules was correlated against all 311 individual lipid species to enable a broad overview of the pathways potentially associated with individual lipids or entire lipid classes. There was a strong and consistent correlation of the acylglycerol classes (DG and TG) with several of the modules (both positive and negative), that was more discernible than that of other classes such as the ceramides (Cer) and other sphingolipids (SL). Because of this consistent class effect with the acylglycerols, and the fact there was significant variation in these lipids across the HMDP as described above, subsequent analyses focused on TG and DGs.

The majority of DG/TG species, correlate positively with modules that contain a strong enrichment for mitochondrial and lipid metabolic processes. Interestingly, several protein modules displayed a negative correlation with the majority of DG/TG species, which were enriched in protein synthesis pathways (translation and ribosome) and protein degradation pathways (ubiquitin ligases, deubiquitinases and proteasome). This initial overview supports a previously described expansion of peroxisomes and mitochondrial activity to enable greater lipid handling Unexpectedly where was negative interplay between proteostasis and hepatic DG/TG content. It is important to note that the abundance and metabolism of specific lipid species differs amongst the lipid species within the same class.

Figure 2:
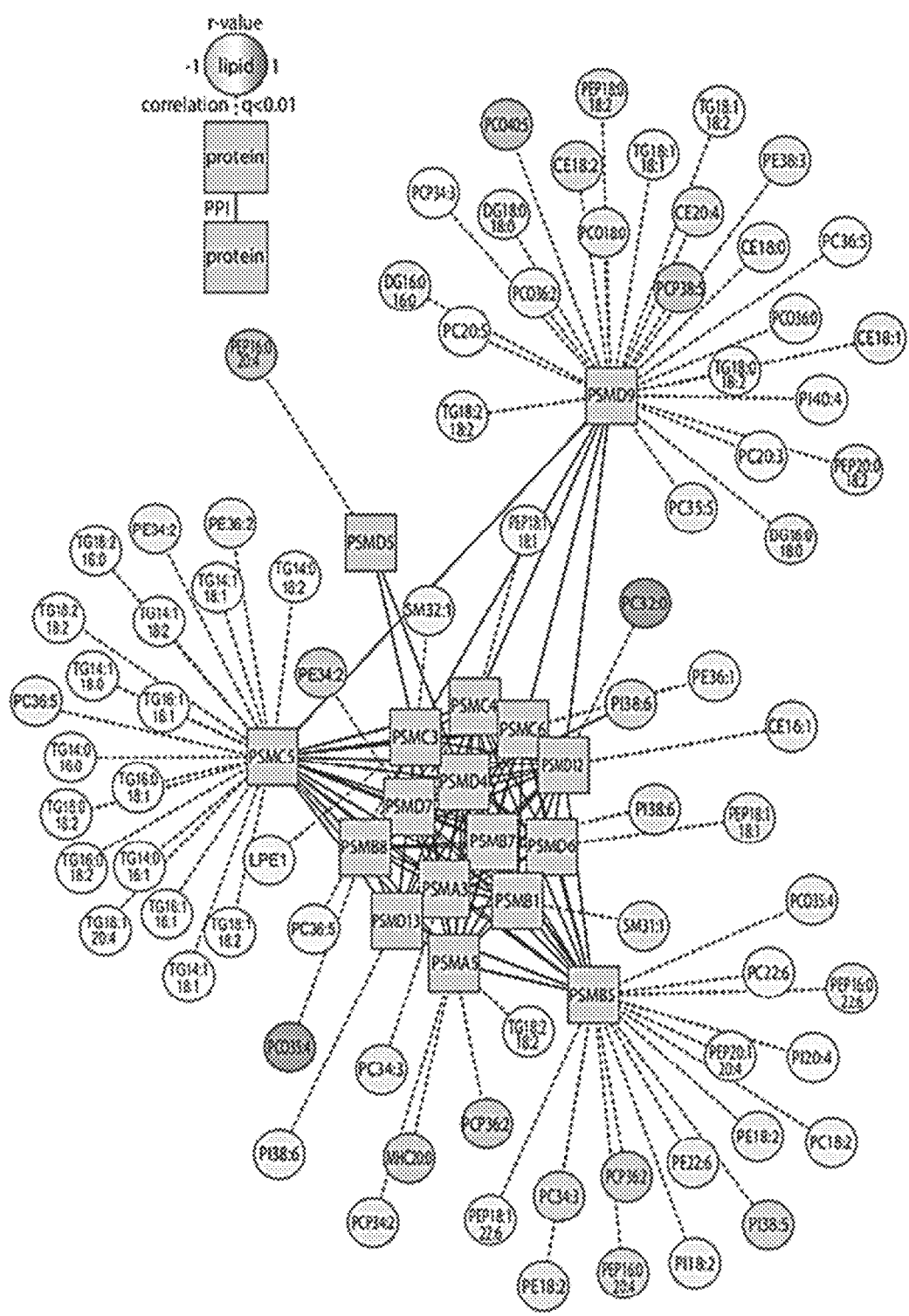
FIG. 2 illustrates associations of the proteasome showing experimentally observed protein:protein interactions (PPIs) (solid lines) and significant protein:lipid correlations (dotted lines) (Pearson correlation, q-value<0.01 Benjamin Hochberg FDR).
Figure 5:
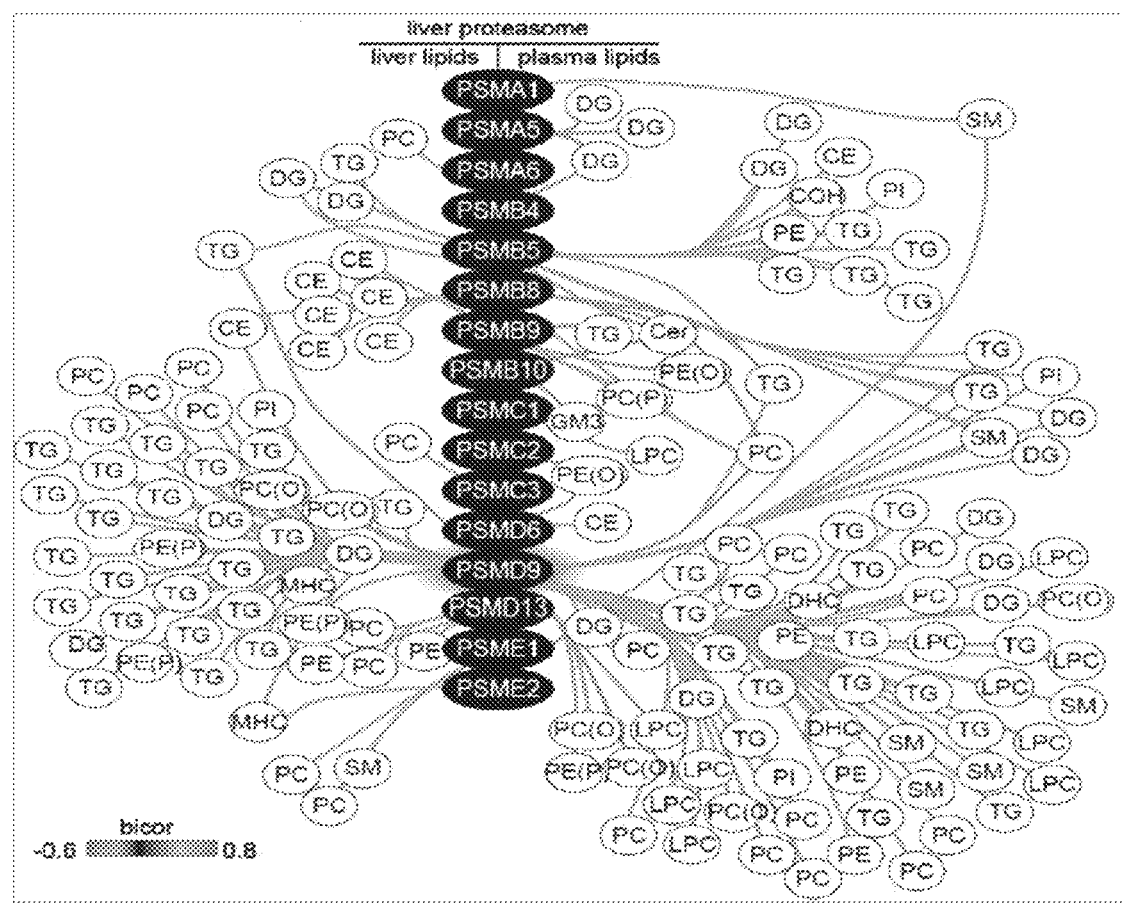
FIG. 5 | Proteasomal proteins including PSMD9 are correlated with lipid abundance. a, Biweight midcorrelation (bicor) of proteasome associated proteins against 530 significantly correlated (FDR corrected, q<0.05—orange=positive, aqua=negative) liver 531 lipid species (left) and plasma lipid species (right) (n>50 strains). Individual lipid species 532 designated by class only are as follows: cholesterol ester (CE), ceramide (Cer), free 533 cholesterol (COH), diacylglycerol (DG), monohexosylceramide (MHC), phosphatidylcholine (PC), alkylphosphatidylcholine (PC(O)), lysophosphatidylcholine (LPC), phosphatidylethanolamine (PE), alkenylphosphatidylethanolamine (PE(P)), sphingomyelin (SM), triacylglycerol (TG). b, Back to back Manhattan plot demonstrating a significant ($p<1e-4$) cis-pQTL for PSMD9 protein abundance on chromosome 5, co-mapping to a significant lQTL ($p<4.2e-06$) for plasma TG 14:0 16:1 18:2 abundance (bottom) (n=105 strains). Inset summarises that SNPs on chromosome 5 (chr5) drive variation in PSMD9 protein abundance and plasma TG/DG abundance, corroborated by a direct correlation (P:L, bicor, q<0.05) between hepatic PSMD9 protein and plasma DG and TG abundance. c, Box and whisker plots (median=black bar, upper and lower quartiles=open boxes, whiskers=extremes) demonstrating that homozygous allelic variation (AA versus GG) at the SNP rs29770398 within the PSMD9 locus, significantly associates ($p<3e-6$) with abundance of plasma TG species (n=105 strains).
Figure 5:
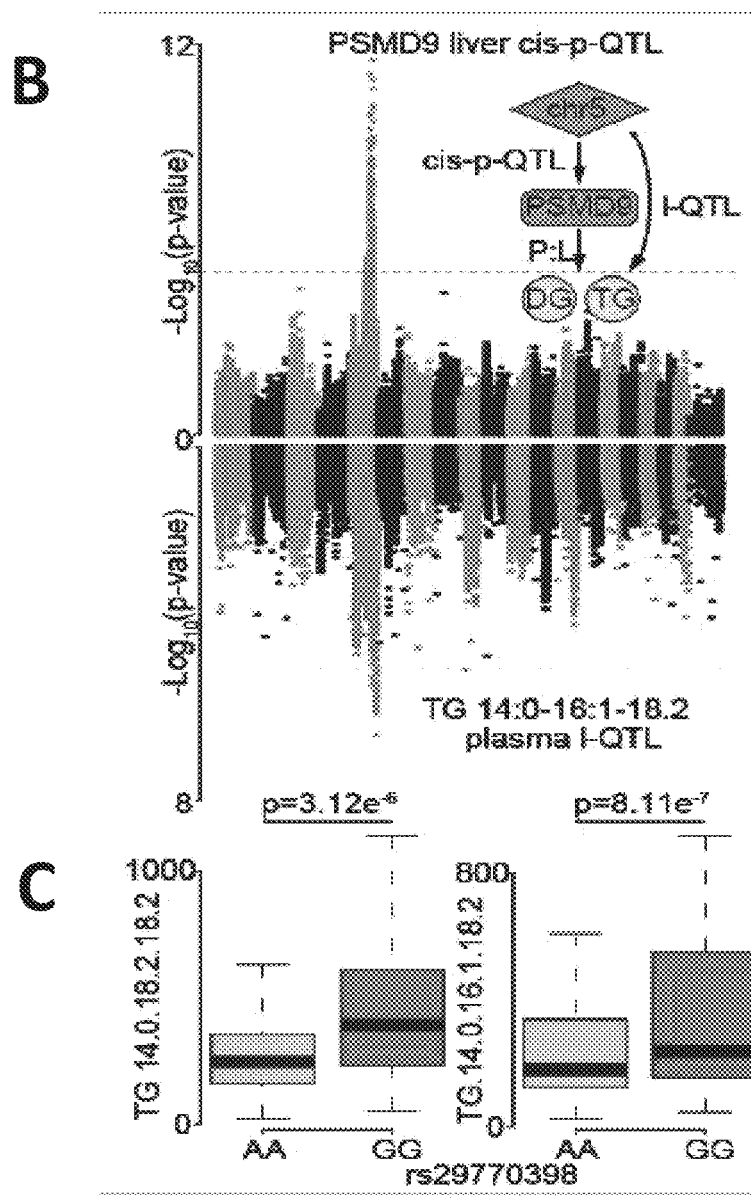

To identify specific proteins involved in these pathways each individual lipid species was correlated with every protein quantified across the set of HMDP livers, resulting in pair-wise analysis of 1.12 million lipid:protein correlations (n=307) across the entire platform. A total of 13,455 individual lipid:protein correlations were significant spanning 1,552 proteins (q<0.01, Benjamini Hochberg FDR). Pathway enrichment analysis of these 1500 proteins using KEGG revealed significant enrichment of proteins involved in energy metabolism pathways. To further benchmark the data for known positive regulators of lipid metabolism, the inventors focused on individual proteins associated with the acylgyercols. However, consistent with the WCNA analysis, proteostasis pathways including proteins associated with the ribosome and proteasome were also negatively associated. Several enzymes involved in protein synthesis were negatively correlated with both total DG and TG levels. A total of 88 significant correlations were identified between individual lipid species and proteasome subunits. Of note were three proteasomal proteins in particular of which the first, PSMC5, is an ATPase of the 26S regulatory subunit of the proteasome. PSMC5 was negatively correlated almost entirely with TG species (18/21), but not at all with any DG species, which was surprising given that the vast majority of proteins correlated with total TG levels were also correlated with total DG. Furthermore, PSMB5 was also negatively associated with 15 lipids, none of which were acylglycerols. Paradoxically, a specific positive correlation with several lipid species was observed for PSMD9, a non-ATPase component of the base complex of the 19S regulatory subunit of the proteasome. PSMD9 was positively correlated with 26 lipid species including DG, TG, PC, PE and CE (FIG. 2). Further studies have shown PSMD9 is positively correlated with 39 lipid species in the liver and negatively correlated with 65 lipids in the plasma (FIG. 5a). Furthermore, QTL mapping identified significant cis-pQTLs at the PSMD9 locus, which also harboured several lQTLs for plasma TG species (FIG. 5b). This indicates that genetic variation at the PSMD9 locus drives changes in PSMD9 protein abundance and TG levels in the plasma. This is further supported by evidence that allelic variation (AA>GG) at the peak SNP within the PSMD9 pQTL (r529770398) associates with a significant 2-fold change in plasma TG species (TG 14:0 247 18:2 18:2 and TG 14:0 16:1 18:2)(FIG. 5c).

Example 2

Overexpression of Psmd9 in the Liver Promotes Accrual of Pathological Lipid Species Linked to Fatty Liver Disease and Insulin Resistance The trans-omic methods described herein highlighted a complex association between the metabolism of a variety of lipid classes and proteostasis. Of particularly interest was the in the positive association of PSMD9 and esterified lipids. PSMD9 is annotated as proteasome (prosome, macropain) 26S subunit, non-ATPase 9, owing to its original discovery and identification as being associated with the proteasome (Watanabe et al., 1998). However, studies have suggested other functional roles for PSMD9 including transcriptional regulation and receptor activity in proteasomal function.

Figure 3:
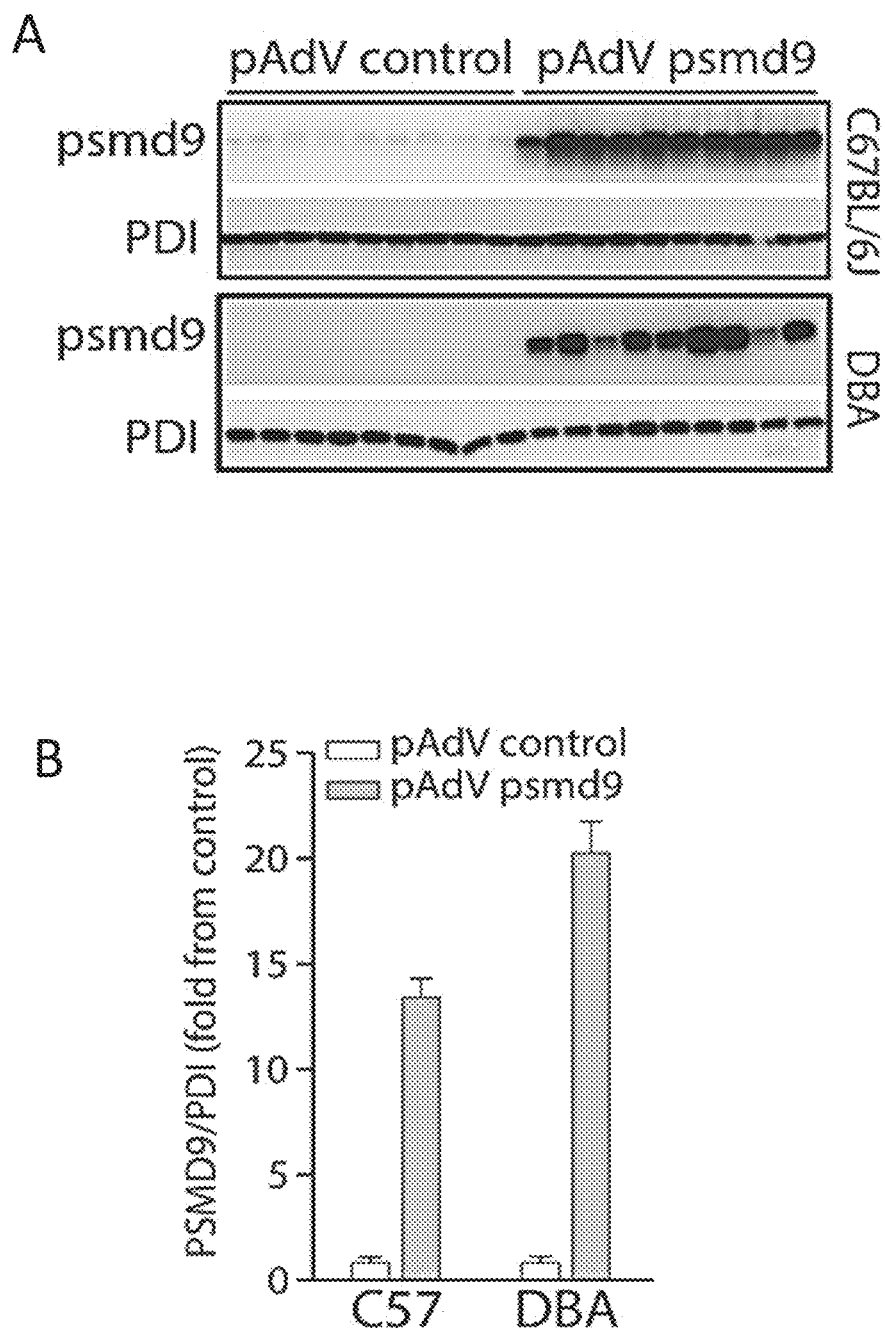
FIGS. 3A and B illustrate the relative mRNA expression levels of psmd9 in the liver of C57B16/J (C57) and DBA/2J mice 5 days following adenovirus (pAdV) administration. Normalized to pdi. (*p-value<0.05, **p-value<0.01 t-test, mean±SEM).

The inventors next sought to determine if the significant positive protein:lipid correlations identified from the platform were merely a consequence of increased lipid concentrations, or whether these proteins directly act to modulate the abundance of specific lipids. Adenoviruses were administered to over-express Psmd9 in both C57B16/J and DBA/2J mice. PSMD9 showed its strong positive association with several pathological lipid species and was a unique target relating to the identified proteostasis pathway. Experiments were performed in two different genetic backgrounds to investigate potential strain specific modifier effects, but also to examine changes regardless of endogenous lipid levels (acyl glycerols in the plasma of DBA/2J mice are approximately 5 times higher than that observed in C57B16/J). At seven days post transduction, Psmd9 mRNA expression in the liver of C57B16/J mice was ~14-fold higher than controls; and in the liver of DBA/2J Psmd9 mRNA expression was ~20-fold higher than controls (FIG. 3A). This level of expression of Psmd9 lead to robust protein over-expression with ~14-fold and ~21-fold fold increases in C57B16/J and DBA/2J mice, respectively (FIG. 3B). Overexpression achieved through tail vein injection of adenovirus (which we have shown targets the liver (de Aguiar Vallim et al., 2015)) is proposed to affect lipid accumulation and storage directly in the liver and/or result in global accumulation of lipids in the circulation. Targeted lipidomic quantification was therefore performed in both the liver and plasma of adenovirus treated mice.

Figure 4:
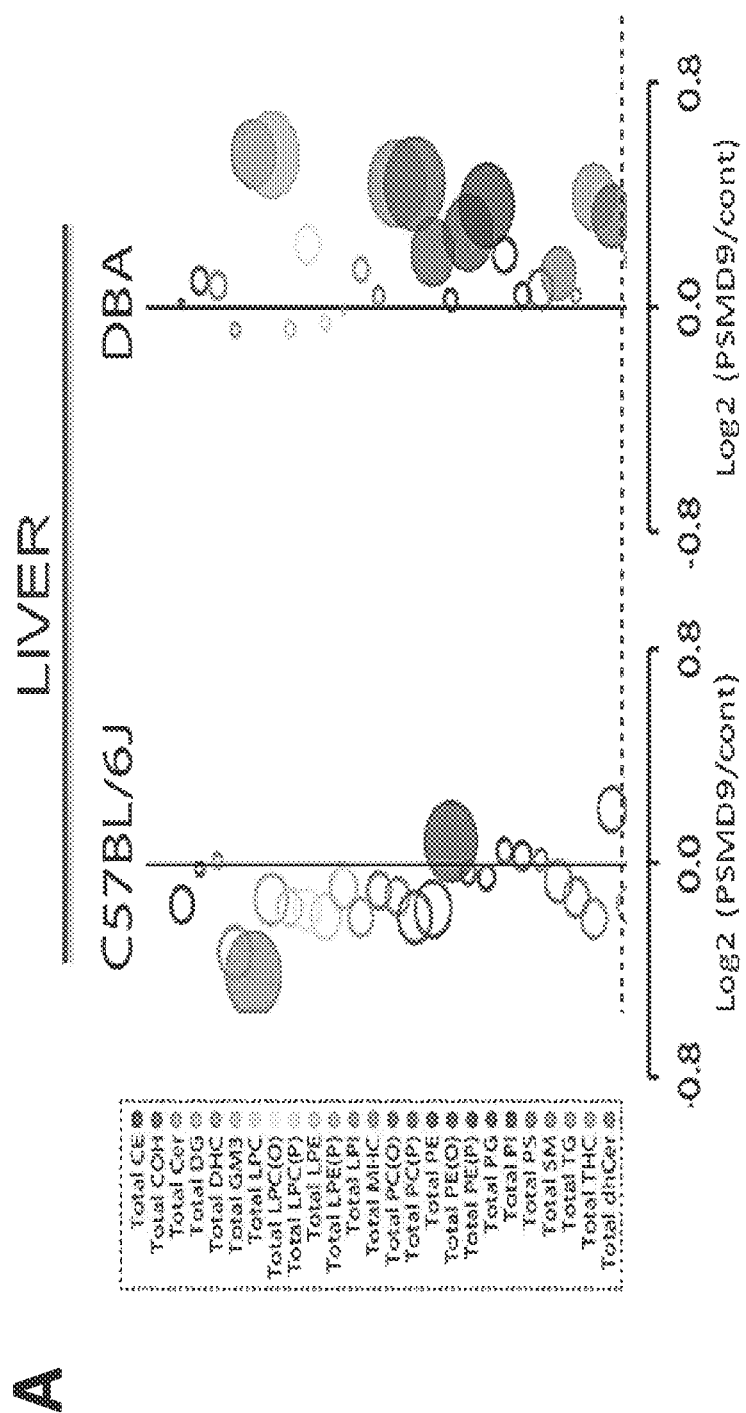
FIG. 4 is a bubble plot depicting relative lipid levels in the liver and plasma of C57B16/J and DBA/2J mice following psmd9 pAdV administration: (A)=totals for each lipid class in liver (colour key shown in dotted box), (B) top=individual diacylglycerols in liver (green bubbles), bottom=individual triacylglycerols in liver (blue bubbles), (C) top=totals for each lipid class in the plasma, middle=individual diacylglycerols in plasma, and bottom=individual triacylglycerols in plasma. Open circles q-value>0.05, closed circles q-value<0.05, t-test with Permutation-based FDR. Bubble size is reflective of significance of change in abundance (key top left).
Figure 4:
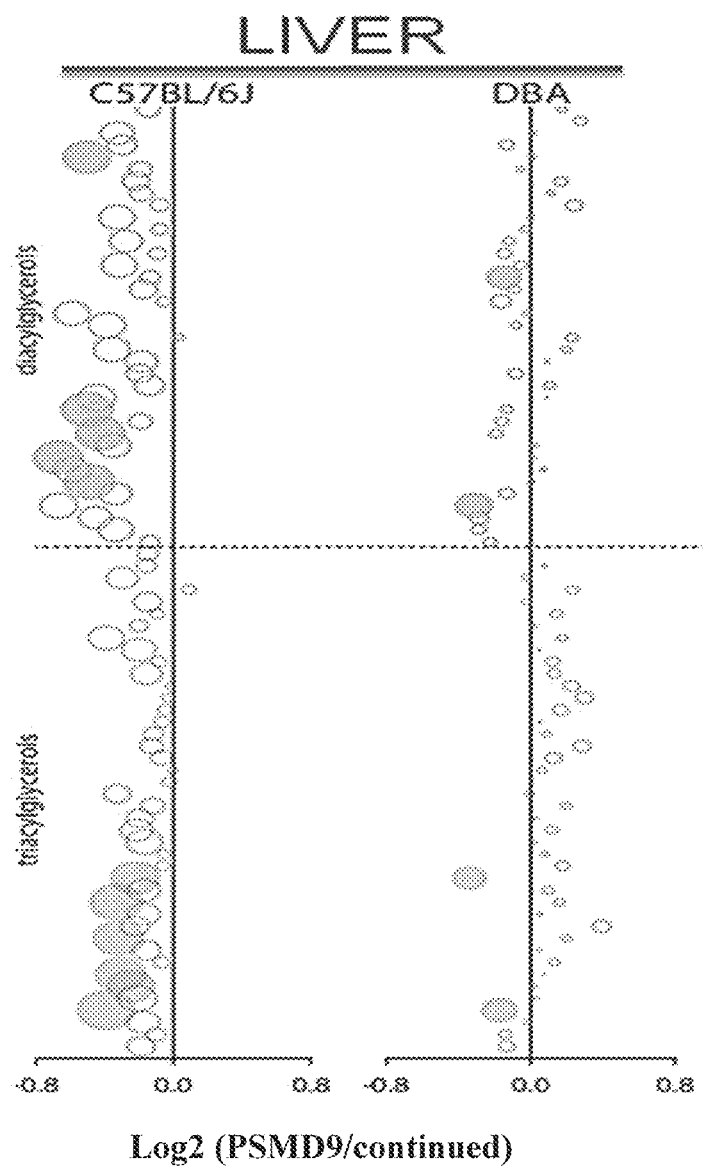
Figure 4:
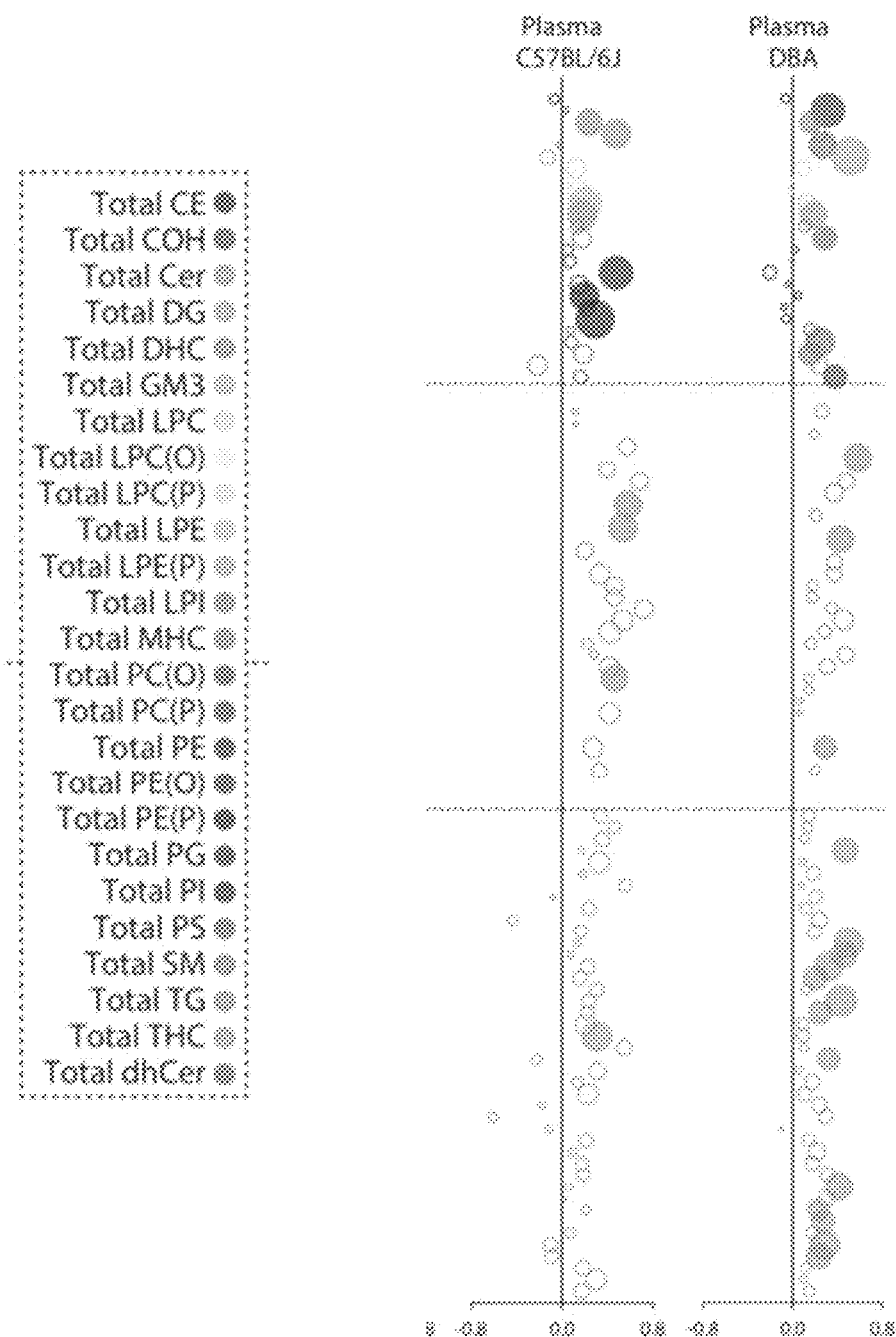
Figure 6:
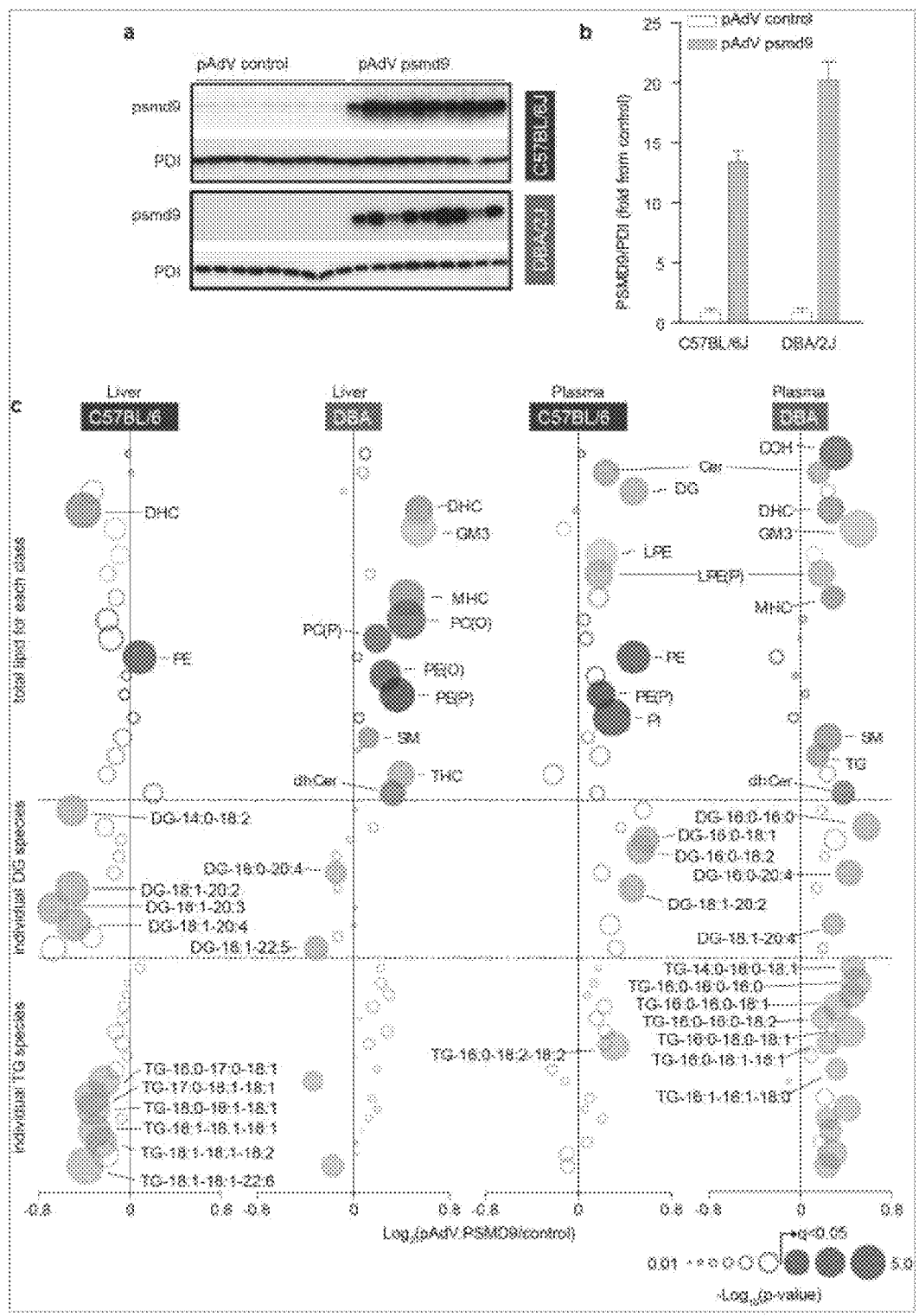
FIG. 6 (a-c) provide a graphical illustration of data showing the results of Adenoviral (AdV) overexpression of PSMD9 in C57BL/6J and 1035 DBA/2J mice (n=>8, 7 days after tail vein injection of $10^9$ plaque forming units. (a) Western-blot and (b) densitometry of PSMD9 and PDI (Protein Disulfide Isomerase; loading control) in the livers of mice treated with either control AdV or PSMD9 AdV, mean±SEM, (c) Liver and plasma lipidomics of AdV treated mice. Top panel shows relative fold-change of total lipid classes. Middle and bottom panel shows relative fold-changes of individual diacylglycerol (DG) and triacylglycerol (TG) lipid species, respectively. (t-test with permutation-based FDR correction).
Figure 7:
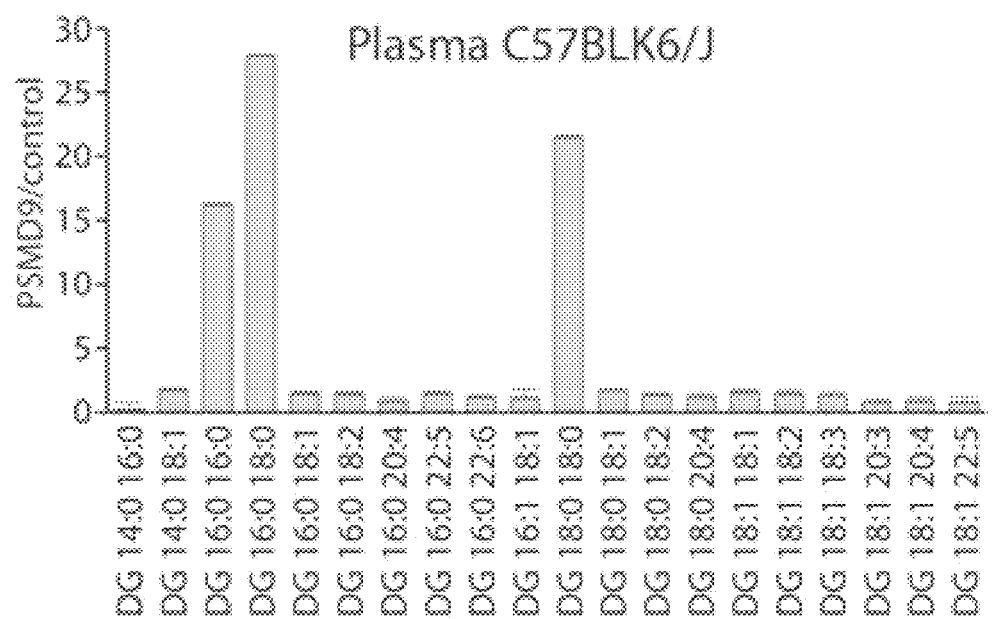
FIG. 7 (a-c) provides data showing upregulation of proteasome and lipid signalling pathways with PSMD9 overexpression.
Figure 7:
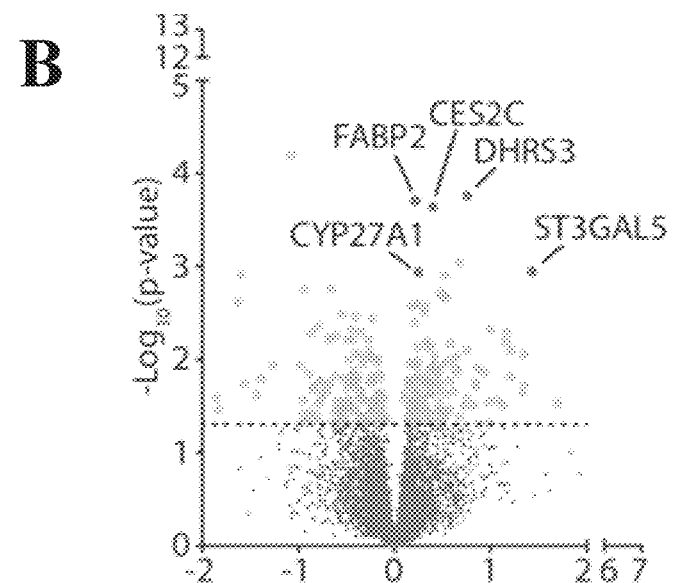
Figure 7:
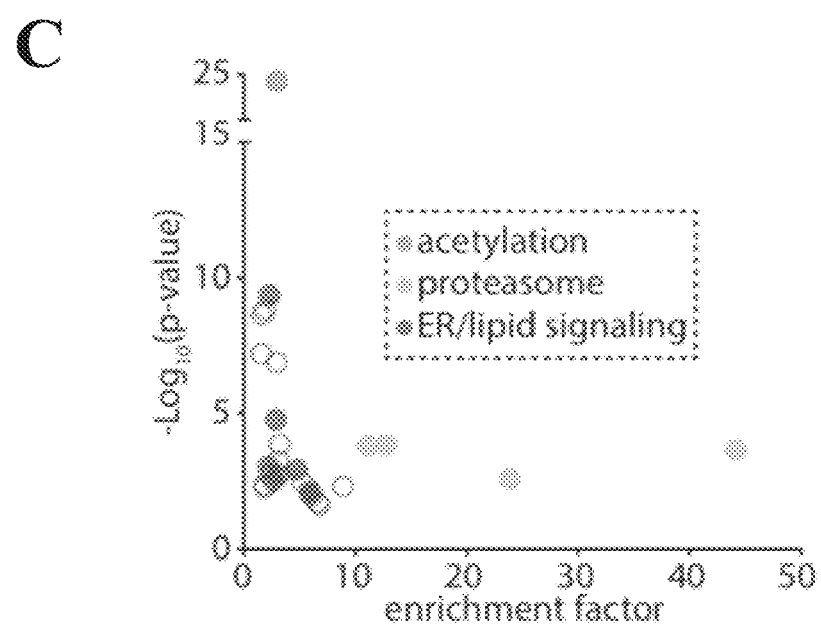

Adenoviral overexpression of Psmd9 in C57B16/J and DBA/2J mice resulted in a marked remodelling of the liver lipidome with 61 and 130 individual lipid species regulated, respectively (FIG. 4A, B) (q<0.05 permutation-based FDR). Overexpression of Psmd9 in C57B16/J mice displayed subtle decreases in several lipid classes in the liver while DBA/2J mice accumulated a variety of lipids particularly PC and PE lipids. The most striking changes were observed in the plasma where overexpression of psmd9 in C57B16/J and DBA/2J mice resulted in a significant accumulation of 56 and 96 lipids, respectively, which were primarily from the sphingolipid, acylglycerol and PC classes (Cer, DG, TG, PC, PE and LPC) (q<0.05 permutation-based FDR) (FIG. 4C) Out of the 26 lipids that significantly correlated with PSMD9 in the liver of HMDP, 19 (73%) were also regulated in the livers of either C57B16/J or DBA/2J mice following overexpression of Psmd9 (FIG. 4B), providing excellent agreement between the two models. Taken together, these data demonstrate that the trans-omic resource has identified and validated PSMD9 as a significant regulator of lipid abundance in vivo, many of which are associated with the progression of metabolic disease. Further supporting data and a breakdown of relative fold changes of individual diacylglycerol and triacylglycerol lipid species is illustrated in FIG. 6. Proteomics revealed an upregulation of proteasome and lipid signalling pathways with PSMD9 overexpression as illustrated in FIG. 7 (a-c). These data demonstrate that overexpression of mouse PSMD9 in the liver of mice for 7 days using adenovirus leads to increased levels of specific diacylglycerol species in the plasma (FIG. 7a), and alteration of abundance of many proteins in the liver as determined by proteomics (aqua dots—FIG. 7b). When we statistically analysed the pathways that these altered proteins comprised, we identified an enrichment for proteasome and ER/lipid signalling (FIG. 7c).

Example 3

Antisense Inhibition of Mouse PSMD9 in 4T1 Cells by cET Gapmers

Modified oligonucleotides were designed to target a PSMD9 nucleic acid and were tested for their effect on PSMD9 RNA levels in vitro. The modified oligonucleotides were tested in a series of experiments that had similar culture conditions. The results for each experiment are presented in separate tables shown below.

The newly designed modified oligonucleotides in the tables below were designed as 3-10-3 cEt gapmers. The gapmers are 16 nucleosides in length, wherein the central gap segment comprises of ten 2'-deoxynucleosides and is flanked by wing segments on the 5' direction and the 3' direction comprising three nucleosides each. Each nucleoside in the 5' wing segment and each nucleoside in the 3' wing segment has a cEt sugar modification. The internucleoside linkages throughout each gapmer are phosphorothioate (P=S) linkages. All cytosine residues throughout each gapmer are 5-methylcytosines. In one embodiment, oligonucleotides target intron sequences within pre-mRNA, in one embodiment, oligonucleotides target repeat regions within pre-mRNA in the nucleus as illustrated herein.

"Start site" indicates the 5'-most nucleoside to which the gapmer is targeted in the mouse gene sequence. "Stop site" indicates the 3'-most nucleoside to which the gapmer is targeted mouse gene sequence. Most of the modified oligonucleotide listed in the Tables below are targeted to either the mouse PSMD9 mRNA, designated herein as SEQ ID NO.: 10 (GENBANK Accession No. NM_026000.2) or to the mouse PSMD9 genomic sequence, designated herein as SEQ ID NO.: 11 (GENBANK Accession No. NC 000071.6 truncated from nucleotides 123225001 to 123253000).

4T1 cells at a density of 7,000 cells per well were treated using free uptake with 7,000 nM of modified oligonucleotide. After a treatment period of approximately 48 hours, RNA was isolated from the cells and PSMD9 mRNA levels were measured by quantitative real-time RTPCR. mouse primer probe set RTS37638 (forward sequence TGATCCGCAGAGGAGAGAA, designated herein as SEQ ID NO.: 12; reverse sequence GATCCCAGGAAACAGT-CATCTC; designated herein as SEQ ID NO.: 13; probe sequence AGGACTGCTGGGCTGCAACATTAT, designated herein as SEQ ID NO.: 14) was used to measure RNA levels. PSMD9 mRNA levels were normalized to total RNA content, as measured by RIBOGREEN®. Results are presented as percent inhibition of PSMD9 relative to untreated control cells. As used herein, a value of '0' indicates that treatment with the modified oligonucleotide did not inhibit PSMD9 mRNA levels. Compound numbers marked with an asterisk (*) indicate that the modified oligonucleotide is complementary to the amplicon region of the primer probe set. Additional assays may be used to measure the potency and efficacy of the modified oligonucleotides complementary to the amplicon region. Compound numbers marked with a hashtag (#) indicate that the modified oligonucleotide targets multiple sites on the nucleic acid. All start sites for the gapmer will be specified in the corresponding sub-table.

TABLE 1

Inhibition of PSMD9 RNA by 3-10-3 MOE gapmers targeting SEQ ID NO.: 1, and 2

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 997988 | 3 | 18 | 3192 | 3207 | GCAAGTACGGAAACAG | 0 | |
| 997992 | 45 | 60 | 3234 | 3249 | GGCTACGGGTCCTCCC | 4 | |
| 998000 | 143 | 158 | 3332 | 3347 | TCGGAGGACTCTGCCC | 8 | |

TABLE 1-continued

Inhibition of PSMD9 RNA by 3-10-3 MOE gapmers targeting SEQ ID NO.: 1, and 2

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 998004 | 165 | 180 | 3354 | 3369 | GCTGACCGCGGCCGCA | 0 | |
| 998008 | 226 | 241 | 3415 | 3430 | CGTAATTAGCCTTGAT | 3 | |
| 998012 | 342 | 357 | 9680 | 9695 | GATGATGTTGTGCCTT | 0 | |
| 998016 | 473 | 488 | 14656 | 14671 | AGCCTGCGGTTCATGG | 0 | |
| 998020 | 529 | 544 | 14712 | 14727 | GGCTGATACTGTTCAC | 60 | |
| 998028 | 608 | 623 | 16872 | 16887 | AAGTTTTGGGTGTTCA | 40 | |
| 998032* | 714 | 729 | 21238 | 21253 | TGGAATCAGTCTGAGC | 82 | |
| 998040 | 864 | 879 | 23398 | 23413 | CACTTAAGGGAGCCTA | 0 | |
| 998044 | 898 | 913 | 23432 | 23447 | GCCCAGGCTTCGACCA | 0 | |
| 998048 | 939 | 954 | 23473 | 23488 | GAGATTACATCAGGCA | 70 | |
| 998052 | 976 | 991 | 23510 | 23525 | GGCACAAATCACACTT | 44 | |
| 998056 | 1000 | 1015 | 23534 | 23549 | CCTAATTTGCACAAGA | 53 | |
| 998060 | 1028 | 1043 | 23562 | 23577 | ATCTAGAGAATTCCCA | 8 | |
| 998064 | 1067 | 1082 | 23601 | 23616 | TCATTACTCGCCAGAG | 0 | |
| 998068 | 1074 | 1089 | 23608 | 23623 | CATCAAATCATTACTC | 0 | |
| 998072 | 1190 | 1205 | 23724 | 23739 | ATACTAATGAGGCAGA | 16 | |
| 998076 | 1210 | 1225 | 23744 | 23759 | AGTATATGCCTCTCAT | 29 | |
| 998088 | 1406 | 1421 | 23940 | 23955 | TAGTAGGTTATTTATT | 15 | |
| 998092 | 1432 | 1447 | 23966 | 23981 | AATATACTGACAGCAC | 13 | |
| 998096 | 1451 | 1466 | 23985 | 24000 | TGGAAGATCCCACACC | 13 | |
| 998100 | 1514 | 1529 | 24048 | 24063 | GGGTACTCAAGTCCTG | 0 | |
| 998104 | 1643 | 1658 | 24177 | 24192 | CCCCTAGGCGGTGGGT | 0 | |
| 998108 | 1717 | 1732 | 24251 | 24266 | GGTAAGGCCAGTGCGG | 28 | |
| 998112 | 1763 | 1778 | 24297 | 24312 | TGGCATACACTATAAT | 22 | |
| 998116 | 1816 | 1831 | 24350 | 24365 | AGCTACAAGACTGGCT | 0 | |
| 998120 | 1937 | 1952 | 24471 | 24486 | ATCAACCGGACTGCGG | 12 | |
| 998124 | 2001 | 2016 | 24535 | 24550 | GCTCAGCCCACGGAGG | 0 | |
| 998128 | 2289 | 2304 | 24823 | 24838 | GGGTAACCTGCAAGGC | 37 | |
| 998132 | 2301 | 2316 | 24835 | 24850 | CAATATCATACTGGGT | 45 | |
| 998140 | N/A | N/A | 3574 | 3589 | AAGTTAATGCTTCCGA | 67 | |
| 998144 | N/A | N/A | 4367 | 4382 | CGTCATCTGGCACCCA | 13 | |
| 998148 | N/A | N/A | 4995 | 5010 | GCCGATGGTAGTGCAC | 30 | |
| 998152 | N/A | N/A | 5900 | 5915 | TGCATACTGAGAGCCT | 7 | |
| 998156 | N/A | N/A | 6554 | 6569 | AGTTACACCATCTTAC | 9 | |
| 998160 | N/A | N/A | 7182 | 7197 | GGCAAGTTTGATCAGG | 55 | |
| 998164 | N/A | N/A | 7734 | 7749 | GTATTTTAGCCAGAC | 73 | |

TABLE 1-continued

Inhibition of PSMD9 RNA by 3-10-3 MOE gapmers targeting SEQ ID NO.: 1, and 2

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 998168 | N/A | N/A | 8195 | 8210 | TGTTTGATGTCTGTCG | 64 | |
| 998172 | N/A | N/A | 8851 | 8866 | TCCAGATTAGCCTTGG | 0 | |
| 998176 | N/A | N/A | 9412 | 9427 | GTCCTTATAGCTACCC | 27 | |
| 998180 | N/A | N/A | 9848 | 9863 | CGACATGCAACTCTGC | 24 | |
| 998184 | N/A | N/A | 10474 | 10489 | GCTATTTGCACAGTGG | 62 | |
| 998188 | N/A | N/A | 11158 | 11173 | TTATCTACAGTGCCAA | 56 | |
| 998192 | N/A | N/A | 11970 | 11985 | AGCGACTAAGGACTCA | 55 | |
| 998196 | N/A | N/A | 12566 | 12581 | TGAATCACCGTGGTCG | 1 | |
| 998204 | N/A | N/A | 14238 | 14253 | GGCTCCTACCATCACG | 24 | |
| 998208 | N/A | N/A | 15090 | 15105 | CACAGTAATGCCGCTC | 57 | |
| 998212 | N/A | N/A | 15472 | 15487 | TGAATATTCACTGCCG | 62 | |
| 998216 | N/A | N/A | 16296 | 16311 | GCGAATCCAGCTCTGA | 78 | |
| 998220 | N/A | N/A | 17056 | 17071 | GCAAACTGTGTCATCC | 61 | |
| 998224 | N/A | N/A | 17702 | 17717 | GGCTCAAGATCATCCT | 7 | |
| 998228 | N/A | N/A | 18490 | 18505 | TGGATGTACAGCCTCG | 43 | |
| 998232 | N/A | N/A | 19086 | 19101 | CACATTGGGACTCCCC | 18 | |
| 998236 | N/A | N/A | 19981 | 19996 | AGGAATTGTATGGCCT | 21 | |
| 998240 | N/A | N/A | 20852 | 20867 | GGGTGGTACAGCAGCT | 0 | |
| 998244 | N/A | N/A | 21337 | 21352 | CAGCTCTATCTGAGCG | 9 | |
| 998248 | N/A | N/A | 21352# | 21367# | GGGTACCAGCATCCCC | 5 | |
| 998252 | N/A | N/A | 21356# | 21371# | CTATGGGTACCAGCAT | 82 | |
| 998256 | N/A | N/A | 21364# | 21379# | CACACTCTCTATGGGT | 90 | |
| 998260 | N/A | N/A | 21368# | 21383# | TGAGCACACTCTCTAT | 28 | |
| 998264 | N/A | N/A | 21376# | 21391# | GCTCTATCTGAGCACA | 26 | |
| 998268 | N/A | N/A | 21434# | 21449# | GGGTACCAGCATCCTC | 20 | |
| 998272 | N/A | N/A | 21477# | 21492# | ATGGGTGCCAGCATCC | 7 | |
| 998276 | N/A | N/A | 21481# | 21496# | CTCTATGGGTGCCAGC | 96 | |
| 998280 | N/A | N/A | 21485# | 21500# | CACTCTCTATGGGTGC | 8 | |
| 998284 | N/A | N/A | 21517 22050 | 21532 22065 | TGGGTGCCAGCATCCT | 20 | |
| 998288 | N/A | N/A | 21801 22334 22498 22621 | 21816 22349 22513 22636 | GTACCAGCATTCCCAG | 63 | |
| 998292 | N/A | N/A | 21805 22338 22502 22625 | 21820 22353 22517 22640 | ATGGGTACCAGCATTC | 54 | |
| 998296 | N/A | N/A | 22745 | 22760 | GTTATTAACCACCAGT | 16 | |

TABLE 1b

SEQ ID NO: 11 start sites for modified oligonucleotides complementary to repeat regions

| Compound Number | SEQ ID NO: | # of comp. sites within SEQ ID NO: 11 | SEQ ID NO: 2 start sites |
|---|---|---|---|
| 998248 | | 10 | 21352, 21393, 21557, 21721, 21885, 21926, 22090, 22254, 22418, 22541, 22664 |
| 998252 | | 21 | 21356, 21397, 21438, 21561, 21684, 21725, 21807, 21848, 21889, 21930, 21971, 22094, 22217, 22258, 22340, 22381, 22422, 22504, 22545, 22627, 22668 |
| 998256 | | 33 | 21364, 21405, 21446, 21487, 21528, 21569, 21610, 21651, 21692, 21733, 21774, 21815, 21856, 21897, 21938, 21979, 22020, 22061, 22102, 22143, 22184, 22225, 22266, 22307, 22348, 22389, 22430, 22471, 22512, 22553, 22594, 22635, 22676 |
| 998260 | | 33 | 21368, 21409, 21450, 21491, 21532, 21573, 21614, 21655, 21696, 21737, 21778, 21819, 21860, 21901, 21942, 21983, 22024, 22065, 22106, 22147, 22188, 22229, 22270, 22311, 22352, 22393, 22434, 22475, 22516, 22557, 22598, 22639, 22680 |
| 998264 | | 32 | 21376, 21417, 21458, 21499, 21540, 21581, 21622, 21663, 21704, 21745, 21786, 21827, 21868, 21909, 21950, 21991, 22073, 22032, 22114, 22155, 22196, 22237, 22278, 22319, 22360, 22401, 22442, 22483, 22524, 22565, 22606, 22647 |
| 998268 | | 6 | 21434, 21680, 21844, 21967, 22213, 22377 |
| 998272 | | 12 | 21477, 21518, 21600, 21641, 21764, 22010, 22051, 22133, 22174, 22297, 22461, 22584 |
| 998276 | | 12 | 21481, 21522, 21604, 21645, 21768, 22014, 22055, 22137, 22178, 22301, 22465, 22588 |
| 998280 | | 12 | 21485, 21526, 21608, 21649, 21772, 22018, 22059, 22141, 22182, 22305, 22469, 22592 |

TABLE 2

Inhibition of PSMD9 RNA by 3-10-3 MOE gapmers targeting SEQ ID NO.: 10, and 11

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 997989 | 7 | 22 | 3196 | 3211 | ACGCGCAAGTACGGAA | 12 | |
| 997993 | 48 | 63 | 3237 | 3252 | TGAGGCTACGGGTCCT | 0 | |
| 997997 | 96 | 111 | 3285 | 3300 | CCTCAAGCTAGAGTTC | 25 | |
| 998001 | 147 | 162 | 3336 | 3351 | GGCCTCGGAGGACTCT | 7 | |
| 998005 | 174 | 189 | 3363 | 3378 | CTGGATGTCGCTGACC | 23 | |
| 998013 | 421 | 436 | 14604 | 14619 | TCTCTTTGTCCCGAGC | 10 | |
| 998017 | 477 | 492 | 14660 | 14675 | GGCCAGCCTGCGGTTC | 63 | |
| 998021 | 552 | 567 | 14735 | 14750 | CGCAATACTGGCTGGG | 34 | |
| 998025 | 594 | 609 | 16858 | 16873 | CACGGAGCCGAACTCC | 2 | |
| 998029 | 649 | 664 | 16913 | 16928 | CGCTATGCTGCACCAC | 19 | |
| 998033* | 715 | 730 | 21239 | 21254 | TTGGAATCAGTCTGAG | 49 | |
| 998041 | 866 | 881 | 23400 | 23415 | TACACTTAAGGGAGCC | 7 | |
| 998045 | 910 | 925 | 23444 | 23459 | TTCCACCTCGATGCCC | 0 | |
| 998049 | 942 | 957 | 23476 | 23491 | AGAGAGATTACATCAG | 44 | |
| 998053 | 984 | 999 | 23518 | 23533 | CGTAGCTAGGCACAAA | 32 | |
| 998057 | 1002 | 1017 | 23536 | 23551 | GGCCTAATTTGCACAA | 0 | |
| 998061 | 1031 | 1046 | 23565 | 23580 | ATAATCTAGAGAATTC | 11 | |

TABLE 2-continued

Inhibition of PSMD9 RNA by 3-10-3 MOE gapmers targeting SEQ ID NO.: 10, and 11

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 998065 | 1070 | 1085 | 23604 | 23619 | AAATCATTACTCGCCA | 38 | |
| 998069 | 1102 | 1117 | 23636 | 23651 | ACTGAGTCCGTCTCCA | 64 | |
| 998077 | 1211 | 1226 | 23745 | 23760 | CAGTATATGCCTCTCA | 0 | |
| 998085 | 1327 | 1342 | 23861 | 23876 | GGGACTTGAGATGACA | 0 | |
| 998089 | 1410 | 1425 | 23944 | 23959 | CACTTAGTAGGTTATT | 20 | |
| 998093 | 1434 | 1449 | 23968 | 23983 | TGAATATACTGACAGC | 46 | |
| 998097 | 1452 | 1467 | 23986 | 24001 | GTGGAAGATCCCACAC | 0 | |
| 998101 | 1628 | 1643 | 24162 | 24177 | TGATACTGCAGTTGGA | 18 | |
| 998105 | 1679 | 1694 | 24213 | 24228 | CTGAACTTGTGAGATC | 36 | |
| 998109 | 1724 | 1739 | 24258 | 24273 | TCCCAAGGGTAAGGCC | 0 | |
| 998113 | 1778 | 1793 | 24312 | 24327 | TGTAACAAGGTTTGGT | 4 | |
| 998117 | 1903 | 1918 | 24437 | 24452 | TCGCAGGACTTCCTTC | 0 | |
| 998121 | 1944 | 1959 | 24478 | 24493 | CCCAAGAATCAACCGG | 0 | |
| 998125 | 2045 | 2060 | 24579 | 24594 | CATCAGGCTCTCAAAG | 16 | |
| 998129 | 2295 | 2310 | 24829 | 24844 | CATACTGGGTAACCTG | 44 | |
| 998133 | 2302 | 2317 | 24836 | 24851 | CCAATATCATACTGGG | 0 | |
| 998137 | 2359 | 2374 | 24893 | 24908 | TTTTACTGTAGAAGTA | 0 | |
| 998141 | N/A | N/A | 3674 | 3689 | GCGATTCCCGCACTCA | 0 | |
| 998145 | N/A | N/A | 4552 | 4567 | TATGATGGCCAGTGCC | 0 | |
| 998149 | N/A | N/A | 5291 | 5306 | GGTCTCTGCGGTATGC | 71 | |
| 998153 | N/A | N/A | 6088 | 6103 | CTATATCCCAGACACC | 6 | |
| 998157 | N/A | N/A | 6661 | 6676 | GATATATTTGCAACAA | 74 | |
| 998161 | N/A | N/A | 7423 | 7438 | CACTTATCTGTTAGCT | 53 | |
| 998165 | N/A | N/A | 7913 | 7928 | TAATATGGGAGCCTTC | 0 | |
| 998169 | N/A | N/A | 8360 | 8375 | TGCTTTAGGGCCAGCT | 22 | |
| 998173 | N/A | N/A | 9005 | 9020 | ATAGGATGTAGCTCGG | 58 | |
| 998177 | N/A | N/A | 9447 9466 | 9462 9481 | TGATGTCTTTAGCACA | 75 | |
| 998181 | N/A | N/A | 9861 | 9876 | ATAATAAAGCCATCGA | 43 | |
| 998185 | N/A | N/A | 10624 | 10639 | ACCAATGGCACACTCA | 37 | |
| 998189 | N/A | N/A | 11161 | 11176 | TGATTATCTACAGTGC | 57 | |
| 998193 | N/A | N/A | 12181 | 12196 | GGCTTACAGTAGAGTC | 5 | |
| 998197 | N/A | N/A | 12776 | 12791 | ATAATATTGAATCAGG | 41 | |
| 998201 | N/A | N/A | 13668 | 13683 | TGCAACTATGCCCTGA | 0 | |
| 998205 | N/A | N/A | 14493 | 14508 | GCTAGCGCGGGACACA | 37 | |
| 998209 | N/A | N/A | 15233 | 15248 | AAAATTACTGGTGCTC | 32 | |

TABLE 2-continued

Inhibition of PSMD9 RNA by 3-10-3 MOE gapmers targeting SEQ ID NO.: 10, and 11

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 998213 | N/A | N/A | 15553 | 15568 | GTCACACACGGAGAGC | 23 | |
| 998217 | N/A | N/A | 16642 | 16657 | GGAGTAGGCAGGTGCC | 48 | |
| 998221 | N/A | N/A | 17226 | 17241 | GACAGATACCCAGCGC | 48 | |
| 998225 | N/A | N/A | 17802 | 17817 | ACCTATATCCACGGGC | 22 | |
| 998229 | N/A | N/A | 18598 | 18613 | TGAGATGCGACCCCCT | 21 | |
| 998233 | N/A | N/A | 19372 | 19387 | CAAGATTGCTTGCGCT | 37 | |
| 998237 | N/A | N/A | 20192 | 20207 | TTCTTACTGAGACACA | 59 | |
| 998241 | N/A | N/A | 20988 | 21003 | TCCTTAAGTTCCGGCA | 66 | |
| 998249 | N/A | N/A | 21353# | 21368# | TGGGTACCAGCATCCC | 0 | |
| 998253 | N/A | N/A | 21361# | 21376# | ACTCTCTATGGGTACC | 86 | |
| 998261 | N/A | N/A | 21373# | 21388# | CTATCTGAGCACACTC | 67 | |
| 998265 | N/A | N/A | 21377# | 21392# | AGCTCTATCTGAGCAC | 5 | |
| 998269 | N/A | N/A | 21435# | 21450# | TGGGTACCAGCATCCT | 19 | |
| 998273 | N/A | N/A | 21478# | 21493# | TATGGGTGCCAGCATC | 47 | |
| 998277 | N/A | N/A | 21482# | 21497# | TCTCTATGGGTGCCAG | 78 | |
| 998281 | N/A | N/A | 21486# | 21501# | ACACTCTATGGGTG | 0 | |
| 998285 | N/A | N/A | 21791, 22324, 22488, 22611 | 21806, 22339, 22503, 22626 | TCCCAGCTCTATCTGA | 30 | |
| 998289 | N/A | N/A | 21802, 22335, 22499, 22622 | 21817, 22350, 22514, 22637 | GGTACCAGCATTCCCA | 40 | |
| 998293 | N/A | N/A | 21806, 22339, 22503, 22626 | 21821, 22354, 22518, 22641 | TATGGGTACCAGCATT | 51 | |
| 998297 | N/A | N/A | 22812 | 22827 | AGGGATTGAGAAGTGA | 26 | |

TABLE 2b

SEQ ID NO: 11 start sites for modified oligonucleotides complementary to repeat regions

| Compound Number | SEQ ID NO: | # of comp. sites within SEQ ID NO: 11 | SEQ ID NO: 11 start sites |
|---|---|---|---|
| 998249 | 11 | 11 | 21353, 21394, 21558, 21722, 21886, 21927, 22091, 22255, 22419, 22542, 22665 |
| 998253 | | 21 | 21361, 21402, 21443, 21566, 21689, 21730, 21812, 21853, 21894, 21935, 21976, 22099, 22222, 22263, 22345, 22386, 22427, 22509, 22550, 22632, 22673 |
| 998261 | | 33 | 21373, 21414, 21455, 21496, 21537, 21578, 21619, 21660, 21701, 21742, 21783, 21824, 21865, 21906, 21947, 21988, 22029, 22070, 22111, 22152, 22193, 22234, 22275, 22316, 22357, 22398, 22439, 22480, 22521, 22562, 22603, 22644, 22685 |

TABLE 2b-continued

SEQ ID NO: 11 start sites for modified oligonucleotides complementary to repeat regions

| Compound Number | SEQ ID NO: | # of comp. sites within SEQ ID NO: 11 | SEQ ID NO: 11 start sites |
|---|---|---|---|
| 998265 | | 32 | 21377, 21418, 21459, 21500, 21541, 21582, 21623, 21664, 21705, 21746, 21787, 21828, 21869, 21910, 21951, 21992, 22033, 22074, 22115, 22156, 22197, 22238, 22279, 22320, 22361, 22402, 22443, 22484, 22525, 22566, 22607, 22648 |
| 998269 | | 6 | 21435, 21681, 21845, 21968, 22214, 22378 |
| 998273 | | 12 | 21478, 21519, 21601, 21642, 21765, 22011, 22052, 22134, 22175, 22298, 22462, 22585 |
| 998277 | | 12 | 21482, 21523, 21605, 21646, 21769, 22015, 22138, 22056, 22179, 22302, 22466, 22589 |
| 998281 | | 12 | 21486, 21527, 21609, 21650, 21773, 22019, 22060, 22142, 22183, 22306, 22470, 22593 |

TABLE 3

Inhibition of PSMD9 RNA by 3-10-3 MOE gapmers targeting SEQ ID NO.: 10, and 11

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 997990 | 12 | 27 | 3201 | 3216 | AGCCAACGCGCAAGTA | 16 | |
| 997994 | 51 | 66 | 3240 | 3255 | GGCTGAGGCTACGGGT | 0 | |
| 997998 | 110 | 125 | 3299 | 3314 | CCCGACATCGCGGACC | 4 | |
| 998002 | 153 | 168 | 3342 | 3357 | CGCACGGGCCTCGGAG | 14 | |
| 998006 | 186 | 201 | 3375 | 3390 | TCGCATCAGATCCTGG | 0 | |
| 998010 | 313 | 328 | 9651 | 9666 | GGTACAAGTCCACATC | 23 | |
| 998014 | 433 | 448 | 14616 | 14631 | CCCGAGCCTGCTTCTC | 0 | |
| 998018 | 526 | 541 | 14709 | 14724 | TGATACTGTTCACTCT | 0 | |
| 998022 | 553 | 568 | 14736 | 14751 | CCGCAATACTGGCTGG | 15 | |
| 998026 | 597 | 612 | 16861 | 16876 | GTTCACGGAGCCGAAC | 11 | |
| 998030* | 675 | 690 | 21199 | 21214 | CACCGTCACATTCAGG | 0 | |
| 998034* | 725 | 740 | 21249 | 21264 | GCCCAGCGGGTTGGAA | 85 | |
| 998038 | 849 | 864 | 23383 | 23398 | AGAGAACGAGGAAACG | 0 | |
| 998042 | 869 | 884 | 23403 | 23418 | CCTTACACTTAAGGGA | 0 | |
| 998046 | 936 | 951 | 23470 | 23485 | ATTACATCAGGCAGCC | 21 | |
| 998050 | 960 | 975 | 23494 | 23509 | TTAATAATGCCTCAAC | 24 | |
| 998054 | 998 | 1013 | 23532 | 23547 | TAATTTGCACAAGACG | 28 | |
| 998058 | 1008 | 1023 | 23542 | 23557 | GGCTATGGCCTAATTT | 0 | |
| 998066 | 1072 | 1087 | 23606 | 23621 | TCAAATCATTACTCGC | 55 | |
| 998070 | 1105 | 1120 | 23639 | 23654 | CACACTGAGTCCGTCT | 49 | |
| 998074 | 1193 | 1208 | 23727 | 23742 | CCAATACTAATGAGGC | 0 | |
| 998078 | 1212 | 1227 | 23746 | 23761 | TCAGTATATGCCTCTC | 31 | |
| 998082 | 1288 | 1303 | 23822 | 23837 | GCATGTACGAAATTCT | 71 | |

TABLE 3-continued

Inhibition of PSMD9 RNA by 3-10-3 MOE gapmers targeting SEQ ID NO.: 10, and 11

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 998086 | 1328 | 1343 | 23862 | 23877 | AGGGACTTGAGATGAC | 27 | |
| 998090 | 1412 | 1427 | 23946 | 23961 | GGCACTTAGTAGGTTA | 33 | |
| 998094 | 1435 | 1450 | 23969 | 23984 | ATGAATATACTGACAG | 0 | |
| 998098 | 1457 | 1472 | 23991 | 24006 | CTCCAGTGGAAGATCC | 0 | |
| 998102 | 1630 | 1645 | 24164 | 24179 | GGTGATACTGCAGTTG | 33 | |
| 998106 | 1706 | 1721 | 24240 | 24255 | TGCGGGTACACTGAGC | 0 | |
| 998110 | 1729 | 1744 | 24263 | 24278 | CAAGATCCCAAGGGTA | 16 | |
| 998114 | 1779 | 1794 | 24313 | 24328 | CTGTAACAAGGTTTGG | 43 | |
| 998118 | 1907 | 1922 | 24441 | 24456 | TGCTTCGCAGGACTTC | 16 | |
| 998122 | 1992 | 2007 | 24526 | 24541 | ACGGAGGGACACTTGC | 9 | |
| 998126 | 2055 | 2070 | 24589 | 24604 | TCAGAGGATGCATCAG | 52 | |
| 998130 | 2297 | 2312 | 24831 | 24846 | ATCATACTGGGTAACC | 28 | |
| 998134 | 2309 | 2324 | 24843 | 24858 | GAGGAAGCCAATATCA | 22 | |
| 998138 | 2381 | 2396 | 24915 | 24930 | AATCAGGCCCATCTGC | 46 | |
| 998142 | N/A | N/A | 3957 | 3972 | GCAAGAATAACCCTCA | 0 | |
| 998146 | N/A | N/A | 4847 | 4862 | AGCTTTACCAAGCCGG | 0 | |
| 998150 | N/A | N/A | 5539 | 5554 | GGTTTCTAATAGGTTT | 91 | |
| 998154 | N/A | N/A | 6291 | 6306 | GTTACCACGCATGTGT | 11 | |
| 998158 | N/A | N/A | 6910 | 6925 | AGCATTTCCGGGCTGG | 22 | |
| 998162 | N/A | N/A | 7445 | 7460 | ACTGTATGGGTTGACT | 12 | |
| 998170 | N/A | N/A | 8469 | 8484 | CTTTATACTTAGCCTC | 51 | |
| 998174 | N/A | N/A | 9237 | 9252 | CCATATGCACTCCTCA | 33 | |
| 998178 | N/A | N/A | 9448 9467 | 9463 9482 | GTGATGTCTTTAGCAC | 25 | |
| 998182 | N/A | N/A | 10162 | 10177 | TACTTTTGTATGCAGC | 64 | |
| 998186 | N/A | N/A | 10732 | 10747 | TCTAACAGGTACTTCA | 17 | |
| 998190 | N/A | N/A | 11300 | 11315 | TCTTACTCTGCACCCT | 25 | |
| 998194 | N/A | N/A | 12299 | 12314 | GGTCATCTAGCCTGCC | 27 | |
| 998198 | N/A | N/A | 12916 | 12931 | CCTACTACTGGGCTCT | 35 | |
| 998202 | N/A | N/A | 13780 | 13795 | AATATAATCACATCGG | 59 | |
| 998206 | N/A | N/A | 14761 | 14776 | GGATTTGGGAGAGCCA | 20 | |
| 998210 | N/A | N/A | 15345 | 15360 | CTTCATCTGTGACCCG | 84 | |
| 998214 | N/A | N/A | 15773 | 15788 | TCCGAATTCAGAATCC | 29 | |
| 998218 | N/A | N/A | 16763 | 16778 | GGTCATTTGTACCGCT | 35 | |
| 998222 | N/A | N/A | 17365 | 17380 | GTGTAAAAGACTCAGC | 45 | |
| 998226 | N/A | N/A | 17907 | 17922 | CTACTATCCATTTGGG | 10 | |
| 998230 | N/A | N/A | 18809 | 18824 | TGAGGGACCGCTAACA | 0 | |

TABLE 3-continued

Inhibition of PSMD9 RNA by 3-10-3 MOE gapmers targeting SEQ ID NO.: 10, and 11

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 998234 | N/A | N/A | 19515 | 19530 | CAGAAATTGTTGTTGC | 0 | |
| 998238 | N/A | N/A | 20611 | 20626 | CTTACTCCGAGGGTCA | 60 | |
| 998242 | N/A | N/A | 21333 | 21348 | TCTATCTGAGCGCACT | 45 | |
| 998246 | N/A | N/A | 21339# | 21354# | CCCAGCTCTATCTGAG | 58 | |
| 998250 | N/A | N/A | 21354# | 21369# | ATGGGTACCAGCATCC | 70 | |
| 998254 | N/A | N/A | 21362# | 21377# | CACTCTCTATGGGTAC | 68 | |
| 998258 | N/A | N/A | 21366# | 21381# | AGCACACTCTCTATGG | 96 | |
| 998262 | N/A | N/A | 21374# | 21389# | TCTATCTGAGCACACT | 59 | |
| 998270 | N/A | N/A | 21475# | 21490# | GGGTGCCAGCATCCCC | 10 | |
| 998278 | N/A | N/A | 21483# | 21498# | CTCTCTATGGGTGCCA | 75 | |
| 998286 | N/A | N/A | 21792 22325 22489 22612 | 21807 22340 22504 22627 | TTCCCAGCTCTATCTG | 49 | |
| 998290 | N/A | N/A | 21803 22336 22500 22623 | 21818 22351 22515 22638 | GGGTACCAGCATTCCC | 0 | |
| 998294 | N/A | N/A | 22687 | 22702 | TTCTATCTGAGCACAC | 69 | |
| 998298 | N/A | N/A | 22973 | 22988 | TGTATATAAGAGAGTC | 56 | |

TABLE 3b

SEQ ID NO: 11 start sites for modified oligonucleotides complementary to repeat regions

| Compound Number | SEQ ID NO: | # of comp. sites within SEQ ID NO: 11 | SEQ ID NO: 2 start sites |
|---|---|---|---|
| 998246 | | 25 | 21339, 21380, 21462, 21544, 21585, 21626, 21708, 21749, 21790, 21872, 21913, 21995, 22077, 22118, 22159, 22241, 22282, 22323, 22405, 22446, 22487, 22528, 22569, 22610, 22651 |
| 998250 | | 17 | 21354, 21395, 21436, 21559, 21682, 21723, 21846, 21887, 21928, 21969, 22092, 22215, 22256, 22379, 22420, 22543, 22666 |
| 998254 | | 21 | 21362, 21403, 21444, 21567, 21690, 21731, 21813, 21854, 21895, 21936, 21977, 22100, 22223, 22264, 22346, 22387, 22428, 22510, 22551, 22633, 22674 |
| 998258 | | 33 | 21366, 21407, 21448, 21489, 21530, 21571, 21612, 21653, 21694, 21735, 21776, 21817, 21899, 21858, 21940, 21981, 22022, 22063, 22104, 22145, 22186, 22227, 22268, 22309, 22350, 22391, 22432, 22473, 22514, 22555, 22596, 22637, 22678 |
| 998262 | | 33 | 21374, 21415, 21456, 21497, 21538, 21579, 21620, 21661, 21702, 21743, 21825, 21784, 21866, 21907, 21948, 21989, 22030, 22071, 22112, 22153, 22194, 22235, 22276, 22317, 22358, 22399, 22440, 22481, 22522, 22563, 22604, 22645, 22686, |
| 998270 | | 10 | 21475, 21598, 21639, 21762, 22008, 22131, 22172, 22295, 22459, 22582 |
| 998278 | | 12 | 21483, 21524, 21606, 21647, 21770, 22016, 22057, 22139, 22180, 22303, 22467, 22590 |

TABLE 4

Inhibition of PSMD9 RNA by 3-10-3 MOE gapmers targeting SEQ ID NO.: 10, and 11

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 997991 | 16 | 31 | 3205 | 3220 | GCTCAGCCAACGCGCA | 10 | |
| 997995 | 79 | 94 | 3268 | 3283 | GGGTTTCCCGGCTACG | 14 | |
| 997999 | 115 | 130 | 3304 | 3319 | CTTCACCCGACATCGC | 22 | |
| 998003 | 156 | 171 | 3345 | 3360 | GGCCGCACGGGCCTCG | 0 | |
| 998007 | 223 | 238 | 3412 | 3427 | AATTAGCCTTGATCTC | 29 | |
| 998011 | 321 | 336 | 9659 | 9674 | TCGGACCTGGTACAAG | 24 | |
| 998015 | 445 | 460 | 14628 | 14643 | CTTCAGCCATGTCCCG | 0 | |
| 998019 | 527 | 542 | 14710 | 14725 | CTGATACTGTTCACTC | 35 | |
| 998023 | 571 | 586 | 16835 | 16850 | CGTCATCCACTTGCAG | 47 | |
| 998027 | 600 | 615 | 16864 | 16879 | GGTGTTCACGGAGCCG | 4 | |
| 998031* | 683 | 698 | 21207 | 21222 | CTGCGGATCACCGTCA | 59 | |
| 998039 | 853 | 868 | 23387 | 23402 | GCCTAGAGAACGAGGA | 20 | |
| 998043 | 870 | 885 | 23404 | 23419 | TCCTTACACTTAAGGG | 0 | |
| 998047 | 937 | 952 | 23471 | 23486 | GATTACATCAGGCAGC | 53 | |
| 998055 | 999 | 1014 | 23533 | 23548 | CTAATTTGCACAAGAC | 9 | |
| 998059 | 1013 | 1028 | 23547 | 23562 | AGACAGGCTATGGCCT | 12 | |
| 998063 | 1059 | 1074 | 23593 | 23608 | CGCCAGAGTCATCCCC | 0 | |
| 998067 | 1073 | 1088 | 23607 | 23622 | ATCAAATCATTACTCG | 48 | |
| 998071 | 1108 | 1123 | 23642 | 23657 | TTACACACTGAGTCCG | 64 | |
| 998075 | 1209 | 1224 | 23743 | 23758 | GTATATGCCTCTCATC | 0 | |
| 998079 | 1244 | 1259 | 23778 | 23793 | AATACATATTCCTCAG | 48 | |
| 998083 | 1289 | 1304 | 23823 | 23838 | TGCATGTACGAAATTC | 61 | |
| 998087 | 1355 | 1370 | 23889 | 23904 | GGAAGTGGGTACGAGG | 56 | |
| 998091 | 1418 | 1433 | 23952 | 23967 | ACAAATGGCACTTAGT | 21 | |
| 998095 | 1439 | 1454 | 23973 | 23988 | CACCATGAATATACTG | 28 | |
| 998099 | 1476 | 1491 | 24010 | 24025 | TGGAAGGTTGACCACA | 18 | |
| 998103 | 1631 | 1646 | 24165 | 24180 | GGGTGATACTGCAGTT | 0 | |
| 998107 | 1712 | 1727 | 24246 | 24261 | GGCCAGTGCGGGTACA | 0 | |
| 998111 | 1755 | 1770 | 24289 | 24304 | ACTATAATACCAGGAG | 30 | |
| 998115 | 1784 | 1799 | 24318 | 24333 | CTAACCTGTAACAAGG | 18 | |
| 998119 | 1932 | 1947 | 24466 | 24481 | CCGGACTGCGGCCCAG | 25 | |
| 998123 | 1996 | 2011 | 24530 | 24545 | GCCCACGGAGGGACAC | 0 | |
| 998127 | 2082 | 2097 | 24616 | 24631 | GGCTACGGTGACTCCA | 12 | |
| 998131 | 2298 | 2313 | 24832 | 24847 | TATCATACTGGGTAAC | 15 | |
| 998135 | 2327 | 2342 | 24861 | 24876 | TTCCAGTGGGTTACTG | 0 | |
| 998143 | N/A | N/A | 4156 | 4171 | GCTTAATCTGGCTCCA | 7 | |

TABLE 4-continued

Inhibition of PSMD9 RNA by 3-10-3 MOE gapmers targeting SEQ ID NO.: 10, and 11

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 998147 | N/A | N/A | 4853 | 4868 | GTTTTAAGCTTTACCA | 49 | |
| 998155 | N/A | N/A | 6406 | 6421 | GGCCTTTAAGAGTTCC | 0 | |
| 998159 | N/A | N/A | 7032 | 7047 | CACAATTCCACGCTAC | 8 | |
| 998163 | N/A | N/A | 7610 | 7625 | AGTACTGGGAGATAGC | 0 | |
| 998171 | N/A | N/A | 8639 | 8654 | ACCAAGATTCCTCCCA | 20 | |
| 998175 | N/A | N/A | 9238 | 9253 | TCCATATGCACTCCTC | 32 | |
| 998179 | N/A | N/A | 9449 9468 | 9464 9483 | AGTGATGTCTTTAGCA | 81 | |
| 998183 | N/A | N/A | 10473 | 10488 | CTATTTGCACAGTGGG | 50 | |
| 998187 | N/A | N/A | 10902 | 10917 | CAAAGGATACACCACC | 18 | |
| 998191 | N/A | N/A | 11706 | 11721 | TGGTACAGTAAGCTCT | 36 | |
| 998195 | N/A | N/A | 12455 | 12470 | CCTTATTCAACCCAGG | 1 | |
| 998199 | N/A | N/A | 13038 | 13053 | TGTTTAGGGTTAGCCT | 9 | |
| 998203 | N/A | N/A | 13905 | 13920 | TGCTTATTAGGTGCTA | 23 | |
| 998207 | N/A | N/A | 14929 | 14944 | ACCATAGGTCTCTCCC | 53 | |
| 998211 | N/A | N/A | 15451 | 15466 | CGTATAATAGCCCCAA | 62 | |
| 998215 | N/A | N/A | 15954 | 15969 | TTGTATGTCAGTTGCC | 86 | |
| 998219 | N/A | N/A | 16927 | 16942 | CCGACTTACCCCCTCG | 38 | |
| 998223 | N/A | N/A | 17486 | 17501 | CCCAATAACAGCTGCA | 0 | |
| 998227 | N/A | N/A | 18076 | 18091 | CTCTATAGCAAGGTGT | 46 | |
| 998231 | N/A | N/A | 18916 | 18931 | CGTGGCAGCGCACTGT | 0 | |
| 998235 | N/A | N/A | 19932 | 19947 | TCAATACTCATGTTGT | 74 | |
| 998239 | N/A | N/A | 20727 | 20742 | CCAATCAACAATCTGG | 16 | |
| 998243 | N/A | N/A | 21336 | 21351 | AGCTCTATCTGAGCGC | 24 | |
| 998247 | N/A | N/A | 21351# | 21366# | GGTACCAGCATCCCCA | 55 | |
| 998251 | N/A | N/A | 21355# | 21370# | TATGGGTACCAGCATC | 64 | |
| 998255 | N/A | N/A | 21363# | 21378# | ACACTCTATGGGTA | 74 | |
| 998259 | N/A | N/A | 21367# | 21382# | GAGCACACTCTCTATG | 58 | |
| 998263 | N/A | N/A | 21375# | 21390# | CTCTATCTGAGCACAC | 85 | |
| 998267 | N/A | N/A | 21420# | 21435# | TCAGCTCTATCTGAGC | 19 | |
| 998271 | N/A | N/A | 21476# | 21491# | TGGGTGCCAGCATCCC | 0 | |
| 998275 | N/A | N/A | 21480# | 21495# | TCTATGGGTGCCAGCA | 95 | |
| 998279 | N/A | N/A | 21484# | 21499# | ACTCTCTATGGGTGCC | 79 | |
| 998283 | N/A | N/A | 21516 22049 | 21531 22064 | GGGTGCCAGCATCCTC | 12 | |
| 998287 | N/A | N/A | 21794 22327 22491 22614 | 21809 22342 22506 22629 | CATTCCCAGCTCTATC | 27 | |

TABLE 4-continued

Inhibition of PSMD9 RNA by 3-10-3 MOE gapmers targeting SEQ ID NO.: 10, and 11

| Compound Number | SEQ ID NO: 10 Start Site | SEQ ID NO: 10 Stop Site | SEQ ID NO: 11 Start Site | SEQ ID NO: 11 Stop Site | Sequence (5' to 3') | PSMD9 (% Inhibition) | SEQ ID NO |
|---|---|---|---|---|---|---|---|
| 998291 | N/A | N/A | 21804 | 21819 | TGGGTACCAGCATTCC | 72 | |
| | | | 22337 | 22352 | | | |
| | | | 22501 | 22516 | | | |
| | | | 22624 | 22639 | | | |
| 998295 | N/A | N/A | 22688 | 22703 | GTTCTATCTGAGCACA | 36 | |
| 998299 | N/A | N/A | 23218 | 23233 | GTGAACACTTCTTCTC | 46 | |

TABLE 4b

SEQ ID NO: 11 start sites for modified oligonucleotides complementary to repeat regions

| Compound Number | SEQ ID NO: | # of comp. sites within SEQ ID NO: 11 | SEQ ID NO: 2 start sites |
|---|---|---|---|
| 998247 | | 11 | 21351, 21392, 21556, 21720, 21884, 21925, 22089, 22253, 22417, 22540, 22663 |
| 998251 | | 17 | 21355, 21396, 21437, 21560, 21683, 21724, 21847, 21888, 21929, 21970, 22093, 22216, 22257, 22421, 22380, 22544, 22667 |
| 998255 | | 21 | 998255, 998255, 998255, 998255, 998255, 998255, 998255, 998255, 998255, 998255, 998255, 998255, 998255, 998255, 998255, 998255, 998255, 998255, 998255, 998255, 998255 |
| 998259 | | 33 | 21367, 21408, 21449, 21490, 21531, 21572, 21613, 21654, 21695, 21736, 21777, 21818, 21859, 21900, 21941, 21982, 22023, 22064, 22105, 22146, 22187, 22228, 22269, 22310, 22351, 22392, 22433, 22474, 22515, 22556, 22597, 22638, 22679 |
| 998263 | | 32 | 21375, 21416, 21457, 21498, 21539, 21580, 21621, 21662, 21703, 21744, 21785, 21826, 21867, 21908, 21949, 21990, 22031, 22072, 22113, 22154, 22195, 22236, 22277, 22318, 22359, 22400, 22482, 22441, 22523, 22564, 22605, 22646 |
| 998267 | | 8 | 21420, 21502, 21666, 21830, 21953, 22035, 22199, 22363 |
| 998271 | | 10 | 21476, 21599, 21640, 21763, 22009, 22132, 22173, 22296, 22460, 22583 |
| 998275 | | 12 | 21480, 21521, 21603, 21644, 21767, 22013, 22054, 22136, 22177, 22300, 22464, 22587 |
| 998279 | | 12 | 21484, 21525, 21607, 21648, 21771, 22017, 22058, 22140, 22181, 22304, 22468, 22591 |

Example 4

Dose-Dependent Inhibition of Mouse PSMD9 in 4T1 Cells by cET Gapmers

Modified oligonucleotides described in the studies above exhibiting significant in vitro inhibition of PSMD9 mRNA were selected and tested at various doses in 4T1 cells.

4T1 cells plated at a density of 7,000 cells per well were treated using free uptake with modified oligonucleotides diluted to different concentrations as specified in the tables below. After a treatment period of approximately 48 hours, PSMD9 mRNA levels were measured as previously described using the mouse PSMD9 primer-probe set RTS37638. PSMD9 mRNA levels were normalized to total RNA content, as measured by RIBOGREEN®. Results are presented in the tables below as percent inhibition of PSMD9, relative to untreated control cells. As used herein, a value of '0' indicates that treatment with the modified oligonucleotide did not inhibit PSMD9 mRNA levels.

The half maximal inhibitory concentration (IC$_{50}$) of each modified oligonucleotide is also presented. IC$_{50}$ was calculated using a linear regression on a log/linear plot of the data in excel. In some cases, precise IC50 could not be reliably calculated as the knockdown at the lowest dose tested led to inhibition greater than 50%. In such cases, IC50s are marked as NC (Not Calculated).

TABLE 5

Multi-dose assay of modified oligonucleotides in 4T1 cells

| ION No. | % Inhibition RTS37638 | | | | IC50 (μM) |
|---|---|---|---|---|---|
| | 0.56 μM | 1.7 μM | 5 μM | 15 μM | |
| 998276 | 76 | 86 | 95 | 98 | NC |
| 998256 | 60 | 69 | 84 | 94 | NC |
| 998252 | 46 | 60 | 75 | 86 | 0.7 |
| 998216 | 41 | 53 | 76 | 82 | 1.1 |
| 998164 | 43 | 55 | 72 | 84 | 1.0 |
| 998048 | 35 | 46 | 67 | 82 | 1.7 |
| 998140 | 36 | 46 | 72 | 76 | 1.7 |
| 998168 | 43 | 61 | 70 | 73 | 0.8 |
| 998288 | 37 | 53 | 66 | 83 | 1.4 |

TABLE 5-continued

Multi-dose assay of modified oligonucleotides in 4T1 cells

| ION No. | % Inhibition RTS37638 | | | | IC50 |
|---|---|---|---|---|---|
| | 0.56 µM | 1.7 µM | 5 µM | 15 µM | (µM) |
| 998253 | 48 | 65 | 81 | 93 | 0.6 |
| 998277 | 55 | 67 | 78 | 91 | NC |
| 998177 | 35 | 52 | 70 | 85 | 1.4 |
| 998157 | 41 | 60 | 75 | 87 | 0.9 |
| 998149 | 36 | 46 | 65 | 77 | 1.8 |
| 998261 | 30 | 46 | 61 | 78 | 2.2 |
| 998241 | 15 | 37 | 59 | 77 | 3.4 |
| 998069 | 28 | 42 | 64 | 79 | 2.4 |

TABLE 6

Multi-dose assay of modified oligonucleotides in 4T1 cells

| ION No. | % Inhibition RTS37638 | | | | IC50 |
|---|---|---|---|---|---|
| | 0.56 µM | 1.7 µM | 5 µM | 15 µM | (µM) |
| 998258 | 80 | 89 | 95 | 99 | NC |
| 998150 | 69 | 86 | 91 | 95 | NC |
| 998210 | 46 | 63 | 76 | 88 | 0.7 |
| 998278 | 44 | 57 | 73 | 87 | 0.9 |
| 998082 | 55 | 64 | 74 | 86 | NC |
| 998250 | 31 | 48 | 62 | 82 | 2.0 |
| 998294 | 41 | 59 | 72 | 87 | 1.0 |
| 998254 | 25 | 42 | 63 | 81 | 2.5 |
| 998275 | 68 | 82 | 92 | 97 | NC |
| 998215 | 50 | 63 | 81 | 91 | NC |
| 998263 | 46 | 61 | 80 | 90 | 0.7 |
| 998179 | 61 | 73 | 86 | 93 | NC |
| 998279 | 44 | 57 | 75 | 89 | 0.9 |
| 998235 | 23 | 36 | 55 | 74 | 3.5 |
| 998255 | 9 | 37 | 64 | 82 | 3.1 |
| 998291 | 27 | 47 | 72 | 87 | 1.9 |

Example 5

Identification of Optimal ASO Sequence and Dose to Suppress PSMD9 Expression

Treatment groups of C57Bl/6J mice (n=8/group) aged 4-8 weeks are injected with one of ten different anti-sense oligonucleotides (ASOs) targeted against PSMD9, scrambled ASO or saline. Mice are subjected to: doses selected from 5 mg, 25 or 100 mg/kg; dose intervals selected from bi-weekly or weekly and using intraperitoneal injections (sterile PBS) for a treatment period of 3 weeks. Following this, mice are fasted for 16 hours after which they are euthanased and blood and organs including liver, adipose, heart and skeletal muscle are collected.

PSMD9 knockdown in the liver is assessed at both the mRNA and protein level by qPCR and western blotting respectively. Lipidomic analysis is also performed on liver and/or plasma samples.

In accordance with the present disclosure, at least three of the ASOs generate robust knockdown of PSMD9 and this is associated with a reduction in the pathological lipid species in the liver and/or plasma.

Example 6

Anti-PSMD9 ASO to Suppress PSMD9 Expression and Prevent Pathological Lipid Accumulation The action of the most effective anti-PSMD9 ASO's as identified in Example 3 is assessed in C57Bl/6J mice fed a high fat diet (n=12/group), using dose and dose interval as established in Example 3 Initially, the ASOs are administered for 8 weeks with concomitant feeding of a high at diet. At the conclusion of the study, mice are fasted and blood and organs including liver, adipose, heart and skeletal muscle are collected. In accordance with the present description, the ASOs against PSMD9 are associated with reduced (less) hepatic steatosis and/or a reduction in pathological lipid accumulation.

Example 7

Anti-PSMD9 ASO to Suppress PSMD9 Expression and Treat Pathological Lipid Accumulation The action of the most effective anti-PSMD9 ASO's as identified in Example 3 are assessed in a "treatment" setting. Mice are fed a high fat diet or Western diet for up to 8 weeks then administered ASO weekly for up to 8 weeks while continuing on the diet using dose and dose intervals as established in Example 3. At the conclusion of the study, mice are fasted and blood and organs including liver, adipose, heart and skeletal muscle will be collected.

In accordance with the present description, ASOs against PSMD9 or PSMD9 inhibition leads to reduced hepatic steatosis and and/or pathological lipids in the context of steatosis Example 8

Study to Determine Silencing of PSMD9

Figure 8:
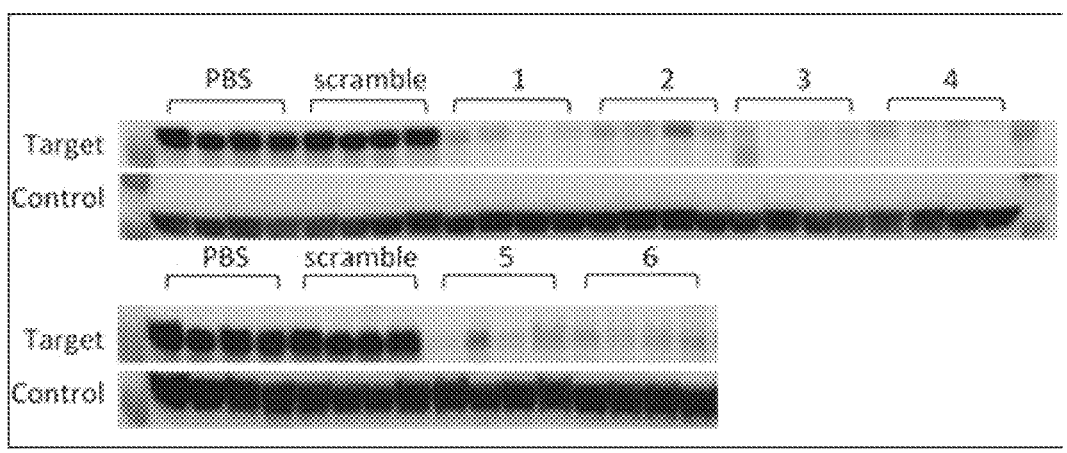
FIG. 8 (a-b) illustrates data showing efficient antisense knock-down of PSMD9 in livers of mice treated with twice weekly 25 mg/kg ASO for 7 days for each test ASO (a) Western blot (n=4) for ASO #1-6 and scrambled ASO control showing PSMD9 abundance (b) All but one ASO (ASO2) demonstrated favourable toxicity profiles as illustrated with analysis of plasma AST and ALT.
Figure 8:
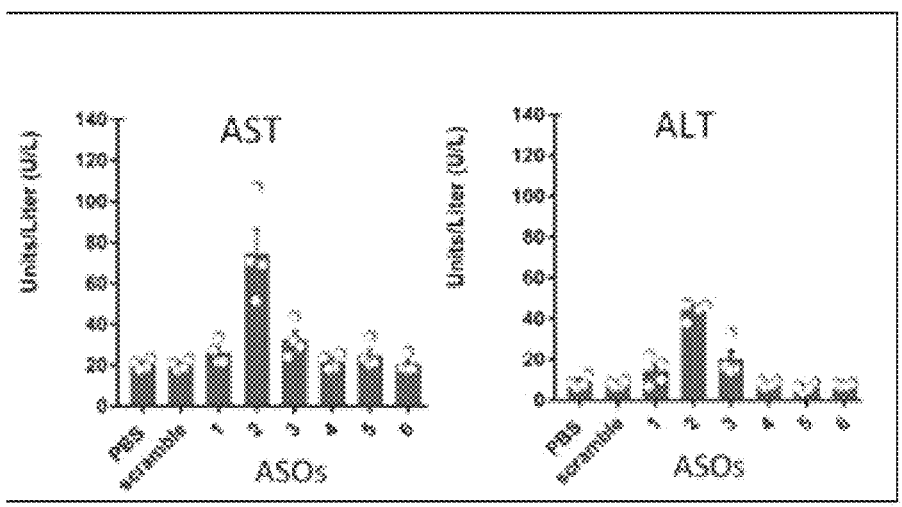

High dose (125 mg/kg) short term dosing over 7 days with 10 ASO was used to determine toxicity and silencing efficacy. Assays for serum AST and ALT were used to assess potential liver toxicity. Assays were also conducted for treatment periods with therapeutic doses of twice or once weekly dosing of 25 mg/kg of 7 days and up to 4 weeks. In these studies, six antisense oligonucleotides were able to almost completely silence PSMD9 protein expression in the liver compared to control scrambled ASO with all but one ASO (ASO2) demonstrating a favourable toxicity profile as indicated by analysis of plasma AST and ALT (see FIG. 8a-b). The once weekly dose resulted in equivalent silencing of PSMD9 after 4 weeks as did the twice weekly dosing Administration of PSMD9 ASO for up to four weeks was not associated with significant changes in plasma. AST/ALT levels, food consumption or body weight (data not shown).

Sequences for effective mouse PSMD9 ASOs and the scrambled (control) ASO are as follows:

```
D9 ASO 3:
            (SEQ ID NO: 6 Ionis no. 998276)
CTCTATGGGTGCCAGC

D9 ASO 5:
            (SEQ ID NO: 7 Ionis no. 998263)
CTCTATCTGAGCACAC

D9 ASO 6:
            (SEQ ID NO: 8 Ionis no. 998164)
GTATTTTTAGCCAGAC

ScrASO:
            (SEQ ID NO: 9 scrambled control)
GGCCAATACGCCGTCA
```

Other PSMD9 ASO are described in Tables 5 and 6.

Example 9

Figure 9:
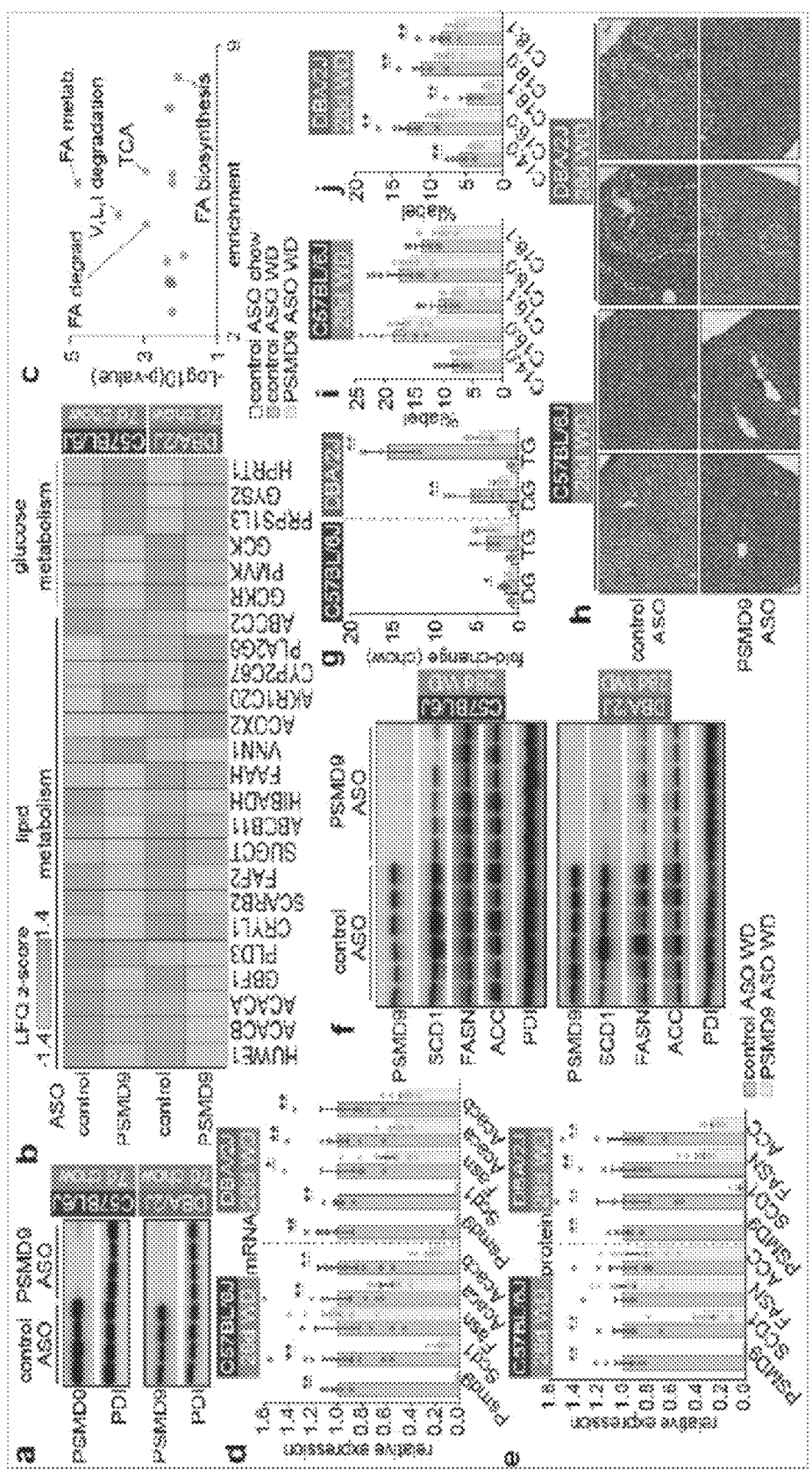
FIG. 9 (a-j) illustrates how down modulating PSMD9 regulates hepatic and plasma lipid abundance. a, Western blots of PSMD9 and PDI in livers of mice treated for 7 days with control- or PSMD9-ASOs (25 mg/kg, n=4 independent animals) b, Heatmap of significantly (ANOVA, p<0.05) regulated proteins from lipid and glucose metabolism pathways in the liver of C57BL/6J and DBA/2J mice treated with control- or PSMD9-ASOs for 7 days (n=4 mice/group). Scale represents average relative abundance (LFQ-score) with orange=high and aqua=low. c, Pathway enrichment analysis using Fisher Exact test with Benjamin-Hochberg correction of the 52 proteins significantly regulated by PSMD9-ASO in both strains d, Expression of Psmd9, Scdl, Fasn, Acaca and Acacb, genes in livers of both strains fed a western diet (WD) for 28 days and treated with control-ASO (greens bars) or PSMD9-ASOs (yellow bars) (presented as fold from control-ASO=1, mean±SEM, n=8 mice/group). e, Quantitation of PSMD9, SCD1, FASN and ACC protein (presented as fold from control-ASO=1, mean±SEM, n=6 control-ASO; n=8 PSMD9-ASO mice/group) as determined by f, Western blot in livers of both strains on WD for 28 days and treated with ASOs g, Plots of hepatic DG and TG abundance in both strains (presented as fold from chow control-ASO=1, mean±SEM, n=4 (chow), n=6 all WD except n=5 DBA/2J control-ASO DG, DBA/2J PSMD9-ASO TG and n=4 DBA/2J control-ASO TG mice/group) treated with control-ASOs on chow diet (white bars), western diet (WD) (green bars), or with PSMD9-ASOs (yellow bars) on WD for 28 days h, Representative (of 5 independent mice) Haematoxylin and Eosin (H+E) staining of liver sections from both strains of mice treated with WD and control-ASOs (top panels) or PSMD9-ASOs (bottom panels) for 28 days. Dotted lines segregate regions of microsteatosis and hepatocyte ballooning (magnification=200×). i-j, Plot (mean±SEM, n=6: control-ASO, n=8: PSMD9-ASO, mice/group) depicting de novo synthesis of individual FA species in both strains following treatment with control-ASO (green bars) or PSMD9-ASOs (yellow bars) for 28 days with WD. Data presented as percent of hepatic FA pool enriched with deuterium label following deuterium oxide treatment for 1 week. * p<0.05 compared to control-ASO, **p<0.01 compared to control-ASO.

PSMD9 Inhibitor Prevents or Reduces Pathological Lipid Accumulation in Liver and Plasma of Mice on a Western Diet Seven day silencing assays as described in Example 8 were conducted with two strains of mice C57BL/6J and DBA/2J mice with ASO #3, #5, and #6). Proteomic analysis of livers of PSMD9 ASO treated C57BL/6J and DBA/2J showed that 52 proteins were differentially regulated across both strains (See FIG. 9 a-b), many of which are known glucose and lipid regulatory proteins (FIG. 9c). Markers of de novo lipogenesis (DNL) (ACACA, ACACAB, FASN and SCD were shown to be attenuated at the protein level by proteomics. Because this study was in health mice fed on a normal chow diet only small (but significant) reductions in specific lipid species including DGs which are one of the strongest correlated lipids to PSMD9 were observed.

To investigate PSMD9 attenuation in lipotoxic conditions ASO (ASO #3, #5 and #6) were administered twice weekly at 25 mg/kg in the two mouse strain in mice concomitantly subjected to a Western diet (high fat, high cholesterol) to induce NAFLD over a 4 week period. At the conclusion of the study, mice are fasted and blood and organs including liver, adipose, heart and skeletal muscle are collected. The results are illustrated in FIG. 9 d-h and show that ASO inhibition led to a prevention of both liver and plasma lipid burden, particularly in DBA/2J mice. PSMD9 silencing in this setting was associated with decreased expression of gene and proteins involved in DNL including acaca, Acacb, and Scd1. Notably, FASN and ACC (Acacalb) proteins were significantly decreased in DBA/2J mice. WD feeding promoted an accrual of hepatic lipids in both strains (FIG. 9g) which was largely prevented in by silencing Psmd9 in DBA/2J mice and to a lesser extend in C57BL/6J mice. Histological analysis corroborated these findings (FIG. 9h).

Notably, PSMD9 silencing also decreased pathological lipid levels in plasma suggesting lipid abundance per se was also reduced. In a further study ASO #3 was administered once weekly at 25 mg/kg to the two strains of mice fed a western diet including one week of deuterium labelling to measure DNL. Prophylactic treatment directly regulated hepatic and lipid abundance at least in part through reduction in hepatic DNL. The results show rescue of hepatic lipid burden associated with the western diet including TG and DG lipid species. The once weekly dose resulted in equivalent silencing as the twice weekly dose and led to a reduction in DNL and a reduction in microsteastosis and hepatocyte ballooning in DBA/2J mice (see FIG. 9 i-j).

Example 10

Figure 10:
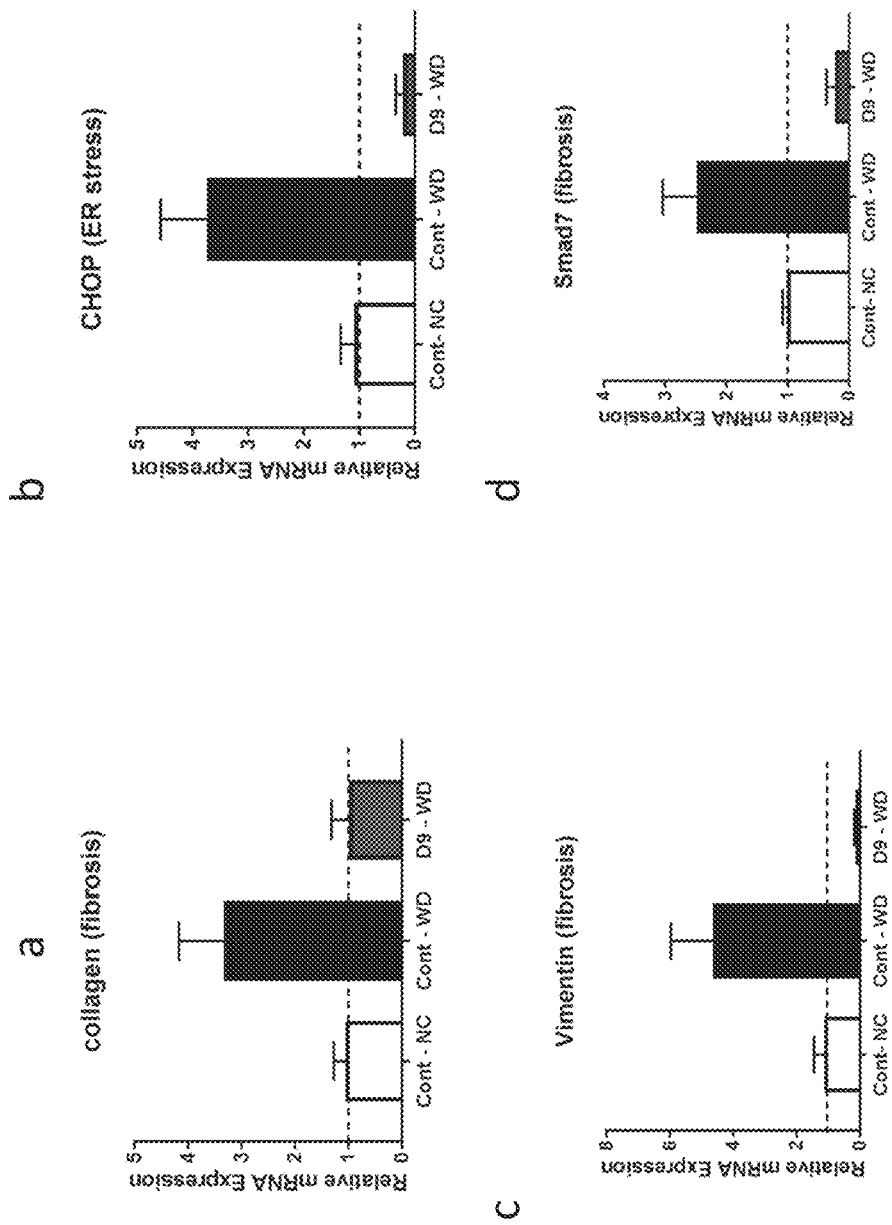
FIG. 10 (a-f) are graphical representations of data illustrating the ability of PSMD9 inhibitors to attenuate markers of inflammation (TNFα), fibrosis (vimentin and collagen and SMAD7) and ER stress (CHOP), all of which are key pathways linked to the progression of NASH and glucose linked to T2D and insulin resistance. C57BL/6J mice were fed a western diet for 4 weeks and treated with ASO control, PSMD9 #3 or PSMD9 #6 concurrently. n=5-6/group; *p<0.05 prior to measuring relative mRNA expression levels. (e-f) down regulation of PSMD9 is effective in reducing blood glucose levels in C57BL6 and DBA mice on a Western diet. As above, C57BL/6J mice were fed a western diet for 4 weeks and treated with ASO control, PSMD9 #3 or PSMD9 #6 concurrently. n=5-6/group; *p<0.05 prior to measuring blood glucose levels.
Figure 10:
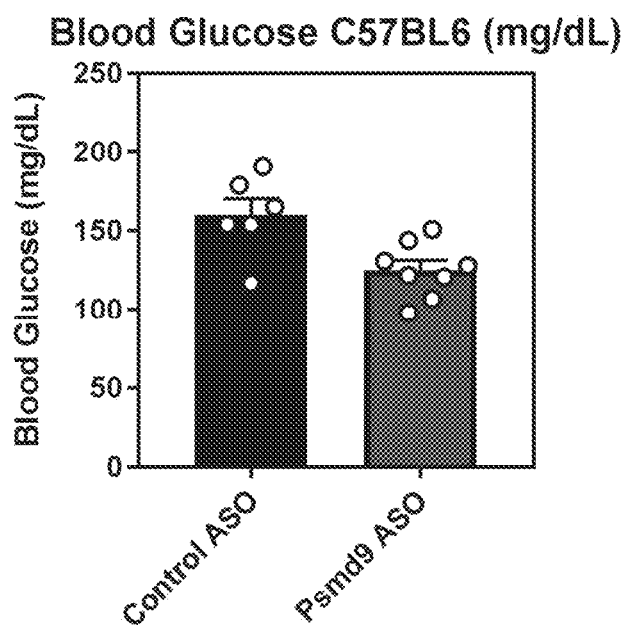
Figure 10:
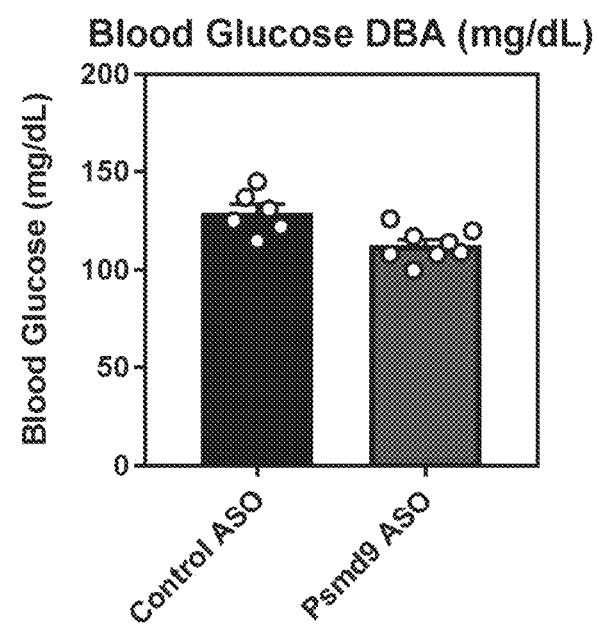

PSMD9 Inhibition Reduces Activation Markers in Key Pathways Linked to the Progression of Steatohepatitis As illustrated in FIG. 10 a-d, down regulation of PSMD9 is effective in attenuating markers of inflammation (TNFα), fibrosis (vimentin and collagen and SMAD7) and ER stress (CHOP), all of which are key pathways linked to the progression of NASH. C57BL/6J mice were fed a Western diet for 4 weeks and treated with ASO control, PSMD9 #3 or PSMD9 #6 concurrently. n=5-6/group; *p<0.05 prior to measuring relative mRNA expression levels. These results indicate that down regulation of PSMD9 will have utility in treating or preventing NASH in man Mouse models of NASH have recently been reviewed by Chen K et al., BBA Volume 1871, Issue 1, January 2019, Pages 117-125 and Farrell G et al., Hepatology. 2018 Oct. 29 who discuss their critical role as human models. In addition, the use of human cell culture assays, the advance of liver organoids and 3-D bio-printing is proposed to be used to facilitate the development of personalised treatments. Mouse models for NASH driven HCC are reviewed in FeMA Febrraio et al., Cell Metab. 2019 Jan. 8; 29(1):18-26 who conclude that the MUP-uPA model exhibit many similarities of the human disease. Farrell G et al., Hepatology. 2018 Oct. 29 supports the use of mouse models as shown herein that exhibit weight gain, abnormal lipid distribution (or adipose dysfunction/inflammation) and insulin resistance resulting in hyperinsulinemia. Also discussed are the protocols that are to be followed to optimise and provide powerful evidence of drug efficacy in mouse models of NASH.

Example 11

PSMD9 Inhibition Reduces Activation Markers in Key Pathways Linked to the Progression of Type 2 Diabetes (T2D)

As illustrated in FIG. 10e-f, down regulation of PSMD9 is effective in reducing blood glucose levels in C57BL6 and DBA mice on a Western diet. As above, C57BL/6J mice were fed a Western diet for 4 weeks and treated with ASO control, PSMD9 #3 or PSMD9 #6 concurrently. n=5-6/group; *p<0.05 prior to measuring blood glucose levels. These results indicate that down regulation of PSMD9 will have utility in treating or preventing T2D and insulin resistance in man Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Within this application, unless otherwise stated, the techniques utilized may be found in any of several well-known references such as: Molecular Cloning: A Laboratory Manual (Sambrook, et al., 1989, Cold Spring Harbor Laboratory Press), PCR Protocols: A Guide to Methods and Applications (Innis, et al. 1990. Academic Press, San Diego, CA), and Harlow and Lane (1988) Antibodies: A Laboratory Manual ch. 14 (Cold Spring Harbor Laboratory, Cold Spring Harbor, NY).

It will be appreciated by persons skilled in the art that many modifications may be made to the above-described embodiments, without departing from the broad general scope of the present disclosure. The present embodiments are, therefore, to be considered in all respects as illustrative and not restrictive.

BIBLIOGRAPHY

Alshehry Z. H. et al. (2015) *Metabolites* 5, 389-403
Alshehry Z. H. et al. (2016) *Circulation* 134, 1637-1650
Andreux, P. A et al. (2012) *Cell* 150, 1287-1299.
Azimifar S B et al. (2014) *Cell metabolism* 20, 1076-1087
Bennett B. J et al. (2010) *Genome research* 20, 281-290
Chick J. M. et al. (2016) *Nature* 534:500-505
Churchill, G. A et al. (2004) *Nature Genetics* 36, 1133-1137
Churchill G. A. et al. (2012) Mammalian genome: official journal of the International Mammalian Genome Society 23, 713-718
Cox J. and Mann M. (2008) *Nature Biotechnology* 26, 1367-1372
Drew, B. G. et al. (2015) *The Journal of biological chemistry* 290, 5566-5581

Eng J. K. et al. (1994) *Journal of the American Society for Mass Spectrometry* 5, 976-989
Ghazalpour et al. (2012) Mammalian genome: official journal of the International Mammalian Genome Society 23, 680-692
Garzon J. I., et al. (2016) *eLife* 5
Harris R., et al. (2017) *The Lancet Gastroenterology & hepatology* 2, 288-297
Hvam et al. *Molecular Therapy* 25(7) July 2017.
Jiang et al. *J Clin Invest.* 2005 April; 115(4):1030-8. Epub 2005 Mar. 10
Langfelder P. and Horvath, S. (2008) *BMC bioinformatics* 9, 559
Luck, S., et al. (2014) *Cell reports* 9, 741-751
Mota et al. *Metabolism* 65(8):1049-1061, 2016
Musso et al. *Nature Reviews, Drug Discovery* 15: 249-274, 2016
Parks B. W et al. (2013) *Cell metabolism* 17, 141-152
Parks B. W et al. (2015) *Cell metabolism* 21, 334-346
Prakash et al. *J. Med. Chem* 2016, 59, 2718-2733
Singh et al *PloS One* (2016) 0164133
Tacer and Rozman J. Lipids (2011) 783976
Watanabe T. K. et al. (1998) *Genomics* 50, 241-250
Williams E G et al. (2016) *Science* 352, aad0189
Wu Y et al. (2014) *Cell* 158, 1415-1430
Xing Xian Yu et al. *Hepatology;* 42:362-371, 2005.

The invention claimed is:

1. A method for treating a subject suffering from hepatic lipid dysregulation or at risk of suffering from same, comprising administering a PSMD9 inhibitor to the subject, wherein the PSMD9 inhibitor is or comprises a polynucleotide, wherein the polynucleotide is a modified oligonucleotide targeting PSMD9.

2. The method of claim 1, wherein the polynucleotide is single-stranded.

3. The method of claim 1, wherein the polynucleotide is double-stranded.

4. The method of claim 1, wherein the modified oligonucleotide comprises at least one modification selected from at least one modified internucleoside linkage, at least one modified sugar moiety, and at least one modified nucleobase.

5. The method of claim 1, wherein the modified oligonucleotide comprises:

A gap segment consisting of linked deoxynucleotides;
A 5' wing segment consisting of linked nucleosides; and
A 3' wing segment consisting of linked nucleosides;
wherein the gap segment is positioned immediately adjacent to and between the 5' wing segment and the 3' wing segment and wherein each nucleoside of each wing segment comprises a modified sugar.

6. The method of claim 1, wherein the polynucleotide comprises an iRNA.

7. The method of claim 1, wherein the polynucleotide is a vector for the expression of the PSMD9 inhibitor.

8. The method of claim 7, wherein the vector is a viral vector.

9. The method of claim 1, wherein the PSMD9 inhibitor is administered in order to reduce the accumulation of pathological lipid species in the subject.

10. The method of claim 1, wherein the PSMD9 inhibitor reduces markers of NASH or T2D such as inflammation, fibrosis, ER stress or glucose levels in the subject.

11. The method of claim 1, further comprising measuring the level of one or more lipid species in a sample from the subject, during or after treatment to determine the effect of the PSMD9 inhibitor in lowering pathological lipid species in the subject.

12. The method of claim 1, further comprising measuring one or more markers of inflammation, fibrosis, ER stress, T2D or insulin resistance before, during or after treatment to determine the effect of the PSMD9 inhibitor in the subject.

13. The method of claim 6, wherein the iRNA comprises shRNA.

14. The method of claim 6, wherein the iRNA comprises siRNA.

15. The method of claim 6, wherein the iRNA comprises miRNA.

16. The method of claim 1, wherein the subject suffers from hepatic lipid dysregulation.

\* \* \* \* \*